(12) United States Patent
Graff et al.

(10) Patent No.: US 6,428,977 B1
(45) Date of Patent: *Aug. 6, 2002

(54) SIGNALIN FAMILY OF TGFβ SIGNAL TRANSDUCTION PROTEINS, AND USES RELATED THERETO

(75) Inventors: Jonathan M. Graff, Newton; Tod M. Woolf, Natick; Ping Jin, Boston; Douglas A. Melton, Lexington, all of MA (US)

(73) Assignee: Curis, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/580,031

(22) Filed: Dec. 20, 1995

(51) Int. Cl.$^7$ ................ C12N 15/12; C12N 15/62; C07K 14/46; C07K 19/00

(52) U.S. Cl. ................ 435/69.1; 435/69.7; 435/252.3; 435/320.1; 435/325; 435/458; 530/350; 530/23.1; 530/23.4; 530/23.5; 530/24.1

(58) Field of Search ................ 536/23.1, 23.4, 536/23.5, 24.1; 435/240.2, 69.1, 69.7, 325, 252.3, 320.1, 458; 530/350

(56) References Cited

U.S. PATENT DOCUMENTS

| | | | |
|---|---|---|---|
| 5,393,739 A | 2/1995 | Bentz et al. | 514/12 |
| 5,413,989 A | 5/1995 | Ogawa et al. | 514/12 |
| 5,422,340 A | 6/1995 | Ammann et al. | 514/12 |
| 5,459,047 A | 10/1995 | Wozney et al. | 435/69.1 |

OTHER PUBLICATIONS

Sambrook et al. Molecular Cloning: A Laboratory Manual Second Edition vols. 1, 2 and 3. Cold Spring Harbor Laboratory Press: Cold Spring Harbor, New York, U.S.A. Nov., 1989, pp. 9.50–9.51.*
Ngo et al., in The Protein Folding Problem an Teritary Structure Prediction, Merz and Le Grand (Eds), Aug. 1994, Springer Verlag, pp. 433 and 492–495.*
Nathan et al. Cytokines in context. Journal of Cell Biology, (Jun. 1991) 113 (5) 981–986.*
Sambrook et al. Molecular Cloning: A Laboratory Manual Second Edition vols. 1, 2 and 3. Cold Spring Harbor Laboratory Press: Cold Spring Harbor, New York, U.S.A. Nov., 1989, pp. 16.2, 17.2 , 17.3, 17.4.*
Graff et al. Studies with a Xenopus BMP receptor suggest that ventral mesoderm–inducing signals override dorsal signals in vivo. Cell Oct. 7, 1994; 79(1):169–179, Nov. 1989.*
Bowie et al. Deciphering the message in protein sequences: tolerance to amino acid substitutions. Science, (Mar. 16, 1990) 247 (4948) 1306–10.*
Sambrook et al. Molecular Cloning: A Laboratory Manual Second Edition, vols. 1, 2 and 3. Cold Spring Harbor Laboratory Press: Cold Spring Harbor, New York, U.S.A., Nov., 1989.*
George et al, "Current methods in sequence comparison and analysis," in Macromolecular Sequencing and Synthesis, Selected Methods and Applications, 1988, D. H. Schlesinger (ed.), Alan R. Liss, Inc., New York, NY, pp. 127–149.*
Barton, "Protein sequence alignment and database scanning," in Protein Structure Prediction, A Practical Approach, 1996 IRL Press at Oxford University, Oxford, UK, pp. 31–63.*
Massague J. TGFbeta signaling: receptors, transducers, and Mad proteins. CELL, (Jun. 28, 1996) 85 (7) 947–50.*
Derynck R, Gelbart WM, Harland RM, Heldin CH, Kern SE, Massague J, Melton DA, Mlodzik M, Padgett RW, Roberts AB, Smith J, Thomsen GH, Vogelstein B, Wang XF. Cell 87 (2): 173 (Oct. 18, 1996) Nomenclature: vertebrate mediators of TGFbeta family signals. [L.*
Graff J M; Bansal A; Melton D A. Xenopus Mad proteins transduce distinct subsets of signals of the TGF–beta superfamily. Cell, (May 17, 1996) 85 (4) 479–87.*
Alberts et al., Molecular Biology of the Cell, 1994, Garland Publishing, Inc., New York, NY, p. 119.*
Field J; Nikawa J; Broek D; MacDonald B; Rodgers L; Wilson I A; Lerner R A; Wigler M. Purification of a RAS–responsive adenylyl cyclase complex from *Saccharomyces cerevisiae* by use of an epitope addition method. Molecular and Cellular Biology, (May 1988.*
Arora, K et al. "The Drosophila schnurri Gene Acts in the Dpp/TGFβ Signaling Pathway and Encodes a Transcription Factor Homologous to the Human MBP Family", *Cell*, vol. 81 (5):781–790 (1995).
Cho, Ken et al., "Molecular Nature of Spemann's Organizer: the Role of the Xenepus Homeobox Gene *goosecoid*", *Cell* vol. 67 pp. 1111–1120 (1991).
Hogan, Brigid et al., "Upside–down ideas vindicated," *Nature*, vol. 376, pp. 210–211 (1995).
Ingham, P. W., et al., "Quantitative effects of *hedgehog and decapentaplegic* activity on the patterning of the Drosophila wing", *Current Biology*, vol. 5, No. 4 pp. 432–440 (1995).
Kingsley, D., "The TGF–β superfamily: new members, new receptors, and new genetic tests of function in different organisms", *Genes and Development*, 8:133–146 (1994).

(List continued on next page.)

Primary Examiner—David S. Romeo
(74) Attorney, Agent, or Firm—Ropes & Gray; Matthew P. Vincent; David P. Halstead

(57) ABSTRACT

The present invention concerns the discovery that proteins encoded by a family of vertebrate genes, termed here signalin-related genes, which are involved in signal transduction induced by members of the TGFβ superfamily. The present invention makes available compositions and methods that can be utilized, for example to generate and/or maintain an array of different vertebrate tissue both in vitro and in vivo.

23 Claims, 5 Drawing Sheets

OTHER PUBLICATIONS

Letsou, A et al. "Drosophila Dpp Signaling is mediated by the punt Gene Product: A Dual Ligand–Binding Type II Receptor of the TGFβ Receptor Family", *Cell,* vol. 80:899–908 (1995).

Massague, J. et al, "The TGF–β family and its composite receptors", *Trends in Cell Biology,* vol. 4, 172–178 (1994).

Newfeld, Stuart et al., "Identification of Two Drosophila TGF–β Family Members in the Grasshopper *Schistocerca americana*", *Journal of Molecular Evolution,* 41:155–160 (1995).

Raftery, L. et al., "Genetic Screens to Identity Elements of the decapentaplegic Signaling Pathway in Drosophila", *Genetics,* 139: 241–254 (1995)

Ruberte, E. et al., An Absolute Requirement for Both the Type II and Type I Receptors, Punt and Thick Veins, for Dpp Signaling in Vivo, *Cel,* vol. 80: 889–897 (1995).

Sekelsky, J. et al., "Genetic Characterizaton and Cloning of Mothers against dpp, a Gene Required for decapentaplegic Function in Drosophila melanogaster", *Genetics* 139: 1347–1358 (1995).

Simmonds, A. et al., "Distinguishable functions for engrailed and invected in anterior–posterior patterning in the Drosophila wing", *Nature,* vol. 376 (3) 424–427 (1995).

Wharton, K. et al., "An activity gradient of decapentaplegic is necessary for the specification of dorsal pattern elements in the Drosophila embryo", *Development* 177: 807–822 (1993).

Wilson, R. et al., "2.2 Mb of contiguous nucleotide sequence from chromosome III of C. elegans", *Nature,* vol. 368 pp. 32–38 (1994).

Winnier, Glenn et al., "Bone morphogenetic protein–4 is required for mesoderm formation and patterning in the moose", *Genes & Development,* vol. 9, pp. 2105–2116 (1995).

Zecca M. et al., "Sequential organizing activities of engrailed, hedgehog and decaptenaplegic in the Drosophila wing", *Development,* 121, 2265–2278 (1995).

* cited by examiner

Control

Signalin 1

Signalin 2

Control

Signalin 1

Signalin 2

*Figure 5*

|  | | Human *signalins* | | | | | | |
|---|---|---|---|---|---|---|---|---|
|  |  | 1 | 3 | 7 | 4 | 5 | 6 | 2 |
|  | 1 | 1 | 5 | 3 |  |  |  |  |
| Xenopus | 3 | 2 | 2 | 4 |  |  |  |  |
| *signalins* | 4 |  |  |  | 3 | 4 |  |  |
|  | 2 |  |  |  |  |  | 1 | 0 |

*Figure 6*

```
hu-signalin-1 > VSHRKGLPHVIYCRVWRWPDLQSHHELKPLECCEFPFGSKQKEV
hu-signalin-2 > VAGRKGFPHVIYARLWRWPDLH*KNELKHVKYCQYAFDLKCDSV
hu-signalin-3 > VSHRKGLPHVIYCRVWRWPDLQSHHGLKPMECCEFPFVSKQKDV
hu-signalin-4 > VAGRKGFPHVIYARLWRWPDLH*KNELKHVKFCQLAFDLKYDDV
hu-signalin-5 > VPHRKGLPHVIYCRLWRWPDLHSHHELKAIENCEYAFNLKKDEV
hu-signalin-6 > VSHRKGLPHVIYCRLWRWPDLHSHHELKAIENCEYAFNLKKDEV
hu-signalin-7 > VSHRKGLPHVIYCRVWRWPDLQSHHELKPLDICEFPFGSKQKEV xe-signalin-1 > VSHRKGLPHVIYCRVWRWPDLQSHHELKPLECCEYPFGSKQKEV
xe-signalin-2 > VSHRKGLPHVIYCRLWRWPDLHSHHELKAIENCEYAFNLKKDEV
xe-signalin-3 > VSHRKGLPHVIYCRVWRWPDLQSHHELKPMECCEFPFGSKQKDV
xe-signalin-4 > VAGRKGFPHVIYARLWHWPDLH*KNELKHVKFCQFAFDLKYDSV
```

SIGNALIN FAMILY OF TGFβ SIGNAL TRANSDUCTION PROTEINS, AND USES RELATED THERETO

FUNDING

Work described herein was supported by funding from the National Institutes of Health. The United States Government has certain rights in the invention.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365–389; Gurdon, J. B., (1992) *Cell* 68: 185–199; Jessell, T. M. et al., (1992) *Cell* 68: 257–270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homoiogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185–199).

Several classes of secreted polypeptides are known to mediate the cell-cell signaling that determines tissue fate during development. An important group of these signaling proteins are the TGFβ superfamily of molecules, which have wide range of functions in many different species. Members of the family are initially synthesized as larger precursor molecules with an amino-terminal signal sequence and a pro-domain of varying size (Kingsley, D. M. (1994) *Genes Dev.* 8:133–146). The precursor is then cleaved to release a mature carboxy-terminal segment of 110–140 amino acids. The active signaling moiety is comprised of hetero- or homodimers of the carboxy-terminal segment (Massague, J. (1990) *Annu. Rev. Cell Biol.* 6:597–641). The active form of the molecule then interacts with its receptor, which for this family of molecules is composed of two distantly related transmembrane serine/threonine kinases called type I and type II receptors (Massague, J. et al. (1992) *Cell* 69:1067–1070; Miyazono, K. A. et al. *EMBO J.* 10:1091–1101). TGFβ binds directly to the type II receptor, which then recruits the type I receptor and modifies it by phosphorylation. The type I receptor then transduces the signal to downstream components, which are as yet unidentified (Wrana et al, (1994) *Nature* 370:341–347).

Several members of the TGFβ superfamily have been identified which play salient roles during vertebrate development. Dorsalin is expressed preferentially in the dorsal side of the developing chick neural tube (Basler et al. (1993) *Cell* 73:687–702). It promotes the outgrowth of neural crest cells and inhibits the formation of motor neuron cells in vitro, suggesting that it plays an important role in neural patterning along the dorsoventral axis. Certain of the bone morphogenetic proteins (BMPs) can induce the formation of ectopic bone and cartilage when implanted under the skin or into muscles (Wozney, J. M. et al. (1988) *Science* 242:1528–1534). In mice, mutations in BMP5 have been found to result in effects on many different skeletal elements, including reduced external ear size and decreased repair of bone fractures in adults (Kingsley (1994) *Genes Dev.* 8:133–146). Besides these effects on bone tissue, BMPs play other roles during normal development. For example, they are expressed in non skeletal tissues (Lyons et al. (1990) *Development* 109:833–844), and injections of BMP4 into developing Xenopus embryos promote the formation of ventral/posterior mesoderm (Dale et al (1992) *Development* 115:573–585). Furthermore, mice with mutations in BMP5 have an increased frequency of different soft tissue abnormalities in addition to the skeletal abnormalities described above (Green, M. C. (1958) *J. Exp. Zool.* 137:75–88).

Members of the activin subfamily have been found to be important in mesoderm induction during Xenopus development (Green and Smith (1990) *Nature* 47:391–394; Thomsen et al. (1990) *Cell* 63:485–493) and inhibins were initially described as gonadal inhibitors of follicle-stimulating hormone from pituitary cells. In addition, antagonists of this signaling pathway can be used to convert embryonic tissue into ectoderm, the default pathway of development in the absence of TGFβ-mediated signals. BMP-4 and activin have been found to be potent inhibitors of neuralization (Wilson, P. A. and Hemmati-Brivanlou, A (1995) *Nature* 376:331–333).

Further evidence for the importance of a TGFβ family member in early vertebrate development comes from a retroviral insertion in the mouse nodal gene. This insertion leads to a failure to form the primitive streak in early embryogenesis, a lack of axial mesoderm tissue, and an overproduction of ectoderm and extraembryonic ectoderm (Conlon et al. (1991) *Development* 111:969–981; Iannaccone et al (1992) *Dev. Dynamics* 194:198–208). The predicted nodal gene product is consistent with previous studies showing that nodal is related to activins and BMPs (Zhou et al. (1993) *Nature* 361:543–547). A role for TGFβ family members in the development of sex organs has also been described; Mullerian inhibitory substance functions during vertebrate male sexual development to cause regression of the embryonic duct system that develops into oviducts and uterus (Lee and Donahoe (1993) *Endocrinol. Rev.* 14:152–164).

Members of this family of signaling molecules also continue to function post-development. TGFβ has antiproliferative effects on many cell types including epithelial cells, endothelial cells, smooth muscle cells, fetal hepatocytes, and myeloid, erythroid, and lymphoid cells. Animals which cannot produce TGFβ1 (homozygous for null mutations in the TGFβ1 gene) have been found to survive until birth with no apparent morphological abnormalities (Shull et al. (1992) *Nature* 359:693–699; Kulkarni et al. (1993) *Proc. Natl. Acac. Sci.* 90:770–774). The animals do die around weaning age, however, owing to massive immune infiltration in may different organs. These data are consistent with the inhibitory effects of TGFβ on lymphocyte growth (Tada et al. (1991) *J. Immunol* 146:1077–1082). In another system, the expression of a TGFβ transgene in the mammary tissue of mice has been shown to inhibit the development and secretory function of mammary tissue during sexual maturation and pregnancy (Jhappan, C. et al. (1993) *EMBO J.* 12:1835–1845; Pierce, D. F. et al. (1993) *Genes Dev.* 7:2308–2317). In addition to these inhibitory effects, TGFβ can also promote the growth of other cell types as evidenced by its role in neovascularization and the proliferation of connective tissue cells. Because of these activities, it plays a key role in wound healing (Kovacs, E. J. (1991) *Immunol Today* 12:17–23)

SUMMARY OF THE INVENTION

The present invention relates to the discovery of a novel family of genes, and gene products, expressed in vertebrate organisms, which genes referred to hereinafter as the "signalin" gene family, the products of which are referred to as signalin proteins. The products of the signalin gene have apparent broad involvement in the formation and maintenance of ordered spatial arrangements of differentiated tissues in vertebrates, and can be used or manipulated to generate and/or maintain an array of different vertebrate tissue both in vitro and in vivo.

In general, the invention features isolated vertebrate signalin polypeptides, preferably substantially pure preparations of one or more of the subject signalin polypeptides. The invention also provides recombinantly produced signalin polypeptides. In preferred embodiments the polypeptide has a biological activity including: an ability to modulate proliferation, survival and/or differentiation of mesodermally-derived tissue, such as tissue derived from dorsal mesoderm; the ability to modulate proliferation, survival and/or differentiation of ectodermally-derived tissue, such as tissue derived from the neural tube, neural crest, or head mesenchyme; the ability to modulate proliferation, survival and/or differentiation of endodermally-derived tissue, such as tissue derived from the primitive gut. Moreover, in preferred embodiments, the subject signalin proteins have the ability to modulate intracellular signal transduction pathways mediated by receptors for members of the Transforming Growth Factor β superfamily of molecules.

In one embodiment, the polypeptide is identical with or homologous to a signalin protein. Exemplary signalin proteins are represented by SEQ ID No. 14, SEQ ID No:15, SEQ ID No:16, SEQ ID No:17, SEQ ID No:18, SEQ ID No:19, SEQ ID No: 20, SEQ ID No:21, SEQ ID No:22, SEQ ID No:23, SEQ ID No:24, SEQ ID No:25, SEQ ID No:26. Related members of the vertebrate signalin family are also contemplated, for instance, a signalin polypeptide preferably has an amino acid sequence at least 60% homologous to a polypeptide represented by any of SEQ ID Nos: 14–26, though polypeptides with higher sequence homologies of, for example, 70, 80%, 90% or are also contemplated. The signalin polypeptide can comprise a full length protein, such as represented in the sequence listings, or it can comprise a fragment corresponding to particular motifs/domians, or to arbitrary sizes, e.g., at least 5, 10, 25, 50, 100, 150 or 200 amino acids in length. In preferred embiments, the polypeptide, or fragment thereof, specifically modulates, by acting as either an agonist or antagonist, the signal transduction activity of a receptor for a transforming growth factor β.

In certain preferred embodiments, the invention features a purified or recombinant signalin polypeptide having a molecular weight in the range of 45 kd to 70 kd. For instance, preferred signalin polypeptide chains of the α and β subfamilies, described infra, have molecular weights in the range of 45 kd to about 55 kd, even more preferably in the range of 50–55 kd. In another illustrative example, preferred signalin polypeptide chains of the γ subfamily have molecular weights in the range of 60 kd to about 70 kd, even more preferably in the range of 63–68 kd. It will be understood that certain post-translational modifications, e.g., phosphorylation and the like, can increase the apparent molecular weight of the signalin protein relative to the unmodified polypeptide chain.

In another embodiment, the signalin polypeptide comprises a signalin motif represented in the general formula shown in SEQ ID No:28. In a preferred embodiment the signalin motif corresponds to a signalin motif represented in one of SEQ ID Nos: 14–26. In another embodiment, the signalin polypeptide of the invention comprises a ν domain represented in the general formula SEQ ID No:27. In a preferred embodiment the ν region corresponds to a ν domain represented in one of SEQ ID Nos:14–26. In another preferred embodiment, the signalin polypeptide of the invention comprises a χ domain represented in the general formula SEQ ID No:29. In a further preferred embodiment the χ region corresponds to a χ domain represented in one of SEQ ID Nos:14–26. In another perferred embodiment, the signalin polypeptide can modulate, either stimulate or antagonize, intracellular pathways mediated by a receptor for a TGFβ. In still another embodiment, the polypeptide comprises an amino acid sequence represented in the general formula: LDGRLQVSHRKGLPHVIYCRVWRWP-DLQSHHELKPXECCEXPFXSKQKXV (SEQ ID No:30). In still a further embodiement, the signalin polypeptide of the present invention comprises an amino acid sequence represented by the general formula: LDGRLQVAGRKGF-PHVIYARLWXWPDLHKNELKHVKFCQX-AFDLKYDXV (SEQ ID No:31). In an additional embodiement, the signalin polypeptide of the present invention comprises an amino acid sequence represented by the general formula: LDGRLQVXHRKGLPHVIYCRLWRW-PDLHSHHELKAIENCEYAFNLKKDEV (SEQ ID No:32).

In another preferred embodiment, the invention features a purified or recombinant polypeptide fragment of a signalin protein, which polypeptide has the ability to modulate, e.g., mimic or antagonize, a the activity of a wild-type signalin protein. Preferably, the polypeptide fragment comprises a signalin motif.

Moreover, as described below, the preferred signalin polypeptide can be either an agonist (e.g. mimics), or alternatively, an antagonist of a biological activity of a naturally occurring form of the protein, e.g., the polypeptide is able to modulate differentiation and/or growth and/or survival of a cell responsive to authentic signalin proteins. Homologs of the subject signalin proteins include versions of the protein which are resistant to post-translation modification, as for example, due to mutations which alter modification sites (such as tyrosine, threonine, serine or aspargine residues), or which inactivate an enzymatic activity associated with the protein.

The subject proteins can also be provided as chimeric molecules, such as in the form of fusion proteins. For instance, the signalin protein can be provided as a recombinant fusion protein which includes a second polypeptide portion, e.g., a second polypeptide having an amino acid sequence unrelated (heterologous) to the signalin polypeptide, e.g. the second polypeptide portion is glutathione-S-transferase, e.g. the second polypeptide portion is an enzymatic activity such as alkaline phosphatase, e.g. the second polypeptide portion is an epitope tag.

In a preferred embodiment the signalin polypeptide of the present invention modulates signal transduction from a TGFβ receptor. For example, the signalin polypeptide may modulate the transduction of a TGFβ receptor for a member of the dpp family, e.g., dpp, BMP2, or BMP4. In a other preferred embodiement, the signalin polypeptide modulates the signaling of a TGFβ other than a dpp family member. For instance, the signalin polypeptide may be involved in signalling from one or more of BMP5, BMP6, BMP7, BMP8, 60A, GDF5, GDF6, GDF7, GDF1, Vg1, dorsalin, BMP3, GDF10, nodal, inhibins, activins TGFβ1, TGFβ2, TGFβ3, MIS, GDF9 or GDNE.

In yet another embodiment, the invention features a nucleic acid encoding a signalin polypeptide, or polypeptide homologous thereto, which polypeptide has the ability to modulate, e.g., either mimic or antagonize, at least a portion of the activity of a wild-type signalin polypeptide. Exemplary signalin polypeptides are represented by SEQ ID No:14, SEQ ID No:15, SEQ ID No. 16, SEQ ID No:17, SEQ ID No:18, SEQ ID No:19, SEQ ID No:20, SEQ ID No:21, SEQ ID No: 22, SEQ ID No:23, SEQ ID No:24, SEQ ID No:25, SEQ ID No:26. In another embodiment the nucleic acid of the present invention hybridizes under stringent conditions with one or more of the nucleic acid sequences in SEQ ID No:1–13. In preferred embidiments, the nucleic acid encodes a polypeptide which specifically modulates, by acting as either an agonist or antagonist, the signal transduction activity of a receptor for a transforming growth factor β.

In another embodiment, the nucleic acid encodes an amino acid sequence which comprises a signalin motif represented in the general formula shown in SEQ ID No:28. In preferred embodiment the signalin motif corresponds to a signalin motif represented in one of SEQ ID Nos:14–26. In another embodiment, the nucleic acid of the invention encodes an amino acid sequence which comprises a v domain represented in the general formula SEQ ID No:27. In a preferred embodiment the encoded v region corresponds to a v domain represented in one of SEQ ID Nos:14–26. In another embodiment, the nucleic acid encodes a signalin polypeptide of the invention which comprises a χ domain represented in the general formula SEQ ID No:29. In a preferred embodiment the encoded χ region corresponds to a χ domain represented in one of SEQ ID Nos:14–26. In still a another embodiment, the nucleic acid sequence encodes a polypeptide which comprises an amino acid sequence represented in the general formula: LDGRLQVSHRKGLPH-VIYCRVWRWPDLQSHHELKPXECCEXPFXSKQKXV (SEQ ID NO: 30). In another embodiement, the nucleic acid of the present invention encodes a polypeptide which comprises an amino acid sequence represented by the general formula, LDGRLQVAGRKGFPHVIYARLWXWPDLH-KNELKHVKFCQXAFDLKYDXV (SEQ ID NO: 30). In an still another embodiement, the nucleic acid encodes a polypeptide which comprises an amino acid sequence represented by the general formula, LDGRLQVXHRKGLPH-VIYCRLWRWPDLHSHHELKAIENCEYAFNLKKDEV (SEQ ID NO. 32).

Another aspect of the present invention provides an isolated nucleic acid having a nucleotide sequence which encodes a signalin polypeptide. In preferred embodiments, the encoded polypeptide specifically mimics or antagonizes inductive events mediated by wild-type signalin proteins. The coding sequence of the nucleic acid can comprise a sequence which is identical to a coding sequence represented in one of SEQ ID Nos: 1–13, or it can merely be homologous to one or more of those sequences.

Furthermore, in certain preferred embodiments, the subject signalin nucleic acid will include a transcriptional regulatory sequence, e.g. at least one of a transcriptional promoter or transcriptional enhancer sequence, which regulatory sequence is operably linked to the signalin gene sequence. Such regulatory sequences can be used in to render the signalin gene sequence suitable for use as an expression vector. This invention also contemplates the cells transfected with said expression vector whether prokaryotic or eukaryotic and a method for producing signalin proteins by employing said expression vectors.

In yet another embodiment, the nucleic acid hybridizes under stringent conditions to a nucleic acid probe corresponding to at least 12 consecutive nucleotides of either sense or antisense sequence of one or more of SEQ ID Nos:1–13; though preferably to at least 25 consecutive nucleotides; and more preferably to at least 40, 50 or 75 consecutive nucleotides of either sense or antisense sequence of one or more of SEQ ID Nos:1–13.

Yet another aspect of the present invention concerns an immunogen comprising a signalin polypeptide in an immunogenic preparation, the immunogen being capable of eliciting an immune response specific for a signalin polypeptide, e.g. a humoral response, e.g. an antibody response; e.g. a cellular response. In preferred embodiments, the immunogen comprising an antigenic determinant, e.g. a unique determinant, from a protein represented by one of SEQ ID Nos. 14–26.

A still further aspect of the present invention features antibodies and antibody preparations specifically reactive with an epitope of the signalin immunogen.

The invention also features transgenic non-human animals, e.g. mice, rats, rabbits, chickens, frogs or pigs, having a transgene, e.g., animals which include (and preferably express) a heterologous form of a signalin gene described herein, or which misexpress an endogenous signalin gene, e.g., an animal in which expression of one or more of the subject signalin proteins is disrupted. Such a transgenic animal can serve as an animal model for studying cellular and tissue disorders comprising mutated or misexpressed signalin alleles or for use in drug screening.

The invention also provides a probe/primer comprising a substantially purified oligonucleotide, wherein the oligonucleotide comprises a region of nucleotide sequence which hybridizes under stringent conditions to at least 12 consecutive nucleotides of sense or antisense sequence of SEQ ID No:1–13, or naturally occurring mutants thereof. Nucleic acid probes which are specific for each of the classes of vertebrate signalin proteins are contemplated by the present invention, e.g. probes which can discern between nucleic acid encoding an α, β, or γ signalin. In preferred embodiments, the probe/primer further includes a label group attached thereto and able to be detected. The label group can be selected, e.g., from a group consisting of radioisotopes, fluorescent compounds, enzymes, and enzyme co-factors. Probes of the invention can be used as a part of a diagnostic test kit for identifying dysfunctions associated with mis-expression of a signalin protein, such as for detecting in a sample of cells isolated from a patient, a level of a nucleic acid encoding a subject signalin protein; e.g. measuring a signalin mRNA level in a cell, or determining whether a genomic signalin gene has been mutated or deleted. These so called "probes/primers" of the invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject signalin proteins so as to inhibit expression of that protein, e.g. by inhibiting transcription and/or translation. Preferably, the oligonucleotide is at least 12 nucleotides in length, though primers of 25, 40, 50, or 75 nucleotides in length are also contemplated.

In yet another aspect, the invention provides an assay for screening test compounds for inhibitors, or alternatively, potentiators, of an interaction between a signalin protein and a signalin binding protein or nucleic acid sequence. An exemplary method includes the steps of (i) combining a signalin polypeptide or fragment thereof, a signalin binding element, and a test compound, e.g., under conditions wherein, but for the test compound, the signalin protein and binding element are able to interact; and (ii) detecting the formation of a complex which includes the signalin protein and the binding element either by directly quantitating the complex or by measuring inductive effects of the signalin protein. A statistically significant change, such as a decrease, in the formation of the complex in the presence of a test compound (relative to what is seen in the absence of the test compound) is indicative of a modulation, e.g., inhibition, of the interaction between the signalin protein and its binding element.

Yet another aspect of the present invention concerns a method for modulating one or more of growth, differentiation, or survival of a mammalian cell responsive to signalin induction. In general, whether carries out in vivo, in vitro, or in situ, the method comprises treating the cell with an effective amount of a signalin polypeptide so as to alter, relative to the cell in the absence of signalin treatment, at least one of (i) rate of growth, (ii) differentiation, or (iii) survival of the cell. Accordingly, the method can be carried out with polypeptides mimics the effects of a naturally-occurring signalin protein on the cell, as well as with polypeptides which antagonize the effects of a naturally-occurring signalin protein on said cell. In preferred embodiments, the signalin polypeptide provided in the subject method are derived from vertebrate sources, e.g., are vertebrate signalin polypeptides. For instance, preferred polypeptides includes an amino acid sequence identical or homologous to an amino acid sequence (e.g., including bioactive fragments) designated in one of SEQ ID No:14, SEQ ID No:15, SEQ ID No:16, SEQ ID No:17, SEQ ID No:18, SEQ ID No:19, SEQ ID No:20, SEQ ID No:21, or SEQ ID No:12, SEQ ID No:23, SEQ ID No:24, SEQ ID No:25, SEQ ID No:26. Furthermore, the present invention contemplates the use of other metazoan (e.g., invertebrate) homologs of the signalin polypeptides or bioactive fragments thereof equivalent to the subject vertebrate fragments.

In one embodiment, the subject method includes the treatment of testicular cells, so as modulate spermatogenesis. In another embodiment, the subject method is used to modulate osteogenesis, comprising the treatment of osteogenic cells with a signalin polypeptide. Liekwise, where the treated cell is a chondrogenic cell, the present method is used to modulate chondrogenesis. In still another embodiment, signalin polypeptides can be used to modulate the differentiation of neural cells, e.g., the method can be used to cause differentiation of a neuronal cell, to maintain a neuronal cell in a differentiated state, and/or to enhance the survival of a neuronal cell, e.g., to prevent apoptosis or other forms of cell death. For instance, the present method can be used to affect the differentiation of such neuronal cells as motor neurons, cholinergic neurons, dopanergic neurons, serotenergic neurons, and peptidergic neurons.

The present method is applicable, for example, to cell culture technique, such as in the culturing of neural and other cells whose survival or differentiative state is dependent on signalin function. Moreover, signalin agonists and antagonists can be used for therapeutic intervention, such as to enhance survival and maintenance of neurons and other neural cells in both the central nervous system and the peripheral nervous system, as well as to influence other vertebrate organogenic pathways, such as other ectodermal patterning, as well as certain mesodermal and endodermal differentiation processes. In an exemplary embodiment, the method is practiced for modulating, in an animal, cell growth, cell differentiation or cell survival, and comprises administering a therapeutically effective amount of a signalin polypeptide to alter, relative the absence of signalin treatment, at least one of (i) rate of growth, (ii) differentiation, or (iii) survival of one or more cell-types in the animal.

Another aspect of the present invention provides a method of determining if a subject, e.g. a human patient, is at risk for a disorder characterized by unwanted cell proliferation or aberrant control of differentiation. The method includes detecting, in a tissue of the subject, the presence or absence of a genetic lesion characterized by at least one of (i) a mutation of a gene encoding a signalin protein, e.g. represented in one of SEQ ID Nos: 14–26, or a homolog thereof; or (ii) the mis-expression of a signalin gene. In preferred embodiments, detecting the genetic lesion includes ascertaining the existence of at least one of: a deletion of one or more nucleotides from a signalin gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; or a non-wild type level of the protein.

For example, detecting the genetic lesion can include (i) providing a probe/primer including an oligonucleotide containing a region of nucleotide sequence which hybridizes to a sense or antisense sequence of a signalin gene, e.g. a nucleic acid represented in one of SEQ ID Nos: 1–13, or naturally occurring mutants thereof, or 5' or 3' flanking sequences naturally associated with the signalin gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the signalin gene and, optionally, of the flanking nucleic acid sequences. For instance, the probe/primer can be employed in a polymerase chain reaction (PCR) or in a ligation chain reaction (LCR). In alternate embodiments, the level of a signalin protein is detected in an immunoassay using an antibody which is specifically immunoreactive with the signalin protein.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 5 is a matrix illustrating a possible grouping of the signalin family into at least three different sub-families. Blacked-out boxes represent >10 mismatches over the signalin motif.

FIG. 6 depicts an alignment of a portion of the signalins identified in both humans and Xenopus.

DETAILED DESCRIPTION OF THE INVENTION

Figure 1:
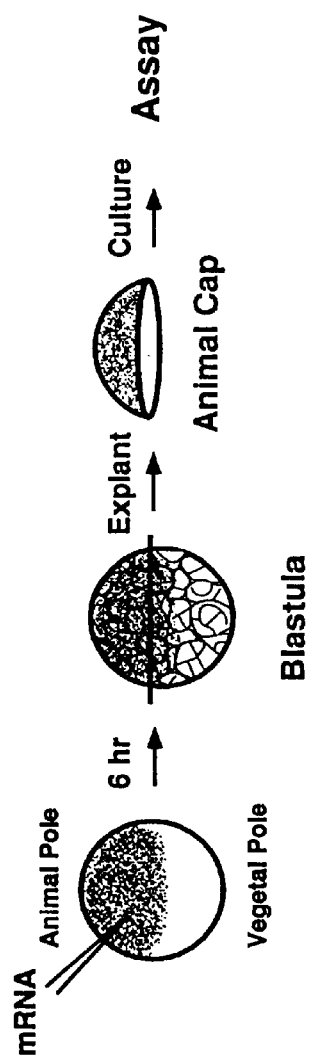
FIG. 1 is an illustration of the model system used to test the biological activities of the signalin proteins described in the present invention.

Of particular importance in the development and maintenance of tissue in vertebrate animals is a type of extracellular communication called induction, which occurs between neighboring cell layers and tissues (Saxen et al. (1989) *Int J Dev Biol* 33:21–48; and Gurdon et al. (1987) *Development* 99:285–306). In inductive interactions, chemical signals secreted by one cell population influence the developmental fate of a second cell population. Typically, cells responding to the inductive signals are diverted from one cell fate to another, neither of which is the same as the fate of the signaling cells. Inductive signals are transmitted by key regulatory proteins that function during development to determine tissue patterning. For example, signals mediated by the TGFβ superfamily have been shown to play a variety of roles, including participating in vertebrate tissue induction.

The present invention concerns the discovery of a family of vertebrate genes, referred to herein as "signalins", which function in intracellular signal transduction pathways initiated by members of the TGFβ-superfamily, and have a role in determining tissue fate and maintenance. For instance, the results provided below indicate that proteins encoded by the vertebrate signalin genes may participate in the control of development and maintenance of a variety of embryonic and adult tissues. For example, during embryonic induction, certain of the signalins are implicated in the differentiation and patterning of both dorsal and ventral mesoderm.

The family of vertebrate signalin genes or gene products provided by the present invention apparently consists of at least seven different members which can be grouped into at least three different subclasses within the signalin family. The vertebrate signalins are related, apparently both in sequence and function, to the drosophila and *C. Ellen* MAD genes (Sekelsky et al. (1995) *Genetics* 139:1347). The cDNAs corresponding to vertebrate signalin gene transcripts were initially cloned from Xenopus and are, arbitrarily, designed as Xe-signalin 1–4. As described in the appended examples, degenerate primers from the cloning of the Xenopus signalins were also used to clone human homologs of this gene family. As a result, cDNA's for at least seven different human signalin transcripts have been identified, and are designated herein, again arbitrarily, as Hu-signalin 1–7. Provided in Table 1 below is a guide to the designated SEQ ID numbers for the nucleotide and amino acid sequences for each signalin clone.

TABLE 1

Guide to signalin sequences in Sequence Listing

|  | Nucleotide | Amino Acid |
| --- | --- | --- |
| Xe-signalin 1 | SEQ ID No. 1 | SEQ ID No. 14 |
| Xe-signalin 2 | SEQ ID No. 2 | SEQ ID No. 15 |
| Xe-signalin 3 | SEQ ID No. 3 | SEQ ID No. 16 |
| Xe-signalin 4 | SEQ ID No. 4 | SEQ ID No. 17 |
| Hu-signalin 1 | SEQ ID No. 5 | SEQ ID No. 18 |
| Hu-signalin 2 | SEQ ID No. 6 | SEQ ID No. 19 |
| Hu-signalin 3 | SEQ ID No. 7 | SEQ ID No. 20 |
| Hu-signalin 4 | SEQ ID No. 8 | SEQ ID No. 21 |
| Hu-signalin 5 | SEQ ID No. 9 | SEQ ID No. 22 |
| Hu-signalin 6 | SEQ ID No. 10 | SEQ ID No. 23 |
| Hu-signalin 7 | SEQ ID No. 11 | SEQ ID No. 24 |

From the apparent molecular weights, the family of vertebrate signalin proteins apparently ranges in size from about 45 kd to about 70 kd for the unmodified polypeptide chain. For instance, Xe-signalin 1 and 3 have apparent molecular weights of about 52.2 kd, Xe-signalin 2 has an apparent molecular weight of about 52.4 kd, and Xe-signalin 4 has an apparent molecular weight of about 64.9 kd.

Analysis of the vertebrate signalin sequences revealed no obvious similarities with any previously identified domains or motifs. However, the fact that each full-length clone lacks a signal sequence, along with the observation that signalin proteins can be detected in both the nucleus and the cytoplasm, indicates that the vertebrate signalin genes encode intracellular proteins.

The above notwithstanding, careful inspection of the clones suggests at least two novel domains, one or both of which may be characteristic of the vertebrate signalin family. The first apparently conserved structural element of the signalin family occurs in the N-terminal portion of the molecule, and is designated herein as the "v domain". With reference to xe-signalin-1, the v domain corresponds to amino acid residues Leu37-Val130. By alignment of the vertebrate signalin clones, the element is represented by the consensus sequence: LVKKLK-X(1)-CVTI-X(2)-RXLDGRLQVXXRKGXPHVIYXRXWPDL-X(3)-VCXNPYHYXRV (SEQ ID No. 27), wherein X(1) represents from about 17–25 residues, X(2) represents from about 1–35 residues, and X(3) represents about 20–25 residues, and each of the other X's represent any single amino acid, though more preferably represent an amino acid residue in the corresponding vertebrate signalin sequences of the appended sequence listing.

Within the v domain, there is a motif which is highly conserved not only amongst the vertebrate signalins, but also amongst the related *drosophila* and *C. elegans* MAD polypeptides. In particular, this motif (referred to herein as a "signalin-motif") includes the consensus sequence LDGR-LQVXXRKGXPHVIYXRXWXWPDL (SEQ ID No. 28). Again, each occurence of x independently represent any single amino acid, though more preferably represent an amino acid residue in the corresponding vertebrate signalin sequences of the appended sequence listing.

Another apparent motif occurs in the C-terminal portion of the signalin family. Referred to herein as the "χ motif", it corresponds to amino acid residues Leu405-Leu450 of xe-signalin-1. Again, by alignment of the vertebrate clones presently sequenced, the χ motif can be represented by the consensus sequence LXXXCXXRXSFVKG-WGXXXXRQXXXXTPCWIEXHLXXXLQXLDXVL (SEQ ID No. 29), wherein each occurence of X independently represent any single amino acid, though more preferably represent an amino acid residue in the corresponding vertebrate signalin sequences of the appended sequence listing.

Not wishing to be bound by any particular theory, analysis of one of the apparently conserved motifs (the signalin motif) suggests that the signalin protein family can be grouped into at least three different sub-families. As FIGS. 5 and 6 illustrate, xe-signalins 1 and 3 and hu-signalins 1, 3 and 7 apparently form one sub-family of signalins (the "α-subfamily" or "α-signalins"). Likewise, xe-signalin 4 and hu-signalins 4 and 2 form a second apparent sub-family (the "β-subfamily" or "β-signalins"), and xe-signalin 2 and hu-signalins 5 and 6 form a third sub-family (the "γ-subfamily" or "γ-signalins"). Comparison of the amino acid sequence around the signalin motif amongst members of the α-subfamily demonstrates a consensus sequence for a signalin motif represented by LDGRLQVSHRKGLPHVIY-CRVWRWPDLQSHHELKPXECCEXPFXSKQKXV (SEQ ID No. 30). Likewise, the β and γ subfamiles are characterized by the signalin motif consensus sequences LDGR-LQVAGRKGFPHVIYARLWXWPDLH-KNELKHVKFCQXAFDLKYDXV (SEQ ID No. 31) and LDGRLQVXHRKGLPHVIYCRLWRWP-DLHSHHELKAIENCEYAFNLKKDEV (SEQ ID No. 32), respectively.

Furthermore, as described in more detail below, portions of human signalin genes have been identified in the expressed sequence tag (EST) libraries based on conservation of one or more of the above structural elements. Based on analysis of certain of these structural elements, contiguous portions of human signalin DNA sequence were established by connecting appropriate EST fragments and correcting for errors in the EST sequences (e.g. frame shift errors, etc.).

In particular, an N-terminal fragment of a human cDNA was assembled from certain of the EST sequences and included the signalin motif of the human cloned sequence hu-signalin 1. The 170 residue fragment, represented by SEQ ID No. 12 (nucleotide) and SEQ ID No. 25 (amino acid), is a member of the α-subfamily, with substantial homology to other members of the α-subfamily even outside the signalin motif.

In similar fashion, a 121 residue C-terminal portion of a human signalin clone was assembled from the EST sequences based on sequences for the Xenopus signalin clones. Analysis of the nucleotide (SEQ ID No. 13) and amino acid (SEQ ID No. 26) sequences of the fragment revealed that it most closely resembled xe-signalin 2, and accordingly is apparently a portion of a transcript for a γ-subfamily member.

Moreover, the present experimental results suggest that the signalin family is significantly larger than the 6 Xenopus clones and 7 human clones. Accordingly, other members of each of the three designated sub-families are expected to exist, as are yet other sub-families. In addition, the fact that there is substantial homology between signalin proteins of different vertebrate species indicates that the signalin sequences provided in the present invention could be used to clone signalin homologs from other vertebrates, including fish, birds, and other amphibia and mammals.

Experimental evidence indicates a functional role for the signalins in signal transduction mediated by members of the TGFβ superfamily. As described in more detail below, the roles of certain of the signalins were tested by ectopic expression in one-cell embryos. For instance, at the blastula stage, animal caps were explanted and cultured until sibling control embryos developed to either stage 11 (gastrula, early) or stage 35 (tadpole, late). After culturing, the explants were examined for morphology, histology, and molecular markers. As detailed in the attached Examples, mRNA encoding xe-signalin1 converts ectoderm into ventral mesoderm that does not express the dorsal markers, muscle actin or NCAM, but does express the ventral marker, Globin. These data place xe-signalin1 in the signal transduction cascade of the BMPs. The role of xe-signalin2 was tested using the same methodology. As shown in the Examples below, xe-signalin2 also converts the fate of the animal pole from ectoderm to mesoderm. In contrast to xe-signalin1, however, the xe-signalin2-induced mesoderm is dorsal in character. Xe-signalin2 induces the expression of the molecular markers: brachyury, Xwnt-8, goosecoid, and actin, further indicating the presence of dorsal mesoderm. This places xe-signalin2 in the signal transduction cascade of the TGFβs, Vg1, and activin. These data provide a basis for understanding the integration of growth and patterning in the developing vertebrate embryo which can have important implications in the treatment of disorders arising in tissue of, for example, mesodermal and/or ectodermal origin.

Another line of experiments reported below demonstrate that at least some of the signalins are post-translationally modified. For example, phosphorylated forms of the proteins have been detected. Moreover, the nuclear-localized forms of the signalin proteins appear to shifted slightly in molecular weight, indicating modification relative to the cytosolic forms. Such modifications may be in the form of, for example, phosphorylation, ubiquitinylation, acylation, or the like. Post-translational modification of the signalins may result in the localization observed, and may also contribute to protein-protein and/or protein-DNA interactions, or in changes to an intrinsic enzymatic activity of the signalin, or in changes to the stability of the protein (e.g., its half-life).

Additionally, the vertebrate signalin gene products are apparently differentially expressed in various tissue. Briefly, using degenerate primers from the signalin motif, human cDNA samples were amplified from various tissues. A strong predominant band at the correct size for a signalin PCR product was observed in the PCR reactions for each of kidney, liver, lung, mammary gland, pancreas, spleen, testis and thymus. An important aspect of this data is the observation that signalin gene products are expressed throughout a diverse range of adult tissues.

The "A-tract" sequencing described below further demonstrates that the numerous different signalin transcripts can be expressed in each tissue, and that the pattern of expression differs from one tissue type to the next, consistent with the notion that tissue-specific responses to individual members the TGFβ superfamily may be controlled at least in part by differential expression of signalins amongst various tissue.

A salient feature of the vertebrate signalins deriving from this data not only implicates the signalin gene products in TGFβ-mediated signaling, but also strongly suggests that the diversity of the signalin family is important to the diversity of responses for each member of the TGFβ family. That is, the ability of a cell to respond to a particular TGFβ, and the type of response the cell presents upon induction by the growth factor can be dependent at least in part upon which signalin gene products are expressed in the cell and/or engaged (or modified) by signals propagated from a particular TGFβ receptor. For example, the involvement of particular signalin proteins, or the stoiciometry thereof, may be important to the differential signalling by members of the TGF-β super family. Certain of the signalin proteins may specfically involved in the signalling by members of the TGFβ sub-family, the activin sub-family, the DVR sub-family (or even more specifically the decapentaplegic or 60A sub-families), gross differentiation factor 1 (GDF-1), GDF-3/VGR-2, dorsalin, nodal, mullerian-inhibiting substance (MIS), or glial-derived neurotrophic growth factor (GDNF).

Accordingly, certain aspects of the present invention relate to nucleic acids encoding vertebrate signalin proteins, the signalin proteins themselves, antibodies immunoreactive with signalin proteins, and preparations of such compositions. Moreover, the present invention provides diagnostic and therapeutic assays and reagents for detecting and treating disorders involving, for example, aberrant expression (or loss thereof) of vertebrate signalin homologs. In addition, drug discovery assays are provided for identifying agents which can modulate the biological function of signalin proteins, such as by altering the binding of vertebrate signalin molecules to either downstream or upstream elements in the TGFβ signal transduction pathway. Such agents can be useful therapeutically to alter the growth and/or differentiation of a cell. Other aspects of the invention are described below or will be apparent to those skilled in the art in light of the present disclosure.

For convenience, certain terms employed in the specification, examples, and appended claims are collected here.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding one of the vertebrate signalin polypeptides of the present invention, including both exon and (optionally) intron sequences. A "recombinant gene" refers to nucleic acid encoding a vertebrate signalin polypeptide and comprising vertebrate signalin-encoding exon sequences, though it may optionally include intron sequences which are either derived from a chromosomal vertebrate signalin gene or from an unrelated chromosomal gene. Exemplary recombinant genes encoding the subject vertebrate signalin polypeptide are represented in the appended Sequence Listing. The term "intron" refers to a DNA sequence present in a given vertebrate signalin gene which is not translated into protein and is generally found between exons.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a vertebrate signalin polypeptide or, where anti-sense expression occurs from the transferred gene, the expression of a naturally-occurring form of the signalin protein is disrupted.

As used herein, the term "specifically hybridizes" refers to the ability of the probe/primer of the invention to hybridize to at least 15 consecutive nucleotides of a vertebrate signalin gene, such as a signalin sequence designated in one of SEQ ID Nos:1–13, or a sequence complementary thereto, or naturally occurring mutants thereof, such that it has less than 15%, preferably less than 10%, and more preferably less than 5% background hybridization to a cellular nucleic acid (e.g., mRNA or genomic DNA) encoding a protein other than a signalin protein, as defined herein. In preferred embodiments, the oligonucleotide probe specifically detects only one of the subject signalin paralogs, e.g., does not substantially hybridize to other signalin homologs.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant vertebrate signalin genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of signalin proteins.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of hepatic or pancreatic origin, e.g. neuronal cells. The term also covers so-called "leaky" promoters, which regulate expression of a selected DNA primarily in one tissue, but cause expression in other tissues as well.

As used herein, a "transgenic animal" is any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the vertebrate signalin proteins, e.g. either agonistic or antagonistic forms. However, transgenic animals in which the recombinant signalin gene is silent are also contemplated, as for example, the FLP or CRE recombinase dependent constructs described below. Moreover, "transgenic animal" also includes those recombinant animals in which gene disruption of one or more signalin genes is caused by human intervention, including both recombination and antisense techniques.

The "non-human animals" of the invention include vertebrates such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant is expressed in some but not all cells of the animal. The term "tissue-specific chimeric animal" indicates that one of the recombinant vertebrate signalin genes is present and/or expressed or disrupted in some tissues but not others.

As used herein, the term "transgene" means a nucleic acid sequence (encoding, e.g., one of the vertebrate signalin polypeptides, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a vertebrate signalin polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40 percent identity, though preferably less than 25 percent identity, with one of the vertebrate signalin sequences of the present invention.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject vertebrate signalin polypeptides with a second amino acid sequence defining a domain (e.g. polypeptide portion) foreign to and not substantially homologous with any domain of one of the vertebrate signalin proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-signalin-Y, wherein signalin represents a portion of the protein which is derived from one of the vertebrate signalin proteins, and X and Y are independently absent or represent amino acid sequences which are not related to one of the vertebrate signalin sequences in an organism, including naturally occurring mutants.

As used herein, the terms "transforming growth factor-beta" and "TGFβ" denote a family of structurally related paracrine polypeptides found ubiquitously in vertebrates, and prototypic of a large family of metazoan growth, differentiation, and morphogenesis factors (see, for review, Massaque et al. (1990) Ann Rev Cell Biol 6:597–641; Massaque et al. (1994) Trends Cell Biol 4:172–178; Kingsley (1994) Gene Dev. 8:133–146; and Sporn et al. (1992) J Cell Biol 119:1017–1021). As described in Kingsley, supra, the TGFβ superfamily has at least 25 members, and can be grouped into distinct sub-families with highly related sequences. The most obvious sub-families include the following: the TGFβ sub-family, which comprises at least four genes that are much more similar to TGFβ-1 than to other members of the TGFβ superfamily; the activin sub-family, comprising homo- or hetero-dimers or two sub-units, inhibinβ-A and inhibinβ-B. The decapentaplegic sub-family, which includes the mammalian factors BMP2 and BMP4, which can induce the formation of ectopic bone and cartilage when implanted under the skin or into muscles. The 60A sub-family, which includes a number of mammalian homologs, with osteoinductive activity, including BMP5–8. Other members of the TGFβ superfamily include the gross differentiation factor 1 (GDF-1), GDF-3/VGR-2, dorsalin, nodal, mullerian-inhibiting substance (MIS), and glial-derived neurotrophic growth factor (GDNF). It is noted that the DPP and 60A sub-families are related more closely to one another than to other members of the TGFβ superfamily, and have often been grouped together as part of a larger collection of molecules called DVR (dpp and vg1 related). Unless evidenced from the context in which it is used, the term TGFβ as used throughout this specification will be understood to generally refer to members of the TGFβ superfamily as appropriate. Reference to members of the TGF β sub-family will be explicit, or evidenced from the context in which the term TGFβ is used.

The term "isolated" as also used herein with respect to nucleic acids, such as DNA or RNA, refers to molecules separated from other DNAs, or RNAs, respectively, that are present in the natural source of the macromolecule. For example, an isolated nucleic acid encoding one of the subject vertebrate signalin polypeptides preferably includes no more than 10 kilobases (kb) of nucleic acid sequence which naturally immediately flanks the vertebrate signalin gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As described below, one aspect of the invention pertains to isolated nucleic acids comprising nucleotide sequences encoding vertebrate signalin polypeptides, and/or equivalents of such nucleic acids. The term nucleic acid as used herein is intended to include fragments as equivalents. The term equivalent is understood to include nucleotide sequences encoding functionally equivalent signalin polypeptides or functionally equivalent peptides having an activity of a vertebrate signalin protein such as described herein. Equivalent nucleotide sequences will include sequences that differ by one or more nucleotide substitutions, additions or deletions, such as allelic variants; and will, therefore, include sequences that differ from the nucleotide sequence of the vertebrate signalin cDNA sequences shown in any of SEQ ID Nos:1–13 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to the nucleotide sequences represented in one or more of SEQ ID Nos:1–13. In one embodiment, equivalents will further include nucleic acid sequences derived from and evolutionarily related to, a nucleotide sequences shown in any of SEQ ID Nos:1–13.

Moreover, it will be generally appreciated that, under certain circumstances, it may be advantageous to provide homologs of one of the subject signalin polypeptides which function in a limited capacity as one of either a signalin agonist (mimetic) or a signalin antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of signalin proteins.

Homologs of each of the subject signalin proteins can be generated by mutagenesis, such as by discrete point mutation(s), or by truncation. For instance, mutation can give rise to homologs which retain substantially the same, or merely a subset, of the biological activity of the signalin polypeptide from which it was derived. Alternatively, antagonistic forms of the protein can be generated which are able to inhibit the function of the naturally occurring form of the protein, such as by competitively binding to a downstream or upstream member of the signaling cascade which includes the signalin protein. In addition, agonistic forms of the protein may be generated which are constituatively active. Thus, the vertebrate signalin protein and homologs thereof provided by the subject invention may be either positive or negative regulators of signal transduction by TGFβ's.

In general, polypeptides referred to herein as having an activity (e.g., are "bioactive") of a vertebrate signalin protein are defined as polypeptides which include an amino acid sequence corresponding (e.g., identical or homologous) to all or a portion of the amino acid sequences of a vertebrate signalin proteins shown in any one or more of SEQ ID Nos:14–26 and which mimic or antagonize all or a portion of the biological/biochemical activities of a naturally occurring signalin protein. Examples of such biological activity include the ability to induce (or otherwise modulate) formation and differentiation of mesodermal or ectodermal tissue of developing vertebrate embryos. The subject polypeptides can be characterized, therefore, by an ability to induce and/or maintain differentiation or survival of stem cells or germ cells, including cells derived from chordamesoderm, dorsal (araxial) mesoderm, intermediate mesoderm, lateral mesoderm, head mesenchyme, epithelial cells, neural tube or neural crest derived cells, and the like. Signalin proteins of the present invention can also have biological activities which include an ability to regulate organogensis, such as through the ability to influence limb patterning, by, for example, skeletogenic activity. Alternatively, signalins can be characterized by their ability to induce or inhibit the proliferation of such cells as fibroblasts and cells of the immune system. Additional effects of signalins may be seen on tissue maintenance and repair post-development, such as bone repair or wound healing. The biological activity associated with signalin proteins of the present invention can also include the ability to modulate sexual maturity or reproduction, including functioning in regression of Mullerian ducts, modulating lactation or the production of follicle stimulating hormone, and spermatogenesis.

The bioactivity of the subject signalin proteins may also include the ability to alter the transcriptional rate of a gene, such as by participating in the transcriptional complexes (activating or inhibiting), e.g., either homo- or hetero-oligomeric in composition, or by altering the composition of a transcriptional complex by modfiying the competency and/or availability of proteins of the complex. The signalin gene products may also be involved in regulating post-translational modification of other cellular proteins, e.g., by action of an intrinsic enzymatic activity, or as a regulatory subunit of an enzyme complex, and/or as a chaperon.

Other biological activities of the subject signalin proteins are described herein or will be reasonably apparent to those skilled in the art. According to the present invention, a polypeptide has biological activity if it is a specific agonist or antagonist of a naturally-occurring form of a vertebrate signalin protein.

Preferred nucleic acids encode a vertebrate α-signalin polypeptide comprising an amino acid sequence at least 60% homologous, more preferably 70% homologous and most preferably 80% homologous with an amino acid sequence of a human or xenopus α-signalin, e.g., such as selected from the group consisting of SEQ ID Nos: 14, 16, 18, 20 and 24. Nucleic acids which encode polypeptides at least about 90%, more preferably at least about 95%, and most preferably at least about 98–99% homology with an amino acid sequence represented in one of SEQ ID Nos: 14, 16, 18, 20 and 24 are or course also within the scope of the invention. In one embodiment, the nucleic acid is a cDNA encoding a peptide having at least one activity of the subject vertebrate signalin polypeptide. Preferably, the nucleic acid includes all or a portion of the nucleotide sequence corresponding to the coding region of SEQ ID Nos: 1, 3, 5, 7 or 11.

In certain preferred embodiments, the invention features a purified or recombinant signalin polypeptide having a molecular weight in the range of 45 kd to 70 kd. For instance, preferred signalin polypeptide chains of the α and β subfamilies have molecular weights in the range of 45 kd to about 55 kd, even more preferably in the range of 50–55 kd. In another illustrative example, preferred signalin polypeptide chains of the γ subfamily have molecular weights in the range of 60 kd to about 70 kd, even more preferably in the range of 63–68 kd. It will be understood that certain post-translational modifications, e.g., phosphorylation and the like, can increase the apparent molecular weight of the signalin protein relative to the unmodified polypeptide chain.

In other embodiments, preferred nucleic acids encode a bioactive fragment of a vertebrate β- or γ-signalin polypeptides comprising an amino acid sequence at least 50% homologous, more preferably 60% homologous, more preferably 70% homologous and most preferably 80% homologous with an amino acid sequence of a human or xenopus β- or γ-signalin, e.g., such as selected from the group consisting of SEQ ID Nos: 15, 17, 19, 21, 22 and 23. Nucleic acids which encode polypeptides at least about 90%, more preferably at least about 95%, and most preferably at least about 98–99% homologous, or identical, with an amino acid sequence represented in one of SEQ ID Nos: 15, 17, 19, 21, 22 and 23 are also within the scope of the invention.

Still other preferred nucleic acids of the present invention encode an α-signalin polypeptide which includes a polypeptide sequence corresponding to all or a portion of amino acid residues 225–300 of SEQ ID No:14 or 230–301 of SEQ ID No. 16, e.g., at least 5, 10, 25, or 50 amino acid residues of that region. Likewise, preferred nucleic acids which encode a γ-signalin polypeptide include sequences for a polypeptide sequence corresponding to all or a portion of amino acid residues 186–304 of SEQ ID No. 15. Even more preferred nucleic acids encode γ-signalin polypeptides which include an amino acid sequence corresponding to all or a portion of the polypeptide sequence from 262–304 of SEQ ID No. 15. In yet another preferred embodiment, the signalin nucleic acids encode a β-signalin polypeptide sequence including a polypeptide sequence corresponding to all or a portion of amino acid residues 170–332 of SEQ ID No:17. Even more preferred nucleic acids encode β-signalin polypeptides which include an amino acid sequence corresponding to all or a portion of the polypeptide sequence from 260–332 of SEQ ID No. 17.

Another aspect of the invention provides a nucleic acid which hybridizes under high or low stringency conditions to a nucleic acid represented by one of SEQ ID Nos:1–13. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids, having a sequence that differs from the nucleotide sequences shown in one of SEQ ID Nos:1–13 due to degeneracy in the genetic code are also within the scope of the invention. Such nucleic acids encode functionally equivalent peptides (i.e., a peptide having a biological activity of a vertebrate signalin polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a vertebrate signalin polypeptide. However, it is expected that DNA sequence polymorphisms that do lead to changes in the amino acid sequences of the subject signalin polypeptides will exist among vertebrates. One skilled in the art will appreciate that these variations in one or more nucleotides (up to about 3–5% of the nucleotides) of the nucleic acids encoding polypeptides having an activity of a vertebrate signalin polypeptide may exist among individuals of a given species due to natural allelic variation.

As used herein, a signalin gene fragment refers to a nucleic acid having fewer nucleotides than the nucleotide sequence encoding the entire mature form of a vertebrate signalin protein yet which (preferably) encodes a polypeptide which retains some biological activity of the full length protein. Fragment sizes contemplated by the present invention include, for example, 5, 10, 25, 50, 75, 100, or 200 amino acids in length.

As indicated by the examples set out below, signalin protein-encoding nucleic acids can be obtained from mRNA present in any of a number of eukaryotic cells. It should also be possible to obtain nucleic acids encoding vertebrate signalin polypeptides of the present invention from genomic DNA from both adults and embryos. For example, a gene encoding a signalin protein can be cloned from either a cDNA or a genomic library in accordance with protocols described herein, as well as those generally known to persons skilled in the art. A cDNA encoding a signalin protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding a vertebrate signalin protein can also be cloned using established polymerase chain reaction techniques in accordance with the nucleotide sequence information provided by the invention. The nucleic acid of the invention can be DNA or RNA. A preferred nucleic acid is a cDNA represented by a sequence selected from the group consisting of SEQ ID Nos:1–13.

Another aspect of the invention relates to the use of the isolated nucleic acid in "antisense" therapy. As used herein, "antisense" therapy refers to administration or in situ generation of oligonucleotide probes or their derivatives which specifically hybridize (e.g. binds) under cellular conditions, with the cellular mRNA and/or genomic DNA encoding one or more of the subject signalin proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a vertebrate signalin protein. Alternatively, the antisense construct is an oligonucleotide probe which is generated ex vivo and which, when introduced into the cell causes inhibition of expression by hybridizing with the mRNA and/or genomic sequences of a vertebrate signalin gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Accordingly, the modified oligomers of the invention are useful in therapeutic, diagnostic, and research contexts. In therapeutic applications, the oligomers are utilized in a manner appropriate for antisense therapy in general. For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

In addition to use in therapy, the oligomers of the invention may be used as diagnostic reagents to detect the presence or absence of the target DNA or RNA sequences to which they specifically bind. Such diagnostic tests are described in further detail below.

Likewise, the antisense constructs of the present invention, by antagonizing the normal biological activity of one of the signalin proteins, can be used in the manipulation of tissue, e.g. tissue differentiation, both in vivo and for ex vivo tissue cultures.

Furthermore, the anti-sense techniques (e.g. microinjection of antisense molecules, or transfection with plasmids whose transcripts are anti-sense with regard to a signalin mRNA or gene sequence) can be used to investigate role of signalin in developmental events, as well as the normal cellular function of signalin in adult tissue. Such techniques can be utilized in cell culture, but can also be used in the creation of transgenic animals.

This invention also provides expression vectors containing a nucleic acid encoding a vertebrate signalin polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject vertebrate signalin proteins. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a DNA sequence when operatively linked to it, may be used in these vectors to express DNA sequences encoding vertebrate signalin polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage 1, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered. In one embodiment, the expression vector includes a recombinant gene encoding a peptide having an agonistic activity of a subject signalin polypeptide, or alternatively, encoding a peptide which is an antagonistic form of the signalin protein. Such expression vectors can be used to transfect cells and thereby produce polypeptides, including fusion proteins, encoded by nucleic acids as described herein.

Moreover, the gene constructs of the present invention can also be used as a part of a gene therapy protocol to deliver nucleic acids encoding either an agonistic or antagonistic form of one of the subject vertebrate signalin proteins. Thus, another aspect of the invention features expression vectors for in vivo or in vitro transfection and expression of a vertebrate signalin polypeptide in particular cell types so as to reconstitute the function of, or alternatively, abrogate the function of signalin-induced signaling in a tissue in which the naturally-occurring form of the protein is misexpressed, or to deliver a form of the protein which alters differentiation of tissue, or which inhibits neoplastic transformation.

Expression constructs of the subject vertebrate signalin polypeptide, and mutants thereof, may be administered in any biologically effective carrier, e.g. any formulation or composition capable of effectively delivering the recombinant gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of signalin expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular signalin polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the subject proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neuronal cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805, van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad Sci. USA* 89:10892–10895; Hwu et al. (1993) *J. Immunol.* 150:4104–4115; U.S. Pat. No. 4,868, 116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083, Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue-or cell-specific transcriptional regulatory sequences which control expression of the signalin gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *Biotechniques* 6:616; Rosenfeld et al. (1991) *Science* 252:431–434; and Rosenfeld et al. (1992) *Cell* 68:143–155.

Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc.*

Natl. Acad. Sci. USA 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, Ed. (Humana, Clifton, N.J., 1991) vol. 7. pp. 109–127). Expression of the inserted signalin gene can be under control of, for example, the E1A promoter, the major late promoter (MLP) and associated leader sequences, the E3 promoter, or exogenously added promoter sequences.

Yet another viral vector system useful for delivery of one of the subject vertebrate signalin genes is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129). It is also one of the few viruses that may integrate its DNA into non-dividing cells, and exhibits a high frequency of stable integration (see for example Flotte et al. (1992) Am. J Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

In addition to viral transfer methods, such as those illustrated above, non-viral methods can also be employed to cause expression of a subject signalin polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject signalin polypeptide gene by the targeted cell. Exemplary gene delivery systems of this type include liposomal derived systems, poly-lysine conjugates, and artificial viral envelopes.

In clinical settings, the gene delivery systems for the therapeutic signalin gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A vertebrate signalin gene, such as any one of the clones represented in the group consisting of SEQ ID NO:1–13, can be delivered in a gene therapy construct by electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Another aspect of the present invention concerns recombinant forms of the signalin proteins. Recombinant polypeptides preferred by the present invention, in addition to native signalin proteins, are at least 60% homologous, more preferably 70% homologous and most preferably 80% homologous with an amino acid sequence represented by any of SEQ ID Nos: 14–26. Polypeptides which possess an activity of a signalin protein (i.e. either agonistic or antagonistic), and which are at least 90%, more preferably at least 95%, and most preferably at least about 98–99% homologous with a sequence selected from the group consisting of SEQ ID Nos: 14–26 are also within the scope of the invention.

The term "recombinant protein" refers to a polypeptide of the present invention which is produced by recombinant DNA techniques, wherein generally, DNA encoding a vertebrate signalin polypeptide is inserted into a suitable expression vector which is in turn used to transform a host cell to produce the heterologous protein. Moreover, the phrase "derived from", with respect to a recombinant signalin gene, is meant to include within the meaning of "recombinant protein" those proteins having an amino acid sequence of a native signalin protein, or an amino acid sequence similar thereto which is generated by mutations including substitutions and deletions (including truncation) of a naturally occurring form of the protein.

The present invention further pertains to recombinant forms of one of the subject signalin polypeptides which are encoded by genes derived from a vertebrate organism, particularly a mammal (e.g. a human), and which have amino acid sequences evolutionarily related to the signalin proteins represented in SEQ ID Nos: 14–26. Such recombinant signalin polypeptides preferably are capable of functioning in one of either role of an agonist or antagonist of at least one biological activity of a wild-type ("authentic") signalin protein of the appended sequence listing. The term "evolutionarily related to", with respect to amino acid sequences of vertebrate signalin proteins, refers to both polypeptides having amino acid sequences which have arisen naturally, and also to mutational variants of vertebrate signalin polypeptides which are derived, for example, by combinatorial mutagenesis. Such evolutionarily derived signalin proteins polypeptides preferred by the present invention are at least 50% homologous, mor preferably 60% homologous, more preferably 70% homologous and most preferably 80% homologous with the amino acid sequence selected from the group consisting of SEQ ID Nos: 14–26. Polypeptides having at least about 90%, more preferably at least about 95%, and most preferably at least about 98–99% homology with a sequence selected from the group consisting of SEQ ID Nos: 14–26 are also within the scope of the invention.

The present invention further pertains to methods of producing the subject signalin polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant signalin polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant signalin polypeptide is a fusion protein containing a domain which facilitates its purification, such as GST fusion protein or poly(His) fusion protein.

This invention also pertains to a host cell transfected to express a recombinant form of the subject signalin polypeptides. The host cell may be any prokaryotic or eukaryotic cell. Thus, a nucleotide sequence derived from the cloning of vertebrate signalin proteins, encoding all or a selected portion of the full-length protein, can be used to produce a recombinant form of a vertebrate signalin polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinase, p53, WT1, PTP phosphotases, SRC, and the like. Similar procedures, or modifications thereof, can be employed to prepare recombinant signalin polypeptides by microbial means or tissue-culture technology in accord with the subject invention.

The recombinant signalin genes can be produced by ligating nucleic acid encoding a signalin protein, or a portion thereof, into a vector suitable for expression in either prokaryotic cells, eukaryotic cells, or both. Expression vectors for production of recombinant forms of the subject signalin polypeptides include plasmids and other vectors. For instance, suitable vectors for the expression of a signalin polypeptide include plasmids of the types: pBR322-derived plasmids, pEMBL-derived plasmids, pEX-derived plasmids, pBTac-derived plasmids and pUC-derived plasmids for expression in prokaryotic cells, such as $E.$ $coli$.

A number of vectors exist for the expression of recombinant proteins in yeast. For instance, YEP24, YIP5, YEP51, YEP52, pYES2, and YRP17 are cloning and expression vehicles useful in the introduction of genetic constructs into $S.$ $cerevisiae$ (see, for example, Broach et al. (1983) in Experimental Manipulation of Gene Expression, ed. M. Inouye Academic Press, p. 83, incorporated by reference herein). These vectors can replicate in $E.$ $coli$ due the presence of the pBR322 ori, and in $S.$ $cerevisiae$ due to the replication determinant of the yeast 2 micron plasmid. In addition, drug resistance markers such as ampicillin can be used. In an illustrative embodiment, a signalin polypeptide is produced recombinantly utilizing an expression vector generated by sub-cloning the coding sequence of one of the signalin genes represented in SEQ ID Nos: 1–13.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the recombinant signalin polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a signalin protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from $E.$ $coli$ (Ben-Bassat et al. (1987) $J.$ $Bacteriol.$ 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing signalin-derived polypeptides in a host which produces MAP (e.g., $E.$ $coli$ or CM89 or $S.$ $cerevisiae$), or in vitro by use of purified MAP (e.g., procedure of Miller et al., supra).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a signalin protein. For example, the VP6 capsid protein of rotavirus can be used as an immunologic carrier protein for portions of the signalin polypeptide, either in the monomeric form or in the form of a viral particle. The nucleic acid sequences corresponding to the portion of a subject signalin protein to which antibodies are to be raised can be incorporated into a fusion gene construct which includes coding sequences for a late vaccinia virus structural protein to produce a set of recombinant viruses expressing fusion proteins comprising signalin epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a signalin protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a signalin polypeptide is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of signalin proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the vertebrate signalin polypeptides of the present invention. For example, signalin polypeptides can be generated as glutathione-S-transferase (GST-fusion) proteins. Such GST-fusion proteins can enable easy purification of the signalin polypeptide, as for example by the use of glutathione-derivatized matrices (see, for example, *Current Protocols in Molecular Biology*, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Signalin polypeptides may also be chemically modified to create signalin derivatives by forming covalent or aggregate conjugates with other chemical moieties, such as glycosyl groups, lipids, phosphate, acetyl groups and the like. Covalent derivatives of signalin proteins can be prepared by linking the chemical moieties to functional groups on amino acid sidechains of the protein or at the N-terminus or at the C-terminus of the polypeptide.

The present invention also makes available isolated signalin polypeptides which are isolated from, or otherwise substantially free of other cellular proteins, especially other signal transduction factors and/or transcription factors which may normally be associated with the signalin polypeptide. The term "substantially free of other cellular proteins" (also referred to herein as "contaminating proteins") or "substantially pure or purified preparations" are defined as encompassing preparations of signalin polypeptides having less than 20% (by dry weight) contaminating protein, and preferably having less than 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified signalin preparations will lack any contaminating proteins from the same animal from that signalin is normally produced, as can be accomplished by recombinant expression of, for example, a human signalin protein in a non-human cell.

As described above for recombinant polypeptides, isolated signalin polypeptides can include all or a portion of an amino acid sequences corresponding to a signalin polypeptide represented in one or more of SEQ ID No:14, SEQ ID No:15, SEQ ID No:16, SEQ ID No:17, SEQ ID No:18, SEQ ID No:19, SEQ ID No:20, SEQ ID No:21, SEQ ID No:22, SEQ ID No:23, SEQ ID No:24, SEQ ID No:25, SEQ ID No:26, homologous sequences thereto.

Isolated peptidyl portions of signalin proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a signalin polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") signalin protein.

The recombinant signalin polypeptides of the present invention also include homologs of the authentic signalin proteins, such as versions of those protein which are resistant to proteolytic cleavage, as for example, due to mutations which alter ubiquitination or other enzymatic targeting associated with the protein.

Modification of the structure of the subject vertebrate signalin polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the signalin polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing= cysteine and methionine. (see, for example, *Biochemistry*, 2nd ed., Ed. by L. Stryer, WH Freeman and Co.: 1981). Whether a change in the amino acid sequence of a peptide results in a functional signalin homolog (e.g. functional in the sense that the resulting polypeptide mimics or antagonizes the wild-type. form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject signalin proteins as well as truncation mutants, and is especially useful for identifying potential variant sequences (e.g. homologs) that are functional in modulating signal transduction from a TGFβ receptor. The purpose of screening such combinatorial libraries is to generate, for example, novel signalin homologs which can act as either agonists or antagonist, or alternatively, possess novel activities all together. To illustrate, signalin homologs can be engineered by the present method to provide selective, constitutive activation of a TGFβ inductive pathway, so as mimic induction by that TGFβ when the signalin homolog is expressed in a cell capable of responding to the TGFβ. Thus, combinatorially-derived homologs can be generated to have an increased potency relative to a naturally occurring form of the protein.

Likewise, signalin homologs can be generated by the present combinatorial approach to selectively inhibit (antagonize) induction by a TGFβ. For instance, mutagenesis can provide signalin homologs which are able to bind other signal pathway proteins (or DNA) yet prevent propagation of the signal, e.g. the homologs can be dominant negative mutants. Moreover, manipulation of certain domains of signalin by the present method can provide domains more suitable for use in fusion proteins.

In one aspect of this method, the amino acid sequences for a population of signalin homologs or other related proteins are aligned, preferably to promote the highest homology possible. Such a population of variants can include, for example, signalin homologs from one or more species. Amino acids which appear at each position of the aligned sequences are selected to create a degenerate set of combinatorial sequences. In a preferred embodiment, the variegated library of signalin variants is generated by combinatorial mutagenesis at the nucleic acid level, and is encoded by a variegated gene library. For instance, a mixture of synthetic oligonucleotides can be enzymatically ligated into gene sequences such that the degenerate set of potential signalin sequences are expressible as individual polypeptides, or alternatively, as a set of larger fusion proteins (e.g. for phage display) containing the set of signalin sequences therein.

As illustrated in FIG. 6, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (*), while insertional mutations in the variant relative to the reference sequence can be disregarded and left out of the sequence of the variant when aligned. For instance, FIG. 6 includes the alignment of the signalin-motif for several of the vertebrate signalin gene products. Analysis of the alignment of this motif from the signalin clones can give rise to the generation of a degenerate library of polypeptides comprising potential signalin sequences.

In an illustrative embodiment, alignment of the signalin-motifs for the Xenopus and human clones can be used to produce a degenerate set of signalin polypeptides including a signalin-motif represented in the general formula:

V-X(1)-X(2)-R-K-G-X(3)-P-H-V-I-Y-X(4)-R-X(5)-W-R-W-P-D-L-X(6)-X(7)-(X8)-X(9)-X(10)-L-K-X(11)-X(12)-X(13)-X(14)-C-X(15)-X(16)-X(17)-F-X(18)-X(19)-K-X(20)-X(21)-X(22)-V (SEQ ID NO:33), wherein each of the degenerate positions "X" can be an amino acid which occurs in that position in one of the human or Xenopus clones. For instance, Xaa(1) represents Ser, Pro, or Ala; Xaa(2) represents His or Gly; Xaa(3) represents Leu, or Phe; Xaa(4) represents Cys or Ala; Xaa(5) represents Val or Leu; Xaa(6) represents His or Gln; Xaa(7) represents Ser or an amino acid gap; Xaa(8) represents His or Lys; Xaa(9) represents His or Asn; Xaa(10) represents Glu or Gly; Xaa(11) represents Pro, Ala, or His; Xaa(12) represents Leu, Ile, Val or Met; Xaa(13) represents Lys or Glu; Xaa(14) represents Cys, Asn, or Phe; Xaa (15) represents Glu or Gln; Xaa(16) represents Tyr, Phe, or Leu; Xaa(17) represents Pro or Ala; Xaa(18) represents Glu, Asn, Val, or Asp; Xaa(19) represents Ser or Leu; Xaa(20) represents Gln, Lys, or Tyr; Xaa(21) represents Lys or Asp; Xaa(22) represent Glu or Asp. In a more expansive library, each degenerate position X can be selected from any amino acid which is a conservative substituition with those amino acid resideues occurring in the Xenopus and human clones, e.g. conserved isoelectronically or by polarity. In an even more expansive library, each X can be selected from any amino acid.

There are many ways by which such libraries of potential signalin homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential signalin sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249;386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Likewise, a library of coding sequence fragments can be provided for a signalin clone in order to generate a variegated population of signalin fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a signalin coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of signalin homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate signalin sequences created by combinatorial mutagenesis techniques.

In one embodiment, embryonic stem cells (ES) can be exploited to analyze the variegated signalin library. For instance, the library of expression vectors can be transfected into an ES cell line ordinarily responsive to a particular TGFβ. The transfected cells are then contacted with the TGFβ and the effect of the signalin mutant on induction of phenotypic markers by the paracrine factor can be detected, e.g. by FACS. Plasmid DNA can then be recovered from the cells which score for inhibition, or alternatively, potentiation of TGFβ induction, and the individual clones further characterized. Other cell lines can be substituted for the ES cells, from even more primitive animal cap cells, to embryonic carcinoma cells, to cells from mature, differentiated tissue, e.g. chondrocytes or osteocytes.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevir Publishing Co., Amsterdam, pp. 401–410; Delgrave et al., 1993, *Protein Engineering* 6(3):327–33 1).

The invention also provides for reduction of the vertebrate signalin proteins to generate mimetics, e.g. peptide or non-peptide agents, which are able to disrupt binding of a vertebrate signalin polypeptide of the present invention with either upstream or downstream components of its signaling cascade. Thus, such mutagenic techniques as described above are also useful to map the determinants of the signalin proteins which participate in protein-protein interactions involved in, for example, binding of the subject vertebrate signalin polypeptide to proteins which may function upstream (including both activators and repressors of its activity) or to proteins or nucleic acids which may function downstream of the signalin polypeptide, whether they are positively or negatively regulated by it. To illustrate, the critical residues of a subject signalin polypeptide which are involved in molecular recognition of an upstream or downstream signalin component can be determined and used to generate signalin-derived peptidomimetics which competitively inhibit binding of the authentic signalin protein with that moiety. By employing, for example, scanning mutagenesis to map the amino acid residues of each of the subject signalin proteins which are involved in binding other extracellular proteins, peptidomimetic compounds can be generated which mimic those residues of the signalin protein which facilitate the interaction. Such mimetics may then be used to interfere with the normal function of a signalin protein. For instance, non-hydrolyzable peptide analogs of such residues can be generated using benzodiazepine (e.g., see Preidinger et al. in *Peptides. Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134.71).

Another aspect of the invention pertains to an antibody specifically reactive with a vertebrate signalin protein. For example, by using immunogens derived from a signalin protein, e.g. based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a vertebrate signalin polypeptide or an antigenic fragment which is capable of eliciting an antibody response). Techniques for conferring immunogenicity on a protein or peptide include conjugation to carriers or other techniques well known in the art. An immunogenic portion of a signalin protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a signalin protein of a vertebrate organism, such as a mammal, e.g. antigenic determinants of a protein represented by SEQ ID Nos:14–26 or closely related homologs (e.g. at least 85% homologous, preferably at least 90% homologous, and more preferably at least 95% homologous). In yet a further preferred embodiment of the present invention, in order to provide, for example, antibodies which are immuno-selective for discrete signalin homologs, e.g. hu-signalin1 or hu-signalin2, the anti-signalin polypeptide antibodies do not substantially cross react (i.e. does not react specifically) with a protein which is, for example, less than 85%, 90% or 95% homologous with the selected signalin. By "not substantially cross react", it is meant that the antibody has a binding affinity for a non-homologous protein which is at least one order of magnitude, more preferably at least 2 orders of magnitude, and even more preferably at least 3 orders of magnitude less than the binding affinity of the antibody for the intended target signalin.

Following immunization of an animal with an antigenic preparation of a signalin polypeptide, anti-signalin antisera can be obtained and, if desired, polyclonal anti-signalin antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a vertebrate signalin polypeptide of the present invention and monoclonal antibodies isolated from a culture comprising such hybridoma cells.

The term antibody as used herein is intended to include fragments thereof which are also specifically reactive with one of the subject vertebrate signalin polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a signalin protein conferred by at least one CDR region of the antibody.

Both monoclonal and polyclonal antibodies (Ab) directed against authentic signalin polypeptides, or signalin variants, and antibody fragments such as Fab and $F(ab)_2$, can be used to block the action of one or more signalin proteins and allow the study of the role of these proteins in, for example, embryogenesis and/or maintenance of differential tissue. For example, purified monoclonal Abs can be injected directly into the limb buds of chick or mouse embryos. In a similar approach, hybridomas producing anti-signalin monoclonal Abs, or biodegradable gels in which anti-signalin Abs are suspended, can be implanted at a site proximal or within the area at which signalin action is intended to be blocked. Experiments of this nature can aid in deciphering the role of this and other factors that may be involved in limb patterning and tissue formation.

Antibodies which specifically bind signalin epitopes can also be used in immunohistochemical staining of tissue samples in order to evaluate the abundance and pattern of expression of each of the subject signalin polypeptides. Anti-signalin antibodies can be used diagnostically in immuno-precipitation and immuno-blotting to detect and evaluate signalin protein levels in tissue as part of a clinical testing procedure. For instance, such measurements can be useful in predictive valuations of the onset or progression of skeletogenic disorders. Likewise, the ability to monitor signalin protein levels in an individual can allow determination of the efficacy of a given treatment regimen for an individual afflicted with such a disorder. The level of signalin polypeptides may be measured from cells in bodily fluid, such as in samples of cerebral spinal fluid or amniotic fluid, or can be measured in tissue, such as produced by biopsy. Diagnostic assays using anti-signalin antibodies can include, for example, immunoassays designed to aid in early diagnosis of a degenerative disorder, particularly ones which are manifest at birth. Diagnostic assays using anti-signalin polypeptide antibodies can also include immunoassays designed to aid in early diagnosis and phenotyping neoplastic or hyperplastic disorders.

Another application of anti-signalin antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a signalin protein, e.g. other orthologs of a particular signalin protein or other paralogs from the same species, can then be detected with antibodies, as, for example, reacting nitrocellulose filters lifted from infected plates with anti-signalin antibodies. Positive phage detected by this assay can then be isolated from the infected plate. Thus, the presence of signalin homologs can be detected and cloned from other animals, as can alternate isoforms (including splicing variants) from humans.

Moreover, the nucleotide sequences determined from the cloning of signalin genes from vertebrate organisms will further allow for the generation of probes and primers designed for use in identifying and/or cloning signalin homologs in other cell types, e.g. from other tissues, as well as signalin homologs from other vertebrate organisms. For instance, the present invention also provides a probe/primer comprising a substantially purified oligonucleotide, which oligonucleotide comprises a region of nucleotide sequence that hybridizes under stringent conditions to at least 10 consecutive nucleotides of sense or anti-sense sequence selected from the group consisting of SEQ ID No:1, SEQ ID No:2, SEQ ID No:3, SEQ ID No:4, SEQ ID No:5, SEQ ID No:6, SEQ ID No:7, SEQ ID No:8, SEQ ID No:9, SEQ ID No:10, SEQ ID No:11, SEQ ID No:12, SEQ ID No:13, or naturally occurring mutants thereof. For instance, primers based on the nucleic acid represented in SEQ ID Nos:1–13 can be used in PCR reactions to clone signalin homologs. Likewise, probes based on the subject signalin sequences can be used to detect transcripts or genomic sequences encoding the same or homologous proteins. In preferred embodiments, the probe further comprises a label group attached thereto and able to be detected, e.g. the label group is selected from amongst radioisotopes, fluorescent compounds, enzymes, and enzyme co-factors.

Such probes can also be used as a part of a diagnostic test kit for identifying cells or tissue which misexpress a signalin protein, such as by measuring a level of a signalin-encoding nucleic acid in a sample of cells from a patient; e.g. detecting signalin mRNA levels or determining whether a genomic signalin gene has been mutated or deleted.

To illustrate, nucleotide probes can be generated from the subject signalin genes which facilitate histological screening of intact tissue and tissue samples for the presence (or absence) of signalin-encoding transcripts. Similar to the diagnostic uses of anti-signalin antibodies, the use of probes directed to signalin messages, or to genomic signalin sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with immunoassays as described above, the oligonucleotide probes can help facilitate the determination of the molecular basis for a developmental disorder which may involve some abnormality associated with expression (or lack thereof) of a signalin protein. For instance, variation in polypeptide synthesis can be differentiated from a mutation in a coding sequence.

Accordingly, the present method provides a method for determining if a subject is at risk for a disorder characterized by aberrant cell proliferation and/or differentiation. In preferred embodiments, method can be generally characterized as comprising detecting, in a sample of cells from the subject, the presence or absence of a genetic lesion characterized by at least one of (i) an alteration affecting the integrity of a gene encoding a signalin-protein, or (ii) the mis-expression of the signalin gene. To illustrate, such genetic lesions can be detected by ascertaining the existence of at least one of (i) a deletion of one or more nucleotides from a signalin gene, (ii) an addition of one or more nucleotides to a signalin gene, (iii) a substitution of one or more nucleotides of a signalin gene, (iv) a gross chromosomal rearrangement of a signalin gene, (v) a gross alteration in the level of a messenger RNA transcript of a signalin gene, (vii) aberrant modification of a signalin gene, such as of the methylation pattern of the genomic DNA, (vii) the presence of a non-wild type splicing pattern of a messenger RNA transcript of a signalin gene, (viii) a non-wild type level of a signalin-protein, and (ix) inappropriate post-translational modification of a signalin-protein. As set out below, the present invention provides a large number of assay techniques for detecting lesions in a signalin gene, and importantly, provides the ability to discern between different molecular causes underlying signalin-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a signalin gene, such as represented by any of SEQ ID Nos: 1–13, or naturally occurring mutants thereof, or 5' or 3' flanking sequences or intronic sequences naturally associated with the subject signalin genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1944) *PNAS* 91:360–364), the later of which can be particularly useful for detecting point mutations in the signalin gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a signalin gene under conditions such that hybridization and amplification of the signalin gene (if present) occurs, and (iv) detecting the presence or absence of an amplification product, or detecting the size of the amplification product and comparing the length to a control sample.

In still another embodiment, the level of a signalin-protein can be detected by immunoassay. For instance, the cells of a biopsy sample can be lysed, and the level of a signalin-protein present in the cell can be quantitated by standard immunoassay techniques. In yet another exemplary embodiment, aberrant methylation patterns of a signalin gene can be detected by digesting genomic DNA from a patient sample with one or more restriction endonucleases that are sensitive to methylation and for which recognition sites exist in the signalin gene (including in the flanking and intronic sequences). See, for example, Buiting et al. (1994) *Human Mol Genet* 3:893–895. Digested DNA is separated by gel electrophoresis, and hybridized with probes derived from, for example, genomic or cDNA sequences. The methylation status of the signalin gene can be determined by comparison of the restriction pattern generated from the sample DNA with that for a standard of known methylation.

In yet another aspect of the invention, the subject signalin polypeptides can be used to generate a "two hybrid" assay or an "interaction trap" assay (see, for example, U.S. Pat. No. 5,283,317; Zervos et al. (1993) *Cell* 72:223–232; Madura et al. (1993) J Biol Chem 268:12046–12054; Bartel et al. (1993) Biotechniques 14:920–924; Iwabuchi et al. (1993) Oncogene 8:1693–1696; and Brent WO94/10300), for isolating coding sequences for other cellular proteins which bind signalins ("signalin-binding proteins" or "signalin-bp"). Such signalin-binding proteins would likely be involved in the propagation of TGFβ signals by the signalin proteins as, for example, the upstream or downstream elements of the signaling pathway or as collateral regulators of signal bioactivity.

Briefly, the interaction trap relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a signalin polypeptide. The second hybrid protein encodes a transcriptional activation domain fused in frame to a sample gene from a cDNA library. If the bait and sample hybrid proteins are able to interact, e.g., form a signalin-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the signalin and sample proteins.

Furthermore, by making available purified and recombinant signalin polypeptides, the present invention facilitates the development of assays which can be used to screen for drugs, including signalin homologs, which are either agonists or antagonists of the normal cellular function of the subject signalin polypeptides, or of their role in the pathogenesis of cellular differentiation and/or proliferation and disorders related thereto. In one embodiment, the assay evaluates the ability of a compound to modulate binding between a signalin polypeptide and a molecule, be it protein or DNA, that interacts either upstream or downstream of the signalin polypeptide in the TGFβ signaling pathway. A variety of assay formats will suffice and, in light of the present inventions, will be comprehended by a skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with proteins which may function upstream (including both activators and repressors of its activity) or to proteins or nucleic acids which may function downstream of the signalin polypeptide, whether they are positively or negatively regulated by it. To the mixture of the compound and the upstream or downstream element is then added a composition containing a signalin polypeptide. Detection and quantification of complexes of signalin with it's upstream or downstream elements provide a means for determining a compound's efficacy at inhibiting (or potentiating) complex formation between signalin and the signalin-binding elements. The efficacy of the compound can be assessed by generating dose response curves from data obtained using various concentrations of the test compound. Moreover, a control assay can also be performed to provide a baseline for comparison. In the control assay, isolated and purified signalin polypeptide is added to a composition containing the signalin-binding element, and the formation of a complex is quantitated in the absence of the test compound.

Complex formation between the signalin polypeptide and a signalin binding element may be detected by a variety of techniques. Modulation of the formation of complexes can be quantitated using, for example, detectably labeled proteins such as radiolabeled, fluorescently labeled, or enzymatically labeled signalin polypeptides, by immunoassay, or by chromatographic detection.

Typically, it will be desirable to immobilize either signalin or its binding protein to facilitate separation of complexes from uncomplexed forms of one or both of the proteins, as well as to accommodate automation of the assay. Binding of signalin to an upstream or downstream element, in the presence and absence of a candidate agent, can be accomplished in any vessel suitable for containing the reactants. Examples include microtitre plates, test tubes, and microcentrifuge tubes. In one embodiment, a fusion protein can be provided which adds a domain that allows the protein to be bound to a matrix. For example, glutathione-S-transferase/signalin (GST/signalin) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stingent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of signalin-binding protein found in the bead fraction quantitated from the gel using standard electrophoretic techniques such as described in the appended examples.

Other techniques for immobilizing proteins on matrices are also available for use in the subject assay. For instance, either signalin or its cognate binding protein can be immobilized utilizing conjugation of biotin and streptavidin. For instance, biotinylated signalin molecules can be prepared from biotin-NHS (N-hydroxy-succinimide) using techniques well known in the art (e.g., biotinylation kit, Pierce Chemicals, Rockford, Ill.), and immobilized in the wells of streptavidn-coated 96 well plates (Pierce Chemical). Alternatively, antibodies reactive with signalin but which do not interfere with binding of upstream or downstream elements can be derivatized to the wells of the plate, and signalin trapped in the wells by antibody conjugation. As above, preparations of a signalin-BP and a test compound are incubated in the signalin-presenting wells of the plate, and the amount of complex trapped in the well can be quantitated. Exemplary methods for detecting such complexes, in addition to those described above for the GST-immobilized complexes, include immunodetection of complexes using antibodies reactive with the signalin binding element, or which are reactive with signalin protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the signalin-BP. To illustrate, the signalin-BP can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-signalin antibodies, can be used. Alternatively, the protein to be detected in the complex can be "epitope tagged" in the form of a fusion protein which includes, in addition to the signalin sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

In addition to cell-free assays, such as described above, the readily available source of vertebrate signalin proteins provided by the present invention also facilitates the generation of cell-based assays for identifying small molecule agonists/antagonists and the like. Cells which are sensitive to signalin-mediated induction by a TGFβ can be caused to overexpress a recombinant signalin protein in the presence and absence of a test agent of interest, with the assay scoring for modulation in signalin inductive responses by the target cell mediated by the test agent. As with the cell-free assays, agents which produce a statistically significant change in signalin-dependent induction (either inhibition or potentiation) can be identified. In an illustrative embodiment, embryos or ES cells are caused to ectopically express a signalin polypeptide and the effects of compounds of interest on tissue pattern induction are measured.

For example, as described in the appended examples, overexpression of signalins in embryonic cells can cause constitutive induction of differentiation in an apparently similar fashion to induction mediated by different TGFβ factors. Accordingly, such recombinant cells can be used to identify inhibitors of particular TGFβ factors by the compound's ability to inhibit signal transduction events downstream of the signalin protein. To illustrate, the recombinant xe-signalin 1 animal caps of Example 2 can be contacted with a panel of test compounds, and inhibitors scored by the ability to inhibit conversion of the ectodermal cells to a ventral mesoderm fate (such as may be detected by use of phenotype markers). Compounds which cause a statistically significant decrease in ventral mesoderm induction can be selected for further testing. This assay can be further simplified by scoring for expression of genes which are up- or down-regulated in response to a signalin-dependent signal cascade. In preferred embodiments, the regulatory regions of such genes, e.g., the 5' flanking promoter and enhancer regions, are operably linked to a detectable marker (such as luciferase) which encodes a gene product that can be readily detected.

In another embodiment of a drug screening, a two hybrid assay can be generated with a signalin and signalin-binding protein. Drug dependent inhibition or potentiation of the interaction can be scored.

In the event that the signalin proteins themselves, or in complexes with other proteins, are capable of binding DNA and modifying transcription of a gene, a transcriptional based assay using, for example, the signalin responsive regulatory sequences operably linked to a detectable marker gene.

Furthermore, each of the assay systems set out above can be generated in a "differential" format. That is, the assay format can provide information regarding specificity as well as potency. For instance, side-by-side comparison of a test compound's effect on different signalins can provide information on selectivity, and permit the identification of compounds which selectively modulate the bioactivity of only a subset of the signalin family.

Another aspect of the present invention relates to a method of inducing and/or maintaining a differentiated state, enhancing survival, and/or promoting (or alternatively inhibiting) proliferation of a cell responsive to a TGF-β factor, by contacting the cells with an agent which modulates signalin-dependent signaling by the growth factor. For instance, it is contemplated by the invention that, in light of the present finding of an apparently broad involvement of signalin proteins in the formation of ordered spatial arrangements of differentiated tissues in vertebrates, the subject method could be used to generate and/or maintain an array of different vertebrate tissue both in vitro and in vivo. A "signalin therapeutic," whether inductive or anti-inductive with respect to signaling by a TGF-β, can be, as appropriate, any of the preparations described above, including isolated polypeptides, gene therapy constructs, antisense molecules, peptidomimetics or agents identified in the drug assays provided herein. Moreover, it is contemplated that, based on the observation of activity of the vertebrate signalin proteins in drosophila, signalin therapeutics, for purposes of therapeutic and diagnostic uses, may include the Drosophila and C. elegans MAD proteins and homologs thereof.

There are a wide variety of pathological cell proliferative conditions for which signalin therapeutics of the present invention can be used in treatment. For instance, such agents can provide therapeutic benefits where the general strategy being the inhibition of an anomalous cell proliferation. Diseases that might benefit from this methodology include, but are not limited to various cancers and leukemias, psoriasis, bone diseases, fibroproliferative disorders such as involving connective tissues, atherosclerosis and other smooth muscle proliferative disorders, as well as chronic inflammation.

In addition to proliferative disorders, the present invention contemplates the use of signalin therapeutics for the treatment of differentiative disorders which result from, for example, de-differentiation of tissue which may (optionally) be accompanied by abortive reentry into mitosis, e.g. apoptosis. Such degenerative disorders include chronic neurodegenerative diseases of the nervous system, including Alzheimer's disease, Parkinson's disease, Huntington's chorea, amyotrophic lateral sclerosis and the like, as well as spinocerebellar degenerations. Other differentiative disorders include, for example, disorders associated with connective tissue, such as may occur due to de-differentiation of chondrocytes or osteocytes, as well as vascular disorders which involve de-differentiation of endothelial tissue and smooth muscle cells, gastric ulcers characterized by degenerative changes in glandular cells, and renal conditions marked by failure to differentiate, e.g. Wilm's tumors.

It will also be apparent that, by transient use of modulators of signalin pathways, in vivo reformation of tissue can be accomplished, e.g. in the development and maintenance of organs. By controlling the proliferative and differentiative potential for different cells, the subject gene constructs can be used to reform injured tissue, or to improve grafting and morphology of transplanted tissue. For instance, signalin agonists and antagonists can be employed in a differential manner to regulate different stages of organ repair after physical, chemical or pathological insult. For example, such regimens can be utilized in repair of cartilage, increasing bone density, liver repair subsequent to a partial hepatectomy, or to promote regeneration of lung tissue in the treatment of emphysema.

For example, the present method is applicable to cell culture techniques. In vitro neuronal culture systems have proved to be fundamental and indispensable tools for the study of neural development, as well as the identification of trophic and growth factors such as nerve growth factor (NGF), ciliary trophic factors (CNTF), and brain derived neurotrophic factor (BDNF). Once a neuronal cell has become terminally-differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain neuronal cells at various stages of differentiation, and can be employed, for instance, in cell cultures designed to test the specific activities of other trophic factors. In such embodiments of the subject method, the cultured cells can be contacted with an agent which inhibits a signalin-mediated signal otherwise induced by the TGF-β factor activin in order to induce neuronal differentiation (e.g. of a stem cell), or to maintain the integrity of a culture of terminally-differentiated neuronal cells by preventing loss of differentiation. As described in the Melton and Hemmati-Brivanlou PCT application PCT/US94/11745, the default fate of ectodermal tissue is neuronal rather than mesodermal and/or epidermal. In particular, it was discovered that preventing or antagonizing signaling by activin can result in differentiation along a neuronal-fated pathway.

In an exemplary embodiment, the role of the signalin therapeutic in the present method to culture, for example, stem cells, can be to induce differentiation of uncommitted progenitor cells and thereby give rise to a committed progenitor cell, or to cause further restriction of the developmental fate of a committed progenitor cell towards becoming a terminally-differentiated neuronal cell. For example, the present method can be used in vitro to induce and/or maintain the differentiation of neural crest cells into glial cells, schwann cells, chromaffin cells, cholinergic sympathetic or parasympathetic neurons, as well as peptidergic and serotonergic neurons. The signalin therapeutic can be used alone, or can be used in combination with other neurotrophic factors which act to more particularly enhance a particular differentiation fate of the neuronal progenitor cell. In the later instance, a signalin therapeutic might be viewed as ensuring that the treated cell has achieved a particular phenotypic state such that the cell is poised along a certain developmental pathway so as to be properly induced upon contact with a secondary neurotrophic factor. In similar fashion, even relatively undifferentiated stem cells or primitive neuroblasts can be maintained in culture and caused to differentiate by treatment with signalin therapeutics. Exemplry primitive cell cultures comprise cells harvested from the neural plate or neural tube of an embryo even before much overt differentiation has occurred.

Yet another aspect of the present invention concerns the application of signalin therapeutics to modulating morphogenic signals involved in other vertebrate organogenic pathways in addition to neuronal differentiation, e.g., to TGF-β roles in both mesodermal and ectodermal differentiation processes. Thus, it is contemplated by the invention that compositions comprising signalin therapeutics can also be utilized for both cell culture and therapeutic methods involving generation and maintenance of non-neuronal tissue.

In one embodiment, the present invention makes use of the discovery that signalin proteins are likely to be involved in controlling the development and formation of the digestive tract, liver, pancreas, lungs, and other organs which derive from the primitive gut. As described in the Examples below, signalin proteins a presumptively involved in cellular activity in response to TGF-β inductive signals. Accordingly, signalin agonists and/or antagonists can be employed in the development and maintenance of an artificial liver which can have multiple metabolic finctions of a normal liver. In an exemplary embodiment, signalin therapeutics can be used to induce and/or maintain differentiation of digestive tube stem cells to form hepatocyte cultures which can be used to populate extracellular matrices, or which can be encapsulated in biocompatible polymers, to form both implantable and extracorporeal artificial livers.

In another embodiment, compositions of signalin therapeutics can be utilized in conjunction with transplantation of such artificial livers, as well as embryonic liver structures, to promote intraperitoneal implantation, vascularization, and in vivo differentiation and maintenance of the engrafted liver tissue.

Similar utilization of signalin therapeutics are contemplated in the generation and maintenance of pancreatic cultures and artificial pancreatic tissues and organs.

In another embodiment, in vitro cell cultures can be used for the identification, isolation, and study of genes and gene products that are expressed in response to disruption of signalin-mediated signal transduction, and therefore likely involved in development and/or maintenance of tissues. These genes would be "downstream" of the signalin gene products. For example, if new transcription is required for signalin-mediated induction, a subtractive cDNA library prepared with control cells and cells overexpressing a signalin gene can be used to isolate genes that are turned on or turned off by this process. The powerful subtractive library methodology incorporating PCR technology described by Wang and Brown is an example of a methodology useful in conjunction with the present invention to isolate such genes (Wang et al. (1991) Proc. Natl. Acad. Sci. USA 88:11505–11509). For example, this approach has been used successfully to isolate more than sixteen genes involved in tail resorption with and without thyroid hormone treatment in Xenopus. Utilizing control and treated cells, the induced pool can be subtracted from the uninduced pool to isolate genes that are turned on, and then the uninduced pool from the induced pool for genes that are turned off. From this screen, it is expected that two classes of mRNAs can be identified. Class I RNAs would include those RNAs expressed in untreated cells and reduced or eliminated in induced cells, that is the down-regulated population of RNAs. Class II RNAs include RNAs that are upregulated in response to induction and thus more abundant in treated than in untreated cells. RNA extracted from treated vs untreated cells can be used as a primary test for the classification of the clones isolated from the libraries. Clones of each class can be further characterized by sequencing and, their spatiotemporal distribution determined in the embryo by whole mount in situ and developmental northern blots analysis.

In yet another embodiment, signalin therapeutics can be employed to regulate such organs after physical, chemical or pathological insult. For instance, therapeutic compositions comprising signalin therapeutics can be utilized in liver repair subsequent to a partial hepatectomy. Similarly, therapeutic compositions containing signalin therapeutics can be used to promote regeneration of lung tissue in the treatment of emphysema.

In still another embodiment of the present invention, compositions comprising signalin therapeutics can be used for the in vitro generation of skeletal tissue, such as from skeletogenic stem cells, as well as for the in vivo treatment of skeletal tissue deficiencies. The present invention particularly contemplates the use of signalin therapeutics which upregulate or mimic the inductive activity of a bone morphogenetic protein (BMP) or TGF-β, such as may be useful to control chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions, so long as modulation of a TGF-β inductive response is appropriate.

For instance, the present invention makes available effective therapeutic methods and signalin therapeutic compositions for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a signalin therapeutic to generate a cartilage repair response in the connective tissue by stimulating the differentiation and/or proliferation of chondrocytes embedded in the tissue. Induction of chondrocytes by treatment with a signalin therapeutic can subsequently result in the synthesis of new cartilage matrix by the treated cells. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent. The subject method can further be used to prevent the spread of mineralization into fibrotic tissue by maintaining a constant production of new cartilage.

In an illustrative embodiment, the subject method can be used to treat cartilage of a diarthroidal joint, such as a knee, an ankle, an elbow, a hip, a wrist, a knuckle of either a finger or toe, or a temperomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. An injection of a signalin therapeutic into the joint with, for instance, an arthroscopic needle, can be used to treat the afflicted cartilage. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. To date, the growth of new cartilage from either transplantation of autologous or allogenic cartilage has been largely unsuccessful. Problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By promoting chondrogenesis, the subject method can be used to particularly addresses this problem, by causing the implanted cells to become more adaptive to the new environment and effectively resemble hypertrophic chondrocytes of an earlier developmental stage of the tissue. Thus, the action of chondrogensis in the implanted tissue, as provided by the subject method, and the mechanical forces on the actively remodeling tissue can synergize to produce an improved implant more suitable for the new function to which it is to be put.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a signalin therapeutic during the culturing process so as to induce and/or maintain differentiated chondrocytes in the culture in order to further stimulate cartilage matrix production within the implant. In such a manner, the cultured cells can be caused to maintain a phenotype typical of a chondrogenic cell (i.e. hypertrophic), and hence continue the population of the matrix and production of cartilage tissue.

In another embodiment, the implanted device is treated with a signalin therapeutic in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The activation of the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis, as well as inhibits formation of fibrotic tissue proximate the prosthetic device.

In still further embodiments, the subject method can be employed for the generation of bone (osteogenesis) at a site in the animal where such skeletal tissue is deficient. TGF-β's, especially BMPs, are particularly associated with the hypertrophic chondrocytes that are ultimately replaced by osteoblasts as well as the production of bone matrix by osteocytes. Consequently, administration of a signalin therapeutic can be employed as part of a method for treating bone loss in a subject, e.g. to prevent and/or reverse osteoporosis and other osteopenic disorders, as well as to regulate bone growth and maturation. For example, preparations comprising signalin agonists can be employed, for example, to induce endochondral ossification by mimicking or potentiating the activity of a BMP, at least so far as to facilitate the formation of cartilaginous tissue precursors to form the "model" for ossification. Therapeutic compositions of signalin agonists can be supplemented, if required, with other osteoinductive factors, such as bone growth factors (e.g. TGF-β factors, such as the bone morphogenetic factors BMP-2 and BMP-4, as well as activin), and may also include, or be administered in combination with, an inhibitor of bone resorption such as estrogen, bisphosphonate, sodium fluoride, calcitonin, or tamoxifen, or related compounds.

For certain cell-types, particularly in epithelial and hemopoietic cells, normal cell proliferation is marked by responsiveness to negative autocrine or paracrine growth regulators, such as members of the TGFβ family. This is generally accompanied by differentiation of the cell to a post-mitotic phenotype. However, it has been observed that a significant percentage of human cancers derived from these cells types display a reduced responsiveness to growth regulators such as TGFβ. For instance, some tumors of colorectal, liver epithelial, and epidermal origin show reduced sensitivity and resistance to the growth-inhibitory effects of TGFβ as compared to their normal counterparts. In this context, a noteworthy characteristic of several such transformed cell lines is the absence of detectable TGFβ receptors. Treatment of such tumors with signalin therapeutics provides an opportunity to mimic the effective function of TGFβ-mediated inhibition.

To further illustrate the use of the subject method, the therapeutic application of a signalin therapeutic can be used in the treatment of a neuroglioma. Gliomas account for 40–50% of intracranial tumors at all ages of life. Despite the increasing use of radiotherapy, chemotherapy, and sometimes immunotherapy after surgery for malignant glioma, the mortality and morbidity rates have not substantially improved. However, there is increasing experimental and clinical evidence that for a significant number of gliomas, loss of TGFβ responsiveness is an important event in the loss of growth control. Where the cause of decreased responsiveness is due to loss of receptor or loss of other TGFβ signal transduction proteins upstream of a signalin, treatment with a signalin therapeutic can be used effectively to inhibit cell proliferation.

The subject signalin therapeutics can also be used in the treatment of hyperproliferative vascular disorders, e.g. smooth muscle hyperplasia (such as atherosclerosis) or restinosis, as well as other disorders characterized by fibrosis, e.g. rheumatoid arthritis, insulin dependent diabetes mellitus, glomerulonephritis, cirrhosis, and scleroderma, particularly proliferative disorders in which loss of a TGFβ autocrine or paracine signaling is implicated.

For example, restinosis continues to limit the efficacy of coronary angioplasty despite various mechanical and pharmaceutical interventions that have been employed. An important mechanism involved in normal control of intimal proliferation of smooth muscle cells appears to be the induction of autocrine and paracrine TGFβ inhibitory loops in the smooth muscle cells (Scott-Burden et al. (1994) *Tex Heart Inst J* 21:91–97; Graiger et al. (1993) *Cardiovasc Res* 27:2238–2247; and Grainger et al. (1993) *Biochem J* 294:109–112). Loss of sensitivity to TGFβ, or alternatively, the overriding of this inhibitory stimulus such as by PDGF autostimulation, can be a contributory factor to abnormal smooth muscle proliferation in restinosis. It may therefore be possible to treat or prevent restinosis by the use of gene therapy with gene constructs of the present invention which mimic induction by TGFβ. The signalin gene construct can be delivered, for example, by percutaneous transluminal gene transfer (Mazur et al. (1994) *Tex Heart Inst J* 21:104–111) using viral or liposomal delivery compositions. An exemplary adenovirus-mediated gene transfer technique and compositions for treatment of cardiac or vascular smooth muscle is provided in PCT publication WO 94/11506.

TGFβ's also play a significant role in local glomerular and interstitial sites in human kidney development and disease. Consequently, the subject method provides a method of treating or inhibiting glomerulopathies and other renal proliferative disorders comprising the in vivo delivery of a subject signalin therapeutic.

Yet another aspect of the present invention concerns the therapeutic application of a signalin therapeutic to enhance survival of neurons and other neuronal cells in both the central nervous system and the peripheral nervous system. The ability of TGF-β factors to regulate neuronal differentiation during development of the nervous system and also in the adult state indicates that certain of the signalin proteins can be reasonably expected to participate in control of adult neurons with regard to maintenance, functional performance, and aging of normal cells; repair and regeneration processes in chemically or mechanically lesioned cells; and prevention of degeneration and premature death which result from loss of differentiation in certain pathological conditions. In light of this understanding, the present invention specifically contemplates applications of the subject method to the treatment of (prevention and/or reduction of the severity of) neurological conditions deriving from: (i) acute, subacute, or chronic injury to the nervous system, including traumatic injury, chemical injury, vasal injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amylotrophic lateral sclerosis and the like, as well as spinocerebellar degenerations; and (iv) chronic immunological diseases of the nervous system or affecting the nervous system, including multiple sclerosis.

Many neurological disorders are associated with degeneration of discrete populations of neuronal elements and may be treatable with a therapeutic regimen which includes a signalin therapeutic. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalmus or the white matter underlying the cerebral cortex. Here, the cognitive dysfunction results from the isolation of cortical areas by the degeneration of efferents and afferents. Huntington's disease involves the degeneration of intrastraital and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of signalin therapeutics, in order to control, for example, differentiation and apoptotic events which give rise to loss of neurons (e.g. to enhance survival of existing neurons) as well as promote differentiation and repopulation by progenitor cells in the area affected.

In addition to degenerative-induced dementias, a pharmaceutical preparation of one or more of the subject signalin therapeutics can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalmic nucleus, often due to acute vascular accident.

Also included are neurogenic and myopathic diseases which ultimately affect the somatic division of the peripheral nervous system and are manifest as neuromuscular disorders. In an illustrative embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of a signalin therapeutic, can be used alone, or in conjunction with neurotrophic factors such as CNTF, BDNF or NGF to prevent and/or reverse motor neuron degeneration in ALS patients.

Signalin therapeutics can also be used in the treatment of autonomic disorders of the peripheral nervous system, which include disorders affecting the innervation of smooth muscle and endocrine tissue (such as glandular tissue). For instance, the subject method can be used to treat tachycardia or atrial cardiac arrythmias which may arise from a degenerative condition of the nerves innervating the striated muscle of the heart.

In another embodiment, the subject method can be used in the treatment of neoplastic or hyperplastic transformations such as may occur in the central nervous system. For instance, certain of the signalin therapeutics which induce differentiation of neuronal cells by altering responsiveness to a TGF-$\beta$ can be utilized to cause such transformed cells to become either post-mitotic or apoptotic. Treatment with a signalin therapeutic may facilitate disruption of autocrine loops, such as a TGF-$\beta$ autostimulatory loops, which are believed to be involved in the neoplastic transformation of several neuronal tumors. signalin therapeutics may, therefore, be of use in the treatment of, for example, malignant gliomas, medulloblastomas, neuroectodermal tumors, and ependymonas.

Likewise, another aspect of the present invention comprises the inhibition of T cell activation. TGF$\beta$ is known to inhibit T cell proliferation and the signalins described in the present invention could be used to ameliorate diseases that involve chronic inflammation. In addition, TGF$\beta$ has been associated with certain forms of tolerance (Chen et al. (1995) *Nature* 376:177–180) and the present invention could be used to induce T cell tolerance prior to receipt of an allo or xenograft or in cases of allergy or autoimmune disease.

In yet another embodiment, modulation of a signalin-dependent pathway can be used to inhibit spermatogenesis. Spermatogenesis is a process involving mitotic replication of a pool of diploid stem cells, followed by meiosis and terminal differentiation of haploid cells into morphologically and functionally polarized spermatoza. This process exhibits both temporal and spatial regulation, as well as coordinated interaction between the germ and somatic cells. It has been previously shown that the signals mediated by the TGF$\beta$ superfamily, in particular activin, play significant roles in coupling such extracellular stimulus to regulation of mitotic, meiotic events which occur during spermatogenesis (Klaij, et al. (1994) *J. Endocrinol.* 141:131–141).

Likewise, members of the TGF$\beta$ family are important in the regulation of female reproductive organs (Wu, T.C. et al. (1994) *Mol. Reprod. Dev.* 38:9–15). Accordingly, TGF$\beta$ inhibitors, such as signalin antagonists generated in the subject assays, may be useful to prevent oocyte maturation as part of a contraceptive formulation. In other aspects, regulation of induction of meiotic maturation with signalin therapeutics can be used synchronize oocyte populations for in vitro fertilization. Such a protocol can be used to provide a more homogeneous population of oocytes which are healthier and more viable and more prone to cleavage, fertilization and development to blastocyst stage. In addition the signalin therapeutics could be used to treat other disorders of the female reproductive system which lead to infertility including polycysitic ovarian syndrome.

Another aspect of the invention features transgenic non-human animals which express a heterologous signalin gene of the present invention, or which have had one or more genomic signalin genes disrupted in at least one of the tissue or cell-types of the animal. Accordingly, the invention features an animal model for developmental diseases, which animal has signalin allele which is mis-expressed. For example, a mouse can be bred which has one or more signalin alleles deleted or otherwise rendered inactive. Such a mouse model can then be used to study disorders arising from mis-expressed signalin genes, as well as for evaluating potential therapies for similar disorders.

Another aspect of the present invention concerns transgenic animals which are comprised of cells (of that animal) which contain a transgene of the present invention and which preferably (though optionally) express an exogenous signalin protein in one or more cells in the animal. A signalin transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a signalin protein can be essential for many forms of lineage analysis and can additionally provide a means to assess the effects of, for example, lack of signalin expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject signalin proteins. For example, excision of a target sequence which interferes with the expression of a recombinant signalin gene, such as one which encodes an antagonistic homolog or an antisense transcript, can be designed to activate expression of that gene. This interference with expression of the protein can result from a variety of mechanisms, such as spatial separation of the signalin gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant signalin protein can be regulated via control of recombinase expression.

Use of the cre/loxP recombinase system to regulate expression of a recombinant signalin protein requires the construction of a transgenic animal containing transgenes encoding both the Cre recombinase and the subject protein. Animals containing both the Cre recombinage and a recombinant signalin gene can be provided through the construction of "double" transgenic animals. A convenient method for providing such animals is to mate two transgenic animals each containing a transgene, e.g., a signalin gene and recombinase gene.

One advantage derived from initially constructing transgenic animals containing a signalin transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic signalin transgene is silent will allow the study of progeny from that founder in which disruption of signalin mediated induction in a particular tissue or at certain developmental stages would result in, for example, a lethal phenotype.

Similar conditional transgenes can be provided using prokaryotic promoter sequences which require prokaryotic proteins to be simultaneous expressed in order to facilitate expression of the signalin transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a signalin transgene could remain silent into adulthood until "turned on" by the introduction of the trans-activator.

In an exemplary embodiment, the "transgenic non-human animals" of the invention are produced by introducing transgenes into the germline of the non-human animal. Embryonic target cells at various developmental stages can be used to introduce transgenes. Different methods are used depending on the stage of development of the embryonic target cell. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic non-human animal will carry the incorporated transgene. This will in general also be reflected in the efficient transmission of the transgene to offspring of the founder since 50% of the germ cells will harbor the transgene. Microinjection of zygotes is the preferred method for incorporating transgenes in practicing the invention.

Retroviral infection can also be used to introduce signalin transgenes into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

Methods of making signalin knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous signalin gene, such that tissue specific and/or temporal control of inactivation of a signalin allele can be controlled as above.

EXEMPLIFICATION

The invention, now being generally described, will be more readily understood by reference to the following examples, which are included merely for purposes of illustration of certain aspects and embodiments of the present invention and are not intended to limit the invention.

EXAMPLE 1

RT-PCR Cloning of Xenopus Signalin cDNAs

This example describes the methodology used to obtain cDNA clones encoding members of the signalin family of signal transducing molecules. Primers, which are flanked by a BamHI or EcoRI linker, 5' and 3' respectively were generated and used to amplify fragmentd of xenopus signalin cDNAs. The sequence of the upstream primer used in these studies was; CGGGATCCTIGA(T/C)GGI(A/C)GI(T/C)TICA(A/G)(A/G)T (SEQ ID No. 34), and the sequence of the downstream primer used is in these studies was: CGGAATTCTA(A/G)TG(A/G)TAIGG(A/G)TT(T/G/A)AT (A/G)CA (SEQ ID No. 35). The cDNA template used in these studies was derived from Xenopus embryos at stages 2, 11, and 40. PCR was performed under the following conditions: 1 cycle of 93° C., 3 min.; 42° C., 1.5 min.; 72° C., 1 min.; then 4 cycles of 93° C., 1 min.; 42° C., 1.5 min.; 72° C., 1 min.; followed by 30 cycles of 93° C., 1 min.; 55° C., 1.5 min.; 72° C., 1 min.; and finally one cycle of 72° C., 5 min. The PCR fragments were subcloned into pBluescript KSII.

The PCR fragments were sequenced and used as probes to screen a Xenopus oocyte cDNA library. Several clones were isolated from the ooctye library, and were subcloned into pBluescript KSII and then sequenced on both strands.

EXAMPLE 2

RT-PCR Cloning of Human Signalin cDNAs

Utilizing the same PCR primers as described in Example 1, several human signalin clones were isolated. Briefly, using degenerate PCR primers from Example 1, human cDNA samples were amplified by the following PCR conditions: Taq Polymerase in standard buffer 9 µl of 25 mM MgCl per 124 µl reaction; temperature cycling, 95° C. for 3 min, then four cycles of 95° C. for 25 sec, 42° C. for 15 sec then 72° C. for 10 sec, followed by 95° C. for 25 sec, 55° C. for 10 sec, 72° C. for 10 sec, and 73° C. for 10 sec. The resulting cDNA were sequenced by standard protocols.

EXAMPLE 3

Signalins Induce The Formation Of Mesoderm

This Example illustrates that the signalin molecules identified in Example 1 are involved in transducing TGFβ-superfamily signals. As a functional test of the signalins, Xenopus laevis animal pole explants were used. The assay method is illustrated in FIG. 1. Members of the TGFβ superfamily include the bone morphogenetic proteins and activins, among others, and can convert animal pole explants, normally fated to form ectoderm, into two easily distinguished types of mesoderm, dorsal or ventral. To generate mRNA that encodes the signalins, the entire EcoRI fragment of all 4 xenopus signalins were subcloned into the EcoRII site of pSP64TEN. These constructs are called pSP64TEN-signalin 1–4 and for transcription were linearized with XbaI. Synthetic capped mRNA was synthesized using SP6-polymerase. To test the roles of the signalins, the mRNA that encoded the signalins were injected into one-cell embryos. At the blastula stage, animal caps were explanted and cultured until sibling control embryos developed to either stage 11 (gastrula, early) or stage 35 (tadpole, late). After culturing, the explants were examined for morphology, histology, and molecular markers.

Figure 2:
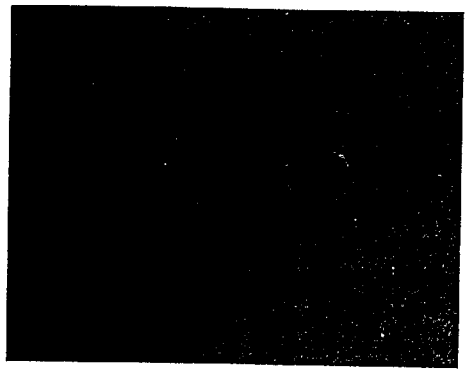
FIG. 2 shows the morphology of animal cap explants from control, signalin1 injected, or signalin2 injected embryos.
Figure 2:
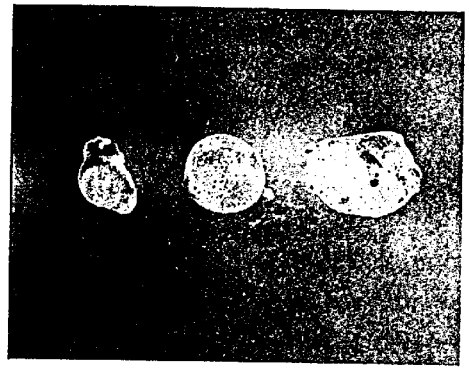
Figure 2:
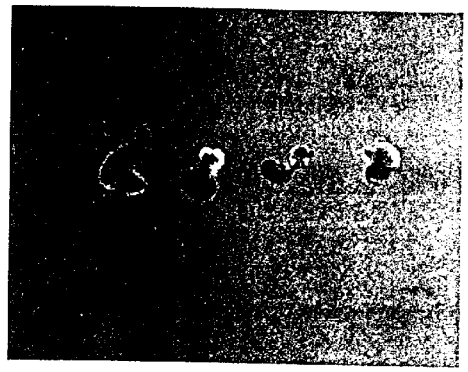
Figure 3:
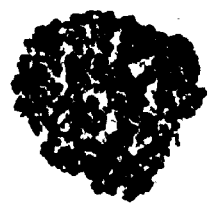
FIG. 3 illustrate the histologic analysis of animal cap explants from control, signalin1 injected, or signalin2 injected embryos.
Figure 3:
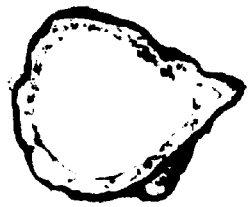
Figure 3:
Figure 4:
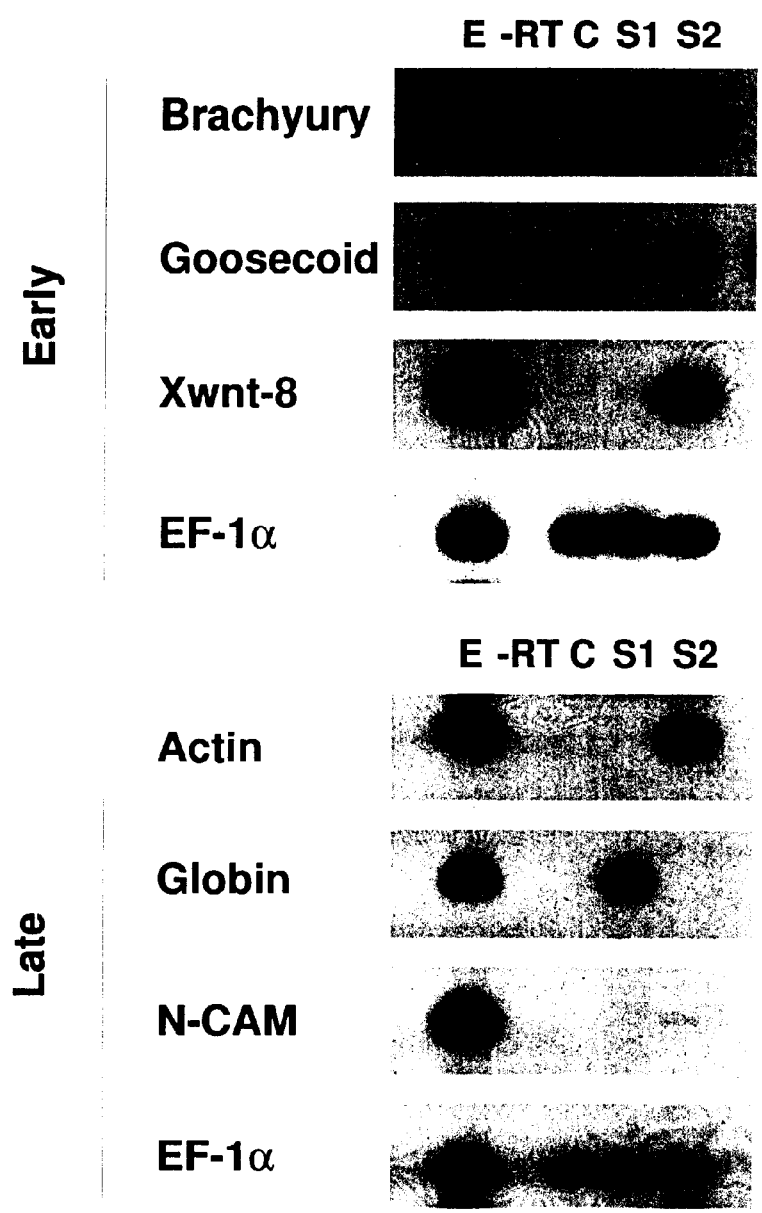
FIG. 4 is an autoradiogram which shows the expression of various marker RNAs in the injected embryos as detected by polymerase chain reaction. Brachyury is a general mesodermal marker; Goosecoid is a marker of dorsal mesoderm; Xwnt-8 is a marker of ventral-lateral mesoderm; globin is a marker of ventral mesoderm; actin is a marker of dorsal mesoderm; NCAM is a marker of neural tissue; and EF-1α is ubiquitously expressed and serves as a control for the amount of RNA included in each reaction. The lane marked "E" contains total RNA harvested from whole embryos and is a positive control. The lane marked "-RT" is identical to the positive control lane, except that reverse transcriptase was not included and serves as a negative control. The lanes designated "S1" and "S2" correspond to samples from embryos injected with xe-signalin 1 and xe-signalin 2, respectively.

As shown in FIGS. 2 and 3, when mRNA that encodes signalin1 is injected into the animal pole, the ectoderm is converted into ventral mesoderm. Signalin1 causes a change in the shape of the animal cap which forms a vesicle, a hallmark of ventral mesoderm. Histology confirms this finding and demonstrates the presence of a vesicle, mesothelium, and mesenchyme as shown in FIG. 3. In addition, the animal cap explants were examined for molecular markers. After injection, animal caps were dissected and cultured until sibling uninjected control embryos developed to either stage 11 (gastrula, early) or stage 35 (tadpole, late) and total RNA was harvested. The RNA was analyzed by RT-PCR for the presence of the brachyury, goosecold, Xwnt-8, actin, globin, NCAM, and EF-1a transcripts. The results are shown in FIG. 4. Brachyury, is a general mesodermal marker. Goosecoid is a marker of dorsal mesoderm. Xwnt-8 is a marker of ventral-lateral mesoderm. Globin is a marker of ventral mesoderm. Actin is a marker of dorsal mesoderm. NCAM is a marker of neural tissue. EF-1a is a ubiquitously expressed message and demonstrates that roughly equal amounts of RNA are included in each reaction. Lane "E" of FIG. 4 contains total RNA harvested from whole embryos and is a positive control. The lane marked RT, is identical to the embryo lane except that reverse transcriptase (RT) was not included and is a negative control. The lane marked C, corresponds to animal caps treated identically to the other samples except no RNA was injected. As shown in FIG. 4, signalin1 converts the ectoderm to mesoderm that does not express the dorsal markers, muscle actin or NCAM, but does express the ventral marker, globin. Therefore, by morphological, histological, and molecular criteria, signalin1 induces the formation of ventral mesoderm. This places signalin1 in the signal transduction cascade of the BMPs.

Signalin2, like signalin1, converts the fate of the animal pole from ectoderm to mesoderm. However, the signalin2-induced mesoderm is dorsal in character. Signalin2 causes an elongation of the animal cap characteristic of dorsal mesoderm as depicted in FIG. 2. FIG. 3 shows histological analysis demonstrating the presence of the notochord and muscle, definitive dorsal tissues. In addition, signalin2 induces the expression of the molecular markers: brachyury, Xwnt-8, goosecoid, and actin, demonstrating the presence of dorsal mesoderm, as shown in FIG. 4. Taken together, this demonstrates that signalin2 induces the formation of dorsal mesoderm. and places signalin2 in the signal transduction cascade of Vg1, activin, and the TGFβs.

EXAMPLE 4

Differential Expression of Signalin Gene Products in Human Tissue

Using degenerate PCR primers for the signalin family, human cDNA samples were amplified from various tissues, using conditions as described for the cloning in Example 2 above. A strong predominant band at the correct size for the signalin transcript fragment was amplified with 31 cycles from kidney, liver, lung, mammary gland, pancreas, spleen, testis, and thymus. This demonstrates that at least one signalin member is expressed in each of these adult tissues.

By "A"-track sequencing (e.g., reading only A termination), data obtained demonstrated that, while the signalin gene products as a whole are ubiquitously expressed, certain of the signalins are differentially expressed in the above-mentioned tissues. The relative abundance of the signalin transcripts (of known identity) are as follows:

|          | human signalin type |      |      |      |      |      |      |
|----------|------|------|------|------|------|------|------|
| organ    | hu-1 | hu-2 | hu-3 | hu-4 | hu-5 | hu-6 | hu-7 |
| kidney   | 2    | 1    | 1    | —    | 1    | 1    | —    |
| spleen   | —    | 1    | —    | 1    | 1    | 2    | —    |

|          | human signalin type |      |      |      |      |      |      |
|----------|------|------|------|------|------|------|------|
| organ    | hu-1 | hu-2 | hu-3 | hu-4 | hu-5 | hu-6 | hu-7 |
| liver    | —    | —    | 5    | 1    | —    | —    | —    |
| pancreas | —    | —    | 5    | —    | —    | —    | 1    |

Note that the two gut derived organs, the liver and pancreas, have a preponderance of Hu-signalin 3. While in the kidney and spleen at least 4–5 of the different forms (known to date) are expressed. This data suggests a method by which TGF signaling pathways could be disrupted in a tissue specific manner. Finally, the A-tract data revealed that yet other signalin transcripts exist, e.g., indicating that the 7 sequences provided herein for the human signalin family are not inclusive of the entire family.

EXAMPLE 5

Identification of Human Signalins from Expressed Sequence Tag (EST) Sequnces Utilizing the program BLAST (Basic Local Alignment Search Tool; National Center for Biotechnology Information), certain of the cloned signalin sequences were compared with standard databases and sequences admitting to similarity with the cloned signalin sequences were examined. In particular, a number of the human EST sequences (see for review Boguski (1995) *Trends Biochemical Science* 20:295–296) were identified as similar to portions of the cloned signaling. Using the guidance of our sub-family groupings of the cloned signalin, we were able to piece together portions of the EST sequences, correcting for sequencing errors (especially frameshift errors), and derive more complete coding sequences for several human signalin clones.

In particular, an N-terminal fragment of a human cDNA was assembled from certain of the EST sequences and included the signalin motif of the human cloned sequence hu-signalin 1. The 170 residue fragment, represented by SEQ ID No. 12 (nucleotide) and SEQ ID No. 25 (amino acid), is a member of the α-subfamily, with substantial homology to other members of the α-subfamily even outside the signalin motif.

In similar fashion, a 121 residue C-terminal portion of a human signalin clone was assembled from the EST sequences based on sequences for the xenopus signalin clones. Analysis of the nucleotide (SEQ ID No. 13) and amino acid (SEQ ID No. 26) sequences of the fragment revealed that it most closely resembled xe-signalin 2, and accordingly was apparently a portion of transcript for a γ-subfamily member.

EXAMPLE 6

Localization of Signalin Proteins to Cytosol and Nucleus

Oocytes were injected with Signalin mRNA and cultured in media containing $^{35}$S-cysteine and $^{35}$S-methionine. The oocytes were then fractionated and total, secreted, membrane associated, nuclear, or cytosolic proteins analyzed by SDS-PAGE. The total homogenate demonstrates that signalin injected oocytes contain a specific band that corresponds to the signalin. Fractionation demonstrates that the signalins are located in the cytosol and the nucleus. No signalin was detected in the membrane or secreted factions. Of note, it appears that the signalin protein contained in the nucleus is slightly larger than that present in the cytosol. The results obtained with Xe-signalin 2 and Xe-signalin 1 are identical.

METHODS. Briefly, oocytes were manually isolated and defollicluated with collagenase. Then, the oocytes were injected with 30 ng of Signalin-encoding mRNA. After injection, the oocytes were cultured in media containing 35S-cysteine and 35S-methionine to label newly translated proteins. The culture media that contains the secreted proteins was isolated. 20 oocytes were homogenized on ice in 400 µl of 4° C. buffer 94A+[0.25 M Sucrose, 20 mM Hepes pH 7.4, 50 mM KCl, 0.5 mM MgCl2, 1 mM K-EGTA pH 7.4, 1 mM PMSF, 1 ug/ml leupeptin] and this fraction is termed total. The yolk was removed by low speed centrifugation at 4° C., 1000×g, for 5 minutes. The remaining supernatant was centrifuged at 4° C., 100,000×g, for 45 minutes to separate the membrane and cytosol fractions. The nuclei were isolated by manual dissection as described. After isolation, one oocyte equivalent of each compartment was analyzed by 10% SDS-PAGE in the presence of reducing agents.

EXAMPLE 7

Phosphorylation of Signalin Proteins

Xenopus signalin coding sequences were subcloned into expression vectors so as to include a myc epitope fused in frame to the signalin coding sequence. The fusion protein was subsequently expressed in COS cells. Briefly, the transfected COS cells were labeled with γ-[$^{38}$P]-ATP, and after incubation, were homogenized and immunoprecipitated with antibody against the myc-tag. $^{38}$P-labeled protein was detected in the precipitate by SDS-PAGE and autoradiography. Importantly, the myc-tagged proteins were also demonstrated to be active by the animal cap assay described in Example 3 above.

EXAMPLE 8

Truncated Activin Receptor Does Not Inhibit Signalin-2

The signalins function downstream of TGF-β receptors. Briefly, embryos were injected with mRNA that encodes the dominant negative activin receptor (tAR; described in PCT/US94/11745) (2 ng), Xe-signalin 2 (2 ng), or Xe-signalin 2 with tAR (2 ng of each). After injection, animal caps were dissected at stage 8 and cultured until sibling uninjected control embryos developed to either stage 11.5 (Early, gastrula) or 38 (Late, tadpole) and total RNA was harvested. The RNA was analyzed by RT-PCR for the presence of brachyury, actin, globin, NCAM, and EF-1a transcripts. The truncated activin receptor induces NCAM, but when coexpressed with the signalin transcript, does not block formation of mesoderm by Xe-signalin 2.

All of the above-cited references and publications are hereby incorporated by reference.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

What is claimed is:

1. An isolated nucleic acid comprising a coding sequence for a vertebrate polypeptide, wherein said coding sequence hybridizes under stringent conditions, including a wash step of 0.2×SSC at 65° C., to SEQ ID NO: 1, and wherein said polypeptide promotes the formation of ventral mesoderm in Xenopus animal pole explants.

2. An isolated nucleic acid comprising a coding sequence for a polypeptide, wherein said polypeptide is at least 90% identical to SEQ ID NO: 14, and wherein said polypeptide promotes the formation of ventral mesoderm in Xenopus animal pole explants.

3. The nucleic acid of claim 2, wherein said polypeptide is at least 95% identical to SEQ ID NO: 14.

4. The nucleic acid of claim 3, wherein said polypeptide is at least 98% identical to SEQ ID NO: 14.

5. The nucleic acid of claim 4, wherein said polypeptide is identical to SEQ ID NO: 14.

6. An isolated nucleic acid comprising a coding sequence for a polypeptide, wherein said polypeptide is at least 90% identical to SEQ ID NO: 15, and wherein said polypeptide promotes the formation of dorsal mesoderm in Xenopus animal pole explants.

7. The nucleic acid of claim 6, wherein said polypeptide is at least 95% identical to SEQ ID NO: 15.

8. The nucleic acid of claim 7, wherein said polypeptide is at least 98% identical to SEQ ID NO: 15.

9. The nucleic acid of claim 8, wherein said polypeptide is identical to SEQ ID NO: 15.

10. An isolated nucleic acid comprising a coding sequence for a vertebrate polypeptide, wherein said coding sequence hybridizes under stringent conditions, including a wash step of 0.2×SSC at 65° C., to SEQ ID NO: 2, and wherein said polypeptide promotes the formation of dorsal mesoderm in Xenopus animal pole explants.

11. The nucleic acid of claim 1, 2, 6 or 10, wherein said polypeptide is a fusion protein.

12. The nucleic acid of claim 11, wherein said fusion protein further includes a polypeptide sequence which functions as a detectable label for detecting the presence of said fusion protein or as a matrix-binding domain for immobilizing said fusion protein.

13. The nucleic acid of claim 1, 2, 6 or 10, further comprising a transcriptional regulatory sequence operably linked to said nucleotide sequence so as to render said nucleic acid suitable for use as an expression vector.

14. An expression vector, capable of replicating when transfected into at least one of a prokaryotic cell and eukaryotic cell, comprising the nucleic acid of claim 13.

15. A host cell transfected with the expression vector of claim 14, which expresses said polypeptide.

16. A method of producing said polypeptide comprising culturing the cell of claim 15 in a cell culture medium such that said polypeptide is expressed, and isolating said recombinant from said cell culture.

17. The nucleic acid of claim 1, 2, 6 or 10, wherein said polypeptide is a substrate for phosphorylation.

18. The nucleic acid of claim 1, 2, 6 or 10, wherein said polypeptide undergoes nuclear localization.

19. The nucleic acid of claim 1, 2, 6 or 10, wherein said polypeptide has a molecular weight in the range of 45–70 kD, as determined by SDS-PAGE.

20. The nucleic acid of claim 19, wherein said polypeptide has a molecular weight in the range of 45–55 kD as determined by SDS-PAGE.

21. The nucleic acid of claim 19, wherein said polypeptide has a molecular weight in the range of 60–70 kD as determined by SDS-PAGE.

22. A recombinant transfection system, comprising:

(i) a construct including the nucleic acid of claim 1, 2, 6 or 10, operably linked to a transcriptional regulatory sequence which regulates expression of said polypeptide in a eukaryotic cell; and (ii) a gene delivery composition for delivering said construct to a cell and causing said cell to be transfected with said construct.

23. The recombinant transfection system of claim 22, wherein said gene delivery composition is selected from at least one of a recombinant viral particle, a liposome, or a poly-cationic nucleic acid binding agent.

\* \* \* \* \*

UNITED STATES PATENT AND TRADEMARK OFFICE
CERTIFICATE OF CORRECTION

PATENT NO.    : 6,428,977 B1
DATED         : August 6, 2002
INVENTOR(S)   : Graff et al.

It is certified that error appears in the above-identified patent and that said Letters Patent is hereby corrected as shown below:

<u>Title page,</u>
Item [73], Assignee, add:

-- President and Fellows of Harvard College, Cambridge, MA --

Signed and Sealed this

Fifteenth Day of July, 2003

JAMES E. ROGAN
*Director of the United States Patent and Trademark Office*

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 1769 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 161..1552

(xi) SEQUENCE DESCRIPTION: SEQ ID NO:1:

```
GGAGATTTGT CCAGCAGATG CTGCTGGCCT TCTGGGAATC CTGGACTGTG ATTACTGCGC         60

TGGAGAGCTG TTATCTGTAA CTGGAAGACT CTCCATTAAC CTGCATTAAC AATATTGACC        120

TGGATTTCAC AGCAGTCCTA TAAAAAGTTG ACTAGTCACA ATG AAT GTG ACG AGC         175
                                              Met Asn Val Thr Ser
                                                1               5

TTG TTC TCC TTC ACC AGC CCA GCA GTG AAG AGG CTG CTT GGT TGG AAA         223
Leu Phe Ser Phe Thr Ser Pro Ala Val Lys Arg Leu Leu Gly Trp Lys
         10                  15                  20
```

```
CAG GGA GAC GAA GAA GAG AAA TGG GCA GAG AAA GCA GTA GAT GCC TTG      271
Gln Gly Asp Glu Glu Glu Lys Trp Ala Glu Lys Ala Val Asp Ala Leu
            25                  30                  35

GTG AAA AAG CTG AAG AAG AAA AAA GGA GCC ATG GAG GAA CTG GAA AAG      319
Val Lys Lys Leu Lys Lys Lys Lys Gly Ala Met Glu Glu Leu Glu Lys
        40                  45                  50

GCC CTG AGT TGT CCT GGA CAG CCC AGT AAC TGT GTC ACC ATT CCT CGT      367
Ala Leu Ser Cys Pro Gly Gln Pro Ser Asn Cys Val Thr Ile Pro Arg
    55                  60                  65

TCC TTG GAT GGC AGG CTG CAA GTG TCA CAC CGC AAG GGC CTA CCA CAT      415
Ser Leu Asp Gly Arg Leu Gln Val Ser His Arg Lys Gly Leu Pro His
70                  75                  80                  85

GTG ATT TAT TGC CGT GTG TGG CGT TGG CCG GAT CTA CAA AGT CAC CAT      463
Val Ile Tyr Cys Arg Val Trp Arg Trp Pro Asp Leu Gln Ser His His
                90                  95                  100

GAA CTG AAA CCC TTG GAG TGC TGC GAG TAT CCC TTT GGT TCT AAA CAG      511
Glu Leu Lys Pro Leu Glu Cys Cys Glu Tyr Pro Phe Gly Ser Lys Gln
            105                 110                 115

AAG GAG GTC TGC ATC AAC CCG TAT CAT TAC AAA CGA GTG GAG AGT CCT      559
Lys Glu Val Cys Ile Asn Pro Tyr His Tyr Lys Arg Val Glu Ser Pro
        120                 125                 130

GTC TTG CCA CCT GTC CTT GTT CCA CGG CAC AGT GAG TAC AAC CCA CAG      607
Val Leu Pro Pro Val Leu Val Pro Arg His Ser Glu Tyr Asn Pro Gln
    135                 140                 145

CAC AGT CTC CTT GCG CAA TTC CGA AAC TTG GAG CCA AGC GAG CCA CAT      655
His Ser Leu Leu Ala Gln Phe Arg Asn Leu Glu Pro Ser Glu Pro His
150                 155                 160                 165

ATG CCT CAC AAC GCA ACT TTT CCA GAC TCT TTC CAG CAG CCA AAC AGC      703
Met Pro His Asn Ala Thr Phe Pro Asp Ser Phe Gln Gln Pro Asn Ser
                170                 175                 180

CAT CCG TTC CCT CAC TCG CCG AAC AGC AGC TAC CCA AAC TCT CCG GGA      751
His Pro Phe Pro His Ser Pro Asn Ser Ser Tyr Pro Asn Ser Pro Gly
            185                 190                 195

AGC GGC AGT ACT TAT CCT CAC TCA CCA GCG AGC TCT GAT CCT GGG AGC      799
Ser Gly Ser Thr Tyr Pro His Ser Pro Ala Ser Ser Asp Pro Gly Ser
        200                 205                 210

CCT TTT CAA ATA CCA GCT GAC ACC CCT CCT CCA GCT TAT ATG CCT CCC      847
Pro Phe Gln Ile Pro Ala Asp Thr Pro Pro Pro Ala Tyr Met Pro Pro
    215                 220                 225

GAG GAT CAG ATG ACG CAA GAC AAC TCT CAG CCA ATG GAC ACA AAT CTG      895
Glu Asp Gln Met Thr Gln Asp Asn Ser Gln Pro Met Asp Thr Asn Leu
230                 235                 240                 245

ATG GTG CCT AAC ATC TCT CAA GAT ATC AAT AGA GCA GAT GTC CAG GCT      943
Met Val Pro Asn Ile Ser Gln Asp Ile Asn Arg Ala Asp Val Gln Ala
                250                 255                 260

GTT GCA TAT GAA GAG CCA AAA CAC TGG TGC TCC ATT GTC TAT TAT GAG      991
Val Ala Tyr Glu Glu Pro Lys His Trp Cys Ser Ile Val Tyr Tyr Glu
            265                 270                 275

CTC AAC AAC CGT GTT GGA GAA GCT TTC CAT GCC TCC TCC ACA AGT GTG     1039
Leu Asn Asn Arg Val Gly Glu Ala Phe His Ala Ser Ser Thr Ser Val
        280                 285                 290

TTG GTG GAT GGC TTC ACT GAT CCT TCA AAC AAC AGG AAC AGA TTT TGC     1087
Leu Val Asp Gly Phe Thr Asp Pro Ser Asn Asn Arg Asn Arg Phe Cys
    295                 300                 305

CTT GGG CTT CTG TCC AAT GTG AAC CGA AAC TCG ACC ATT GAG AAC ACC     1135
Leu Gly Leu Leu Ser Asn Val Asn Arg Asn Ser Thr Ile Glu Asn Thr
310                 315                 320                 325

AGG CGG CAT ATT GGA AAA GGT GTG CAT TTA TAT TAT GTT GGG GGT GAA     1183
Arg Arg His Ile Gly Lys Gly Val His Leu Tyr Tyr Val Gly Gly Glu
                330                 335                 340
```

```
GTC TAT GCC GAA TGC TTA AGT GAC AGC AGC ATT TTT GTT CAG AGC GGG    1231
Val Tyr Ala Glu Cys Leu Ser Asp Ser Ser Ile Phe Val Gln Ser Arg
            345                 350                 355

AAT TGT AAC TTT CAC CAC GGT TTC CAT CCT ACA ACT GTG TGT AAA ATC    1279
Asn Cys Asn Phe His His Gly Phe His Pro Thr Thr Val Cys Lys Ile
        360                 365                 370

CCC AGC GGA TGC AGC CTA AAG ATT TTT AAC AAC CAA GAA TTT GCT CAG    1327
Pro Ser Gly Cys Ser Leu Lys Ile Phe Asn Asn Gln Glu Phe Ala Gln
    375                 380                 385

CTT TTG GCC CAG TCT GTA AAC CAT GGC TTT GAA ACT GTC TAT GAA CTG    1375
Leu Leu Ala Gln Ser Val Asn His Gly Phe Glu Thr Val Tyr Glu Leu
390                 395                 400                 405

ACA AAG ATG TGC ACT ATT CGG ATG AGT TTT GTC AAG GGA TGG GGT GCA    1423
Thr Lys Met Cys Thr Ile Arg Met Ser Phe Val Lys Gly Trp Gly Ala
                410                 415                 420

GAA TGT CAT CGC CAG AAT GTC ACA AGC ACC CCC TGC TGG ATT GAG ATT    1471
Glu Cys His Arg Gln Asn Val Thr Ser Thr Pro Cys Trp Ile Glu Ile
            425                 430                 435

CAC CTG CAC GGC CCC CTT CAA TGG CTG GAT AAA GTA CTA ACT CAG ATG    1519
His Leu His Gly Pro Leu Gln Trp Leu Asp Lys Val Leu Thr Gln Met
        440                 445                 450

GGC TCA CCC CAT AAT CCC ATC TCC TCG GTC TCT TAATGGATTA GGATGTTCCT  1572
Gly Ser Pro His Asn Pro Ile Ser Ser Val Ser
    455                 460

GCCTCTGGAT TCATTGGAGC CATGCATGTA CTTGAAGGAG TCAGACACTT ACTGGCAAAT  1632

GGGACATTGG TAGTTTTTTT TTTTTAAAGT CTTGGGGGAG CGATAAGCCC CTCATCTACT  1692

TGATGTTTGT GACCAACTCT TACAGCTCCT ATCCTGTGTG TAGCTCCTAT CCTGTGTGTA  1752

GCTCCTATCC TGTGTGC                                                 1769

(2) INFORMATION FOR SEQ ID NO:2:

(i) SEQUENCE CHARACTERISTICS:
            (A) LENGTH: 1708 base pairs
            (B) TYPE: nucleic acid
            (C) STRANDEDNESS: both
            (D) TOPOLOGY: linear (ii) MOLECULE TYPE: cDNA (ix) FEATURE:
            (A) NAME/KEY: CDS
            (B) LOCATION: 51..1451

(xi) SEQUENCE DESCRIPTION: SEQ ID NO:2:

GCAACATCTC CAGGTAAGAA GCGGATCTTA AGCAGCAGCA GTGGCAAAAC ATG TCG      56
                                                      Met Ser
                                                        1

TCC ATC TTG CCT TTC ACC CCG CCA GTA GTG AAG CGC CTG CTA GGA TGG    104
Ser Ile Leu Pro Phe Thr Pro Pro Val Val Lys Arg Leu Leu Gly Trp
        5                   10                  15

AAG AAG TCT GCA AGT GGC ACC ACA GGA GCA GGT GGC GAT GAG CAG AAC    152
Lys Lys Ser Ala Ser Gly Thr Thr Gly Ala Gly Gly Asp Glu Gln Asn
    20                  25                  30

GGA CAG GAA GAG AAG TGG TGC GAA AAA GCG GTA AAG AGC TTG GTG AAA    200
Gly Gln Glu Glu Lys Trp Cys Glu Lys Ala Val Lys Ser Leu Val Lys
35                  40                  45                  50

AAA CTG AAG AAA ACG GGA CAA TTA GAC GAG CTT GAG AAG GCG ATC ACG    248
Lys Leu Lys Lys Thr Gly Gln Leu Asp Glu Leu Glu Lys Ala Ile Thr
                55                  60                  65

ACG CAG AAC TGC AAC ACG AAA TGC GTA ACG ATA CCA AGC ACT TGC TCT    296
```

```
                    Thr Gln Asn Cys Asn Thr Lys Cys Val Thr Ile Pro Ser Thr Cys Ser
                                     70                  75                  80

GAA ATT TGG GGA CTG AGT ACA GCA AAT ACC ATA GAT CAG TGG GAT ACC           344
Glu Ile Trp Gly Leu Ser Thr Ala Asn Thr Ile Asp Gln Trp Asp Thr
            85                  90                  95

ACA GGC CTT TAC AGC TTC TCT GAA CAA ACC AGG TCT CTT GAT GGT CGA           392
Thr Gly Leu Tyr Ser Phe Ser Glu Gln Thr Arg Ser Leu Asp Gly Arg
    100                 105                 110

CTC CAG GTG TCT CAC CGT AAA GGA TTG CCG CAT GTT ATC TAC TGC AGA           440
Leu Gln Val Ser His Arg Lys Gly Leu Pro His Val Ile Tyr Cys Arg
115                 120                 125                 130

CTG TGG CGC TGG CCA GAC CTG CAC AGT CAT CAT GAA CTG AAA GCA ATC           488
Leu Trp Arg Trp Pro Asp Leu His Ser His His Glu Leu Lys Ala Ile
                135                 140                 145

GAA AAT TGT GAA TAT GCT TTT AAC CTT AAA AAA GAT GAA GTT TGT GTC           536
Glu Asn Cys Glu Tyr Ala Phe Asn Leu Lys Lys Asp Glu Val Cys Val
            150                 155                 160

AAT CCA TAC CAT TAT CAG AGG GTG GAG ACA CCA GTT TTA CCA CCT GTA           584
Asn Pro Tyr His Tyr Gln Arg Val Glu Thr Pro Val Leu Pro Pro Val
    165                 170                 175

TTA GTT CCA CGG CAC ACG GAA ATC TTG ACA GAG CTG CCA CCT CTT GAT           632
Leu Val Pro Arg His Thr Glu Ile Leu Thr Glu Leu Pro Pro Leu Asp
180                 185                 190

GAC TAC ACG CAT TCC ATT CCA GAA AAC ACT AAT TTT CCT GCA GGG ATT           680
Asp Tyr Thr His Ser Ile Pro Glu Asn Thr Asn Phe Pro Ala Gly Ile
195                 200                 205                 210

GAA CCT CAG AGC AAT TAT ATT CCA GAA ACA CCA CCT CCT GGA TAT ATT           728
Glu Pro Gln Ser Asn Tyr Ile Pro Glu Thr Pro Pro Pro Gly Tyr Ile
                215                 220                 225

AGT GAA GAT GGA GAA ACT AGC GAT CAG CAA CTT AAC CAA AGC ATG GAC           776
Ser Glu Asp Gly Glu Thr Ser Asp Gln Gln Leu Asn Gln Ser Met Asp
            230                 235                 240

ACA GGG TCA CCA GCT GAG CTG TCT CCG AGT ACA CTT TCT CCA GTC AAC           824
Thr Gly Ser Pro Ala Glu Leu Ser Pro Ser Thr Leu Ser Pro Val Asn
    245                 250                 255

CAC AAT CTC GAT TTG CAA CCT GTC ACC TAT TCG GAA CCT GCT TTT TGG           872
His Asn Leu Asp Leu Gln Pro Val Thr Tyr Ser Glu Pro Ala Phe Trp
260                 265                 270

TGC TCT ATA GCA TAC TAC GAA CTG AAT CAG CGA GTA GGA GAA ACT TTC           920
Cys Ser Ile Ala Tyr Tyr Glu Leu Asn Gln Arg Val Gly Glu Thr Phe
275                 280                 285                 290

CAT GCA TCG CAA CCA TCG CTT ACC GTG GAC GGC TTT ACG GAC CCC TCA           968
His Ala Ser Gln Pro Ser Leu Thr Val Asp Gly Phe Thr Asp Pro Ser
                295                 300                 305

AAC TCT GAA AGG TTC TGC TTA GGT TTA CTC TCA AAT GTG AAC CGA AAT          1016
Asn Ser Glu Arg Phe Cys Leu Gly Leu Leu Ser Asn Val Asn Arg Asn
            310                 315                 320

GCC ACG GTG GAA ATG ACC AGG CGT CAC ATA GGA AGG GGT GTC CGG CTA          1064
Ala Thr Val Glu Met Thr Arg Arg His Ile Gly Arg Gly Val Arg Leu
    325                 330                 335

TAT TAC ATC GGT GGA GAG GTG TTT GCA GAG TGC CTA AGT GAT AGT GCT          1112
Tyr Tyr Ile Gly Gly Glu Val Phe Ala Glu Cys Leu Ser Asp Ser Ala
340                 345                 350

ATT TTT GTT CAG AGT CCA AAC TGT AAC CAG CGA TAT GGA TGG CAT CCA          1160
Ile Phe Val Gln Ser Pro Asn Cys Asn Gln Arg Tyr Gly Trp His Pro
355                 360                 365                 370

GCA ACT GTA TGT AAG ATT CCT CCA GGA TGC AAT CTG AAG ATT TTC AAT          1208
Ala Thr Val Cys Lys Ile Pro Pro Gly Cys Asn Leu Lys Ile Phe Asn
                375                 380                 385
```

```
AAT CAA GAG TTT GCG GCT CTC CTC GCT CAG TCT GTG AAT CAA GGC TTT          1256
Asn Gln Glu Phe Ala Ala Leu Leu Ala Gln Ser Val Asn Gln Gly Phe
            390                 395                 400

GAA GCA GTT TAT CAG TTA ACT CGA ATG TGC ACC ATA AGG ATG AGC TTT          1304
Glu Ala Val Tyr Gln Leu Thr Arg Met Cys Thr Ile Arg Met Ser Phe
        405                 410                 415

GTA AAA GGC TGG GGT GCT GAA TAC AGG CGA CAG ACC GTT ACA AGC ACT          1352
Val Lys Gly Trp Gly Ala Glu Tyr Arg Arg Gln Thr Val Thr Ser Thr
    420                 425                 430

CCA TGC TGG ATT GAG CTT CAC CTG AAT GGA CCT TTG CAG TGG TTG GAC          1400
Pro Cys Trp Ile Glu Leu His Leu Asn Gly Pro Leu Gln Trp Leu Asp
435                 440                 445                 450

AAA GTG TTG ACA CAG ATG GGA TCC CCT TCA GTC CGC TGC TCA AGC ATG          1448
Lys Val Leu Thr Gln Met Gly Ser Pro Ser Val Arg Cys Ser Ser Met
                455                 460                 465

TCC TAATGGTCTC CTCTTTTTAA TGTATTACCT GCGGGCGGCA ACTGCAGTCC               1501
Ser

CAGCAACAGA CTCAATACAG CTTGTCTGTC GTAGTATTTG TGTGTGGTGC CCATGAACTG        1561

TTTACAATCC AAAAGAGAGA GAATAAAAAA GCAAAAACAG CACTTGAGAT CCCATCAACG        1621

AAAAGCACCT TGTTGGATGA TGTTTCTGAT ACTCTTAAAG TAGATCCGTG TATAAATGAC        1681

TCCTTACCTG GGAAAAGGGA CTTTTTC                                            1708

(2) INFORMATION FOR SEQ ID NO:3:

(i) SEQUENCE CHARACTERISTICS:
        (A) LENGTH: 2594 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 259..1656

(xi) SEQUENCE DESCRIPTION: SEQ ID NO:3:

GGCTGCTGCT CCTCCCCCTT CTACAGCCCA AATCACTCCG CATGCACCGA GGCCGGAGGG          60

ACCAGCGCAG CGCAGCGGAG ACACAGGACA TATGGCCAGA ACCTTGAGAG ATGTCTAAAT         120

GTTTCCTTGA ACATTTTCC TGGACTCCTT CTGATAAAGA ATAAATTGAA GAAGGTGTGC         180

AAGATTCCTT GACGCCTGCA CTCGTTGCAT CTTTGGCCTC CATCTTGGTT TGATCTGTAG        240

GTAAACACAG CAAATCCA ATG CAC GCC AGC ACT CCC ATC AGC TCT TTG TTC          291
                    Met His Ala Ser Thr Pro Ile Ser Ser Leu Phe
                     1               5                  10

TCC TTC ACT AGC CCT GCT GTC AAA AGG CTG CTT GGC TGG AAG CAA GGG          339
Ser Phe Thr Ser Pro Ala Val Lys Arg Leu Leu Gly Trp Lys Gln Gly
            15                  20                  25

GAC GAA GAA GAA AAA TGG GCA GAG AAA GCG GTG GAC TCG CTT GTG AAG          387
Asp Glu Glu Glu Lys Trp Ala Glu Lys Ala Val Asp Ser Leu Val Lys
        30                  35                  40

AAA CTG AAG AAG AAG AAA GGG GCA ATG GAG GAA CTA GAA AGG GCT TTA          435
Lys Leu Lys Lys Lys Lys Gly Ala Met Glu Glu Leu Glu Arg Ala Leu
    45                  50                  55

AGT TGT CCA GGG CAA CCT AGT AAA TGT GTC ACT ATC CCA CGG TCA TTG          483
Ser Cys Pro Gly Gln Pro Ser Lys Cys Val Thr Ile Pro Arg Ser Leu
60                  65                  70                  75

GAT GGG AGG TTA CAA GTG TCC CAT CGC AAA GGC CTC CCC CAT GTC ATC          531
Asp Gly Arg Leu Gln Val Ser His Arg Lys Gly Leu Pro His Val Ile
                80                  85                  90
```

```
TAT TGC CGG GTT TGG AGG TGG CCT GAT CTG CAG TCT CAT CAT GAG CTG      579
Tyr Cys Arg Val Trp Arg Trp Pro Asp Leu Gln Ser His His Glu Leu
             95                 100                 105

AAA CCA ATG GAA TGC TGC GAG TTC CCT TTT GGG TCC AAG CAG AAA GAC      627
Lys Pro Met Glu Cys Cys Glu Phe Pro Phe Gly Ser Lys Gln Lys Asp
        110                 115                 120

GTG TGC ATC AAC CCC TAC CAT TAC CGG AGG GTG GAA ACA CCA GTG TTA      675
Val Cys Ile Asn Pro Tyr His Tyr Arg Arg Val Glu Thr Pro Val Leu
    125                 130                 135

CCG CCG GTG CTT GTT CCA AGA CAC AGC GAG TTC AAC CCA CAG CTG AGC      723
Pro Pro Val Leu Val Pro Arg His Ser Glu Phe Asn Pro Gln Leu Ser
140                 145                 150                 155

CTT CTA GCA AAG TTT CGA AAC ACC TCG CTG AAT AAT GAA CCA CTA ATG      771
Leu Leu Ala Lys Phe Arg Asn Thr Ser Leu Asn Asn Glu Pro Leu Met
                160                 165                 170

CCA CAC AAT GCA ACT TTC CCG GAG TCT TTC CAG CAG CCC CCA TGC ACT      819
Pro His Asn Ala Thr Phe Pro Glu Ser Phe Gln Gln Pro Pro Cys Thr
            175                 180                 185

CCA TTC TCT TCC TCA CCA AGT AAC ATC TTC TCT CAG TCC CCG AAC ACA      867
Pro Phe Ser Ser Ser Pro Ser Asn Ile Phe Ser Gln Ser Pro Asn Thr
        190                 195                 200

GTG GGC TAT CCA GAT TCT CCT AGG AGT TCC ACT GAC CCA GGA AGC CCC      915
Val Gly Tyr Pro Asp Ser Pro Arg Ser Ser Thr Asp Pro Gly Ser Pro
    205                 210                 215

CCG TAC CAG ATC ACA GAG ACG CCC CCT CCG CCA TAT AAT GCT CCA GAC      963
Pro Tyr Gln Ile Thr Glu Thr Pro Pro Pro Pro Tyr Asn Ala Pro Asp
220                 225                 230                 235

CTT CAA GGG AAT CAA AAC AGA CCA ACT GCA GAC CCA GCT GAA TGC CAG     1011
Leu Gln Gly Asn Gln Asn Arg Pro Thr Ala Asp Pro Ala Glu Cys Gln
                240                 245                 250

TTA GTT TTG TCA GCA CTG AAC AGA GAC TTT CGC CCG GTT TGC TAT GAA     1059
Leu Val Leu Ser Ala Leu Asn Arg Asp Phe Arg Pro Val Cys Tyr Glu
            255                 260                 265

GAG CCA TTG CAT TGG TGT TCT GTC GCT TAT TAT GAA CTG AAT AAT CGA     1107
Glu Pro Leu His Trp Cys Ser Val Ala Tyr Tyr Glu Leu Asn Asn Arg
        270                 275                 280

GTA GGG GAG ACC TTC CAG GCC TCC GCA CGC AGT GTC CTC ATC GAC GGG     1155
Val Gly Glu Thr Phe Gln Ala Ser Ala Arg Ser Val Leu Ile Asp Gly
    285                 290                 295

TTC ACG GAC CCC TCC AAT AAT AAG AAC AGG TTC TGC TTA GGA CTT CTC     1203
Phe Thr Asp Pro Ser Asn Asn Lys Asn Arg Phe Cys Leu Gly Leu Leu
300                 305                 310                 315

TCA AAT GTC AAC CGC AAC TCC ACT ATT GAA AAC ACC CGC AGA CAC ATT     1251
Ser Asn Val Asn Arg Asn Ser Thr Ile Glu Asn Thr Arg Arg His Ile
                320                 325                 330

GGA AAG GGG GTC CAT CTT TAC TAC GTG GGC GGA GAG GTG TAT GCA GAA     1299
Gly Lys Gly Val His Leu Tyr Tyr Val Gly Gly Glu Val Tyr Ala Glu
            335                 340                 345

TGC GTG AGC GAC AGC AGC ATT TTC GTA CAG AGT CGC AAC TGC AAT TAC     1347
Cys Val Ser Asp Ser Ser Ile Phe Val Gln Ser Arg Asn Cys Asn Tyr
        350                 355                 360

CAG CAC GGC TTC CAT CCC TCC ACT GTC CGC AAG ATC CCC AGT GGC TGC     1395
Gln His Gly Phe His Pro Ser Thr Val Arg Lys Ile Pro Ser Gly Cys
    365                 370                 375

AGC CTG AAG ATC TTT AAT AAC CAA CTA TTT GCC CAG CTA CTT TCC CAG     1443
Ser Leu Lys Ile Phe Asn Asn Gln Leu Phe Ala Gln Leu Leu Ser Gln
380                 385                 390                 395

TCC GTT AAC CAA GGG TTC GAG GTG GTT TAT GAG CTG ACG AAA ATG TGC     1491
Ser Val Asn Gln Gly Phe Glu Val Val Tyr Glu Leu Thr Lys Met Cys
```

-continued

```
                   400             405              410
ACA ATT CGT ATG AGC TTT GTT AAA GGA TGG GGA GCA GAA TAT AAC CGA   1539
Thr Ile Arg Met Ser Phe Val Lys Gly Trp Gly Ala Glu Tyr Asn Arg
            415             420                 425

CAG GAT GTC ACT AGC ACC CCC TGC TGG ATT GAA ATC CAT CTA CAC GGG   1587
Gln Asp Val Thr Ser Thr Pro Cys Trp Ile Glu Ile His Leu His Gly
            430             435             440

CCG CTT CAA TGG CTG GAC AAG GTT CTG ACA CAG ATG GGT TCA CCG CAT   1635
Pro Leu Gln Trp Leu Asp Lys Val Leu Thr Gln Met Gly Ser Pro His
    445             450             455

AAT CCA ATC TCT TCC GTA TCG TAAACTCTCC GCGGCCACAC AACGCAGGCA      1686
Asn Pro Ile Ser Ser Val Ser
460             465

AGGACACACC TGGGACTAGT TGCCCTTATA TAAAAGAGCA CATAATGCCA GTCACACGCC  1746

TCAGCAGAAA AAGGCATCCA CAACCCATAA TCACTTCTGA CTTTTAGGTA TCGGATATAT  1806

TCCATAGATA TATATATAAA CCACTTTCCT GTTCTTTTAA CAGTCCAGGA AACAGAACCA  1866

CCTTTTGGGT CATAAGGAAT AGGGCTTAAT GGGGTGGGGC TTAAAGCAGG GATGCCTGCT  1926

TGGTAGAATG GGGTGTGTCC TGGGCAGGTC TGGGCGTGGC CAAGCATGCC TTCTTTAGAT  1986

GAATTAAAGG GGTACTATTT ATATTTAGAT GGCATCACAC AAGGGGCCTA GCTAAGCAGA  2046

GGGCTGAGGA TCCAGTAGTA TGGTAGTATA GTCCCATAGT ATTTCTAATG ATGGTCCTGC  2106

CATGAAAAAA AAATTCCAAA TACACTCCAT TGATTTACCC ATCAGCCCTT TAGATCTGCG  2166

ACTCTTCCTC CTGAAACTTA TATGGTATGT GGTTCGATGA CCCTTTTGTG GTCTGTTGTG  2226

AAGGGCTATA TAAATAAGTA ATAACTGCAT TACATGGGCT TGGATTAGGC TTCCCTACTT  2286

GAAATGAAGG GAGATGATTG AGTCCTGCCC CTCCCCCACC ATAGCATTTG CTTGCTGTGC  2346

TACACTTACA CCCATGGGTC ATCTTTAGGC CTTACTGTCG CCATTTTGT CAGCGGGTAG   2406

CCATTGTACT GTACATACAT GCATTTCAGT AATGTGTTTT TAGTGTAACG ATTATGCTTT  2466

TATATATATA TTGTACATAC TGTTTCTATG GAGAGAGCAC TTCACCAGTA CTGACTATAA  2526

GAATAACAGG CGGAACGGAG TTTCGCTTTA TTTCTAACCA ATCGGTTCTC AGATCCAGAA  2586

ACAAAGCG                                                          2594
```

(2) INFORMATION FOR SEQ ID NO:4:

(i) SEQUENCE CHARACTERISTICS:
        (A) LENGTH: 2879 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 258..2042

(xi) SEQUENCE DESCRIPTION: SEQ ID NO:4:

```
GAGCATGTAT TTAAATGAAT CACTTAGCAG CATATCATTG TTTAACAGAA GGAAGGGCTA    60

AAGTTGTAAT GTAGCTGGAT CTAAATTAGC ATGAATTACT CCTATTAGTA ATGTTAGTCT   120

GGTGGGGAG GGGAGATGGG CTGCACCTGG ATCCACGCTG AGAATTGAGC TGTGCCACTG    180

AGCATGCTCT GGCTTTTTGT ACCACTAATT GGTTCAGTCC AATAAACCCC ATGGAGGTGT   240

AACAACAAGG GCAAAAG ATG GCG TTT GCC AGC CTA GAG CTC GCC CTG CAC      290
                   Met Ala Phe Ala Ser Leu Glu Leu Ala Leu His
                    1               5                  10
```

```
CGA GTG CCC CCC GCC CGG TGT GGA GAT GAG GAG ATC TAC GGG GAA GGC        338
Arg Val Pro Pro Ala Arg Cys Gly Asp Glu Glu Ile Tyr Gly Glu Gly
            15                  20                  25

TTG TCT GAG GGG GAG ATC CCG GCC ATG TCT CTG ACC CCT CCT AAC AGC        386
Leu Ser Glu Gly Glu Ile Pro Ala Met Ser Leu Thr Pro Pro Asn Ser
        30                  35                  40

AGT GAT GCC TGT CTC AGC ATC GTA CAC AGT CTC ATG TGC CAC CGG CAG        434
Ser Asp Ala Cys Leu Ser Ile Val His Ser Leu Met Cys His Arg Gln
    45                  50                  55

GGG GGG GAG AAC GAG GGC TTT GCC AAG AGA GCC ATT GAG AGT CTC GTC        482
Gly Gly Glu Asn Glu Gly Phe Ala Lys Arg Ala Ile Glu Ser Leu Val
60                  65                  70                  75

AAG AAA CTG AAG GAG AAG AAA GAC GAG CTG GAC TCC CTC ATC ACT GCC        530
Lys Lys Leu Lys Glu Lys Lys Asp Glu Leu Asp Ser Leu Ile Thr Ala
                80                  85                  90

ATT ACT ACT AAT GGA GTG CAC CCC AGC AAG TGC GTT ACC ATC CAG CGA        578
Ile Thr Thr Asn Gly Val His Pro Ser Lys Cys Val Thr Ile Gln Arg
            95                  100                 105

ACC TTG GAC GGG AGG CTT CAG GTA GCC GGC CGT AAA GGT TTC CCA CAT        626
Thr Leu Asp Gly Arg Leu Gln Val Ala Gly Arg Lys Gly Phe Pro His
        110                 115                 120

GTG ATC TAC GCT CGT TTG TGG CAC TGG CCG GAC CTG CAC AAG AAT GAG        674
Val Ile Tyr Ala Arg Leu Trp His Trp Pro Asp Leu His Lys Asn Glu
    125                 130                 135

CTG AAA CAC GTT AAG TTC TGC CAG TTC GCC TTC GAC CTG AAG TAC GAC        722
Leu Lys His Val Lys Phe Cys Gln Phe Ala Phe Asp Leu Lys Tyr Asp
140                 145                 150                 155

AGC GTG TGC GTG AAC CCC TAT CAC TAC GAG CGG GTG GTT TCT CCC GGC        770
Ser Val Cys Val Asn Pro Tyr His Tyr Glu Arg Val Val Ser Pro Gly
                160                 165                 170

ATT GGT CTG AGT ATC CCT AGC ACT GTG ACC ACC CCA TGC CGG TCA GTA        818
Ile Gly Leu Ser Ile Pro Ser Thr Val Thr Thr Pro Cys Arg Ser Val
            175                 180                 185

AAA GAG GAG TAT GTC CAT GAG TGT GAA ATG GAT GCA TCT TCA TGT CTC        866
Lys Glu Glu Tyr Val His Glu Cys Glu Met Asp Ala Ser Ser Cys Leu
        190                 195                 200

CCA GCA TCC CAG GAA CTT CCG CCA GCC ATC AAA CAT GCC TCC CTT CCA        914
Pro Ala Ser Gln Glu Leu Pro Pro Ala Ile Lys His Ala Ser Leu Pro
    205                 210                 215

CCA ATG CCT CCT ACA GAG TCC TAC AGG CAG CCA CTG CCC CCA CTC ACC        962
Pro Met Pro Pro Thr Glu Ser Tyr Arg Gln Pro Leu Pro Pro Leu Thr
220                 225                 230                 235

CTA CCC AAG AGC CCC CAG ACT GCT ATC AGC ATG TAT CCC AAC ATG CCC       1010
Leu Pro Lys Ser Pro Gln Thr Ala Ile Ser Met Tyr Pro Asn Met Pro
                240                 245                 250

CTC TCT CCC TCT GTG GCT CCT GGT TGC CCT CTC ATA CCT ATG CAT GGT       1058
Leu Ser Pro Ser Val Ala Pro Gly Cys Pro Leu Ile Pro Met His Gly
            255                 260                 265

GAG GGG TTA CTA CAG ATA GCT CCA TCC CAT CCC CAG CAA ATG TTG TCC       1106
Glu Gly Leu Leu Gln Ile Ala Pro Ser His Pro Gln Gln Met Leu Ser
        270                 275                 280

ATA TCT CCG CCT TCC ACA CCG AGC CAG AAC TCC AGC AGA ATG GT TAT       1154
Ile Ser Pro Pro Ser Thr Pro Ser Gln Asn Ser Gln Gln Asn Gly Tyr
    285                 290                 295

TCT TCC CCC CCA AAG CAG CCT TTC CAT GCT TCT TGG ACA GGG AGC AGC       1202
Ser Ser Pro Pro Lys Gln Pro Phe His Ala Ser Trp Thr Gly Ser Ser
300                 305                 310                 315

ACA GCT GTA TAT ACC CCG AAC CCT GGG GTA CAG CAG AAC GGA AAA GGA       1250
Thr Ala Val Tyr Thr Pro Asn Pro Gly Val Gln Gln Asn Gly Lys Gly
                320                 325                 330
```

```
AAC CAG CAA CCT CCA CTT CAC CAC GCC AAC AAC TAC TGG CCC CTT CAC      1298
Asn Gln Gln Pro Pro Leu His His Ala Asn Asn Tyr Trp Pro Leu His
            335                 340                 345

CAG AGC TCC CCT CAG TAT CAG CAC CCC GTG TCA AAC CAC CCA GGC CCA      1346
Gln Ser Ser Pro Gln Tyr Gln His Pro Val Ser Asn His Pro Gly Pro
            350                 355                 360

GAG TTC TGG TGC TCC GTT GCC TAT TTC GAG ATG GAT GTT CAG GTT GGG      1394
Glu Phe Trp Cys Ser Val Ala Tyr Phe Glu Met Asp Val Gln Val Gly
            365                 370                 375

GAG ATA TTT AAA GTC CCA TCT AAC TGT CCC GTG GTC ACG GTG GAT GGA      1442
Glu Ile Phe Lys Val Pro Ser Asn Cys Pro Val Val Thr Val Asp Gly
380                 385                 390                 395

TAT GTG GAC CCC TCT GGT GGG GAT CGG TTT TGC CTT GGT CAG CTT TCT      1490
Tyr Val Asp Pro Ser Gly Gly Asp Arg Phe Cys Leu Gly Gln Leu Ser
                400                 405                 410

AAC GTG CAT CGC ACA GAC ACT AGT GAG CGT GCA AGG CTT CAC ATC GGG      1538
Asn Val His Arg Thr Asp Thr Ser Glu Arg Ala Arg Leu His Ile Gly
            415                 420                 425

AAG GGA GTG CAG CTT GAG TGT CGG GGC GAG GGA GAC GTA TGG ATG AGG      1586
Lys Gly Val Gln Leu Glu Cys Arg Gly Glu Gly Asp Val Trp Met Arg
            430                 435                 440

TGC CTC AGT GAT CAC GCC GTG TTT GTT CAG AGT TAT TAC TTG GAC AGG      1634
Cys Leu Ser Asp His Ala Val Phe Val Gln Ser Tyr Tyr Leu Asp Arg
            445                 450                 455

GAA GCA GGG CGA GCG CCG GGA GAT GCA GTC CAC AAG ATT TAT CCA GGC      1682
Glu Ala Gly Arg Ala Pro Gly Asp Ala Val His Lys Ile Tyr Pro Gly
460                 465                 470                 475

GCC TAC ATT AAG GTG TTT GAC TTG CGA CAG TGT CAC CGG CAG ATG CAG      1730
Ala Tyr Ile Lys Val Phe Asp Leu Arg Gln Cys His Arg Gln Met Gln
                480                 485                 490

CAG CAG GCG GCT ACG GCT CAA GCA GCG GCT GCA GCC CAA GCG GCG GCT      1778
Gln Gln Ala Ala Thr Ala Gln Ala Ala Ala Ala Gln Ala Ala Ala
            495                 500                 505

GTG GCC GGC GCA ATC CCT GGT CCC GGG TCG GTG GGG GCA ATC GCT CCT      1826
Val Ala Gly Ala Ile Pro Gly Pro Gly Ser Val Gly Gly Ile Ala Pro
            510                 515                 520

GCT GTC AGT CTT TCT GCT GCG GCC GGT ATC GGG GTG GAC GAC CTA CGG      1874
Ala Val Ser Leu Ser Ala Ala Ala Gly Ile Gly Val Asp Asp Leu Arg
            525                 530                 535

CGC CTC TGT ATC TTG CGC CTT AGT TTT GTG AAG GGC TGG GGC CCT GAT      1922
Arg Leu Cys Ile Leu Arg Leu Ser Phe Val Lys Gly Trp Gly Pro Asp
540                 545                 550                 555

TAC CCT CGG CAG AGC ATC AAG CAG ACT CCC TGC TGG ATC GAG GTC CAT      1970
Tyr Pro Arg Gln Ser Ile Lys Gln Thr Pro Cys Trp Ile Glu Val His
                560                 565                 570

CTT CAC CGT GCG CTG CAG CTT CTT GAT GAA GTT CTC CAT ACT TTG CCA      2018
Leu His Arg Ala Leu Gln Leu Leu Asp Glu Val Leu His Thr Leu Pro
            575                 580                 585

ATG GCA GAC CCC AGT TCT GTC AAC TAACCAAGAC CCCGAGGTCT GTCAGATTGC     2072
Met Ala Asp Pro Ser Ser Val Asn
            590                 595

CAGTGGCAGA CTAACTGTCA ACTACCAAAG CCAGGATGAG ACAAGACTCC TAATTAAGAC    2132

TCATCCAGTC CAAAGTGAGC CAATCAGGAT TCATCCAATC ATATGTTAAG CAAAGACAAA    2192

TGTTTGCCAT AGACCTTCCA GTCCTTTGGA GACCCGGCCA ATACATTGGG CACACGGATA    2252

CCTGACGCCC CCTTGGTCCT TCCTGCTGAT TGGTGGAACC AGTAGGATGG AGGCACAGAA    2312

CTCCCCCGAG TGGAGATACA CAGGACATGT GACTTTGGGT GAAGTAGATG AACTGTGTTT    2372
```

```
TTATAGCTGA AATGCATTAA ATGTTCCTTA TTTTTTTGGT CAGAAGATTA TTTTTGGTCT     2432

GATATTTGGC TTTTTAGTGC CGGGACGGAC TCCCAACATT TCCCTGACGT TCAAAGGCTA     2492

AATAAATGCA GATATATAAA TGCTTTTTGT ATGTGCCAGT TAAAATGATG TGGCTACCTC     2552

AGTTCCTTTA GCCCCCCATT CCCCCTCCAT TGGTACTAAC ACGTCTAACA GACAAGCAGG     2612

ATCTGCTGGT TTACACGGCA CACACATGTT TTACGCTGCT TTCCAAAGCC TGGGGAGATA     2672

TTTGGTGTAT TTTGATGTCT GTTTTCGGCG AGCGCATTTT TATTTTTTGT TGTGGTATCA     2732

CTTCTAGGCC AAATGTGTAC AGATAAAACC AAAAACCACA GCCGTGTGTG CAAAGGTTTC     2792

TTTTCACATA TTAAGAACCT GTCAAATGGC TTCTGATGTA TTCTAAATAA AATATTTATG     2852

TACTGTTGCC TATAAAAAAA AAAAACG                                         2879

(2) INFORMATION FOR SEQ ID NO:5:

(i) SEQUENCE CHARACTERISTICS:
        (A) LENGTH: 132 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..132

(xi) SEQUENCE DESCRIPTION: SEQ ID NO:5:

GTC TCC CAC CGG AAG GGA CTG CCT CAT GTC ATT TAC TGC CGT GTG TGG         48
Val Ser His Arg Lys Gly Leu Pro His Val Ile Tyr Cys Arg Val Trp
 1               5                  10                  15

CGC TGG CCC GAT CTT CAG AGC CAC CAT GAG CTA AAA CCA CTG GAA TGC         96
Arg Trp Pro Asp Leu Gln Ser His His Glu Leu Lys Pro Leu Glu Cys
                20                  25                  30

TGT GAG TTT CCT TTT GGT TCC AAG CAG AAG GAG GTC                        132
Cys Glu Phe Pro Phe Gly Ser Lys Gln Lys Glu Val
            35                  40

(2) INFORMATION FOR SEQ ID NO:6:

(i) SEQUENCE CHARACTERISTICS:
        (A) LENGTH: 132 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..132

(xi) SEQUENCE DESCRIPTION: SEQ ID NO:6:

GTG GCT GGT CGG AAA GGA TTT CCT CAT GTG ATC TAT GCC CGT CTC TGG         48
Val Ala Gly Arg Lys Gly Phe Pro His Val Ile Tyr Ala Arg Leu Trp
 1               5                  10                  15

AGG TGG CCT GAT CTT CAC AAA AAT GAA CTA AAA CAT GTT AAA TAT TGT         96
Arg Trp Pro Asp Leu His Lys Asn Glu Leu Lys His Val Lys Tyr Cys
                20                  25                  30

CAG TAT GCG TTT GAC TTA AAA TGT GAT AGT GTC TGC                        132
Gln Tyr Ala Phe Asp Leu Lys Cys Asp Ser Val Cys
            35                  40

(2) INFORMATION FOR SEQ ID NO:7:
```

(i) SEQUENCE CHARACTERISTICS:
    (A) LENGTH: 132 base pairs
    (B) TYPE: nucleic acid
    (C) STRANDEDNESS: both
    (D) TOPOLOGY: linear (ii) MOLECULE TYPE: cDNA (ix) FEATURE:
    (A) NAME/KEY: CDS
    (B) LOCATION: 1..132

(xi) SEQUENCE DESCRIPTION: SEQ ID NO:7:

```
GTG TCA CAT CGC AAA GGC CTC CCT CAT GTC ATC TAT TGC CGG GTT TGG       48
Val Ser His Arg Lys Gly Leu Pro His Val Ile Tyr Cys Arg Val Trp
 1               5                  10                  15

AGG TGG CCT GAT CTG CAG TCC CAT CAT GGG CTA AAA CCA ATG GAA TGC       96
Arg Trp Pro Asp Leu Gln Ser His His Gly Leu Lys Pro Met Glu Cys
            20                  25                  30

TGT GAG TTC CCT TTT GTG TCC AAG CAG AAG GAC GTG                      132
Cys Glu Phe Pro Phe Val Ser Lys Gln Lys Asp Val
        35                  40
```

(2) INFORMATION FOR SEQ ID NO:8:

(i) SEQUENCE CHARACTERISTICS:
       (A) LENGTH: 129 base pairs
       (B) TYPE: nucleic acid
       (C) STRANDEDNESS: both
       (D) TOPOLOGY: linear (ii) MOLECULE TYPE: cDNA (ix) FEATURE:
       (A) NAME/KEY: CDS
       (B) LOCATION: 1..129

(xi) SEQUENCE DESCRIPTION: SEQ ID NO:8:

```
GTA GCC GGC CGT AAA GGT TTC CCA CAT GTG ATC TAC GCT CGT TTG TGG       48
Val Ala Gly Arg Lys Gly Phe Pro His Val Ile Tyr Ala Arg Leu Trp
 1               5                  10                  15

CGC TGG CCG GAC CTG CAC AAG AAT GAG CTG AAA CAC GTT AAG TTC TGC       96
Arg Trp Pro Asp Leu His Lys Asn Glu Leu Lys His Val Lys Phe Cys
            20                  25                  30

CAG CTC GCC TTC GAC CTG AAG TAC GAC GAC GTG                          129
Gln Leu Ala Phe Asp Leu Lys Tyr Asp Asp Val
        35                  40
```

(2) INFORMATION FOR SEQ ID NO:9:

(i) SEQUENCE CHARACTERISTICS:
       (A) LENGTH: 132 base pairs
       (B) TYPE: nucleic acid
       (C) STRANDEDNESS: both
       (D) TOPOLOGY: linear (ii) MOLECULE TYPE: cDNA (ix) FEATURE:
       (A) NAME/KEY: CDS
       (B) LOCATION: 1..132

(xi) SEQUENCE DESCRIPTION: SEQ ID NO:9:

```
GTA CCC CAT CGA AAA GGA TTG CCA CAT GTT ATA TAT TGC CGA TTA TGG       48
Val Pro His Arg Lys Gly Leu Pro His Val Ile Tyr Cys Arg Leu Trp
 1               5                  10                  15

CGC TGG CCT GAT CTT CAC AGT CAT CAT GAA CTC AAG GCA ATT GAA AAC       96
Arg Trp Pro Asp Leu His Ser His His Glu Leu Lys Ala Ile Glu Asn
            20                  25                  30
```

```
TGC GAA TAT GCT TTT AAT CTT AAA AAG GAT GAA GTA                    132
Cys Glu Tyr Ala Phe Asn Leu Lys Lys Asp Glu Val
        35                  40
```

(2) INFORMATION FOR SEQ ID NO:10:

(i) SEQUENCE CHARACTERISTICS:
        (A) LENGTH: 132 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..132

(xi) SEQUENCE DESCRIPTION: SEQ ID NO:10:

```
GTG TCT CAC CGT AAA GGA TTG CCG CAT GTT ATC TAC TGC AGA CTG TGG    48
Val Ser His Arg Lys Gly Leu Pro His Val Ile Tyr Cys Arg Leu Trp
 1               5                  10                  15

CGC TGG CCA GAC CTG CAC AGT CAT CAT GAA CTG AAA GCA ATC GAA AAT    96
Arg Trp Pro Asp Leu His Ser His His Glu Leu Lys Ala Ile Glu Asn
            20                  25                  30

TGT GAA TAT GCT TTT AAC CTT AAA AAA GAT GAA GTT                    132
Cys Glu Tyr Ala Phe Asn Leu Lys Lys Asp Glu Val
        35                  40
```

(2) INFORMATION FOR SEQ ID NO:11:

(i) SEQUENCE CHARACTERISTICS:
        (A) LENGTH: 132 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..132

(xi) SEQUENCE DESCRIPTION: SEQ ID NO:11:

```
GTT TCT CAC AGA AAA GGC TTA CCC CAT GTT ATA TAT TGT CGT GTT TGG    48
Val Ser His Arg Lys Gly Leu Pro His Val Ile Tyr Cys Arg Val Trp
 1               5                  10                  15

CGC TGG CCG GAT TTG CAG AGT CAT CAT GAG CTA AAG CCG TTG GAT ATT    96
Arg Trp Pro Asp Leu Gln Ser His His Glu Leu Lys Pro Leu Asp Ile
            20                  25                  30

TGT GAA TTT CCT TTT GGA TCT AAG CAA AAA GAA GTT                    132
Cys Glu Phe Pro Phe Gly Ser Lys Gln Lys Glu Val
        35                  40
```

(2) INFORMATION FOR SEQ ID NO:12:

(i) SEQUENCE CHARACTERISTICS:
        (A) LENGTH: 519 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 16..519

(xi) SEQUENCE DESCRIPTION: SEQ ID NO:12:

```
ACTAGTGCTG TCATT ATG AAT GTG ACA AGT TTA TTT TCC TTT ACA AGT CCA      51
                Met Asn Val Thr Ser Leu Phe Ser Phe Thr Ser Pro
                  1               5                  10

GCT GTG AAG AGA CTT CTT GGG TGG AAA CAG GGC GAT GAA GAA AAA           99
Ala Val Lys Arg Leu Leu Gly Trp Lys Gln Gly Asp Glu Glu Lys
             15                  20                  25

TGG GCA GAG AAA GCT GTT GAT GCT TTG GTG AAA AAA CTG AAG AAA AAG      147
Trp Ala Glu Lys Ala Val Asp Ala Leu Val Lys Lys Leu Lys Lys Lys
         30                  35                  40

AAA GGT GCC ATG GAG GAA CTT GAA AAG GCC TTG AGC TGC CCA GGG CAA      195
Lys Gly Ala Met Glu Glu Leu Glu Lys Ala Leu Ser Cys Pro Gly Gln
     45                  50                  55                  60

CCG AGT AAC TGT GTC ACC ATT CCC CGC TCT CTG GAT GGC AGG CTG CAA      243
Pro Ser Asn Cys Val Thr Ile Pro Arg Ser Leu Asp Gly Arg Leu Gln
                 65                  70                  75

GTC TCC CAC CGG AAG GGA CTG CCT CAT GTC ATT TAC TGC CGT GTG TGG      291
Val Ser His Arg Lys Gly Leu Pro His Val Ile Tyr Cys Arg Val Trp
             80                  85                  90

CGC TGG CCC GAT CTT CAG AGC CAC CAT GAA CTA AAA CCA CTG GAA TGC      339
Arg Trp Pro Asp Leu Gln Ser His His Glu Leu Lys Pro Leu Glu Cys
         95                 100                 105

TGT GAG TTT CCT TTT GGT TCC AAG CAG AAG GAG GAG GTC TGC ATC AAT      387
Cys Glu Phe Pro Phe Gly Ser Lys Gln Lys Glu Glu Val Cys Ile Asn
    110                 115                 120

CCC TAC CAC TAT AAG AGA GTA GAA AGC CCT GTA CTT CCT CCT GTG CTG      435
Pro Tyr His Tyr Lys Arg Val Glu Ser Pro Val Leu Pro Pro Val Leu
125                 130                 135                 140

GTT CCA AGA CAC AGC GAA TAT AAT CCT CAG CAC AGC CTT TTA GCT CAG      483
Val Pro Arg His Ser Glu Tyr Asn Pro Gln His Ser Leu Leu Ala Gln
                145                 150                 155

TTC CGT AAC TTA GGA CAA AAT CAG CCT CAC ATG CCA                      519
Phe Arg Asn Leu Gly Gln Asn Gln Pro His Met Pro
            160                 165

(2) INFORMATION FOR SEQ ID NO:13:

(i) SEQUENCE CHARACTERISTICS:
        (A) LENGTH: 363 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..363

(xi) SEQUENCE DESCRIPTION: SEQ ID NO:13:

TAC TAC ATC GGA GGG GAG GTC TTC GCA GAG TGC CTC AGT GAC AGC GCT       48
Tyr Tyr Ile Gly Gly Glu Val Phe Ala Glu Cys Leu Ser Asp Ser Ala
  1               5                  10                  15

ATT TTG GTC CAG TCT CCC AAC TGT AAC CAG CGC TAT GGC TGG CAC CCG       96
Ile Leu Val Gln Ser Pro Asn Cys Asn Gln Arg Tyr Gly Trp His Pro
             20                  25                  30

GCC ACC GTC TGC AAG ATC CCA CCA GGA TGC AAC CTG AAG ATC TTC AAC      144
Ala Thr Val Cys Lys Ile Pro Pro Gly Cys Asn Leu Lys Ile Phe Asn
         35                  40                  45

AAC CAG GAG TTC GCT GCC CTC CTG GCC CAG TCG GTC AAC CAG GGC TTT      192
Asn Gln Glu Phe Ala Ala Leu Leu Ala Gln Ser Val Asn Gln Gly Phe
     50                  55                  60

CAG GCT GTC TAC CAG TTG ACC CGA ATG TGC ACC ATC CGC ATG AGC TTC      240
```

```
Gln Ala Val Tyr Gln Leu Thr Arg Met Cys Thr Ile Arg Met Ser Phe
 65                  70                  75                  80

GTC AAA GGC TGG GGA GCG GAG TAC AGG AGA CAG ACT GTG ACC AGT ACC        288
Val Lys Gly Trp Gly Ala Glu Tyr Arg Arg Gln Thr Val Thr Ser Thr
                 85                  90                  95

CCC TGC TGG ATT GAG CTG CAC CTG AAT GGG CCT TTG CAG TGG CTT GAC        336
Pro Cys Trp Ile Glu Leu His Leu Asn Gly Pro Leu Gln Trp Leu Asp
                100                 105                 110

AAG GTC CTC ACC CAG ATG GGC TCC CCN                                    363
Lys Val Leu Thr Gln Met Gly Ser Pro
        115                 120
```

(2) INFORMATION FOR SEQ ID NO:14:

(i) SEQUENCE CHARACTERISTICS:
        (A) LENGTH: 464 amino acids
        (B) TYPE: amino acid
        (D) TOPOLOGY: linear (ii) MOLECULE TYPE: protein (xi) SEQUENCE DESCRIPTION: SEQ ID NO:14:

```
Met Asn Val Thr Ser Leu Phe Ser Phe Thr Ser Pro Ala Val Lys Arg
  1               5                  10                  15

Leu Leu Gly Trp Lys Gln Gly Asp Glu Glu Lys Trp Ala Glu Lys
                 20                  25                  30

Ala Val Asp Ala Leu Val Lys Lys Leu Lys Lys Lys Gly Ala Met
             35                  40                  45

Glu Glu Leu Glu Lys Ala Leu Ser Cys Pro Gly Gln Pro Ser Asn Cys
 50                  55                  60

Val Thr Ile Pro Arg Ser Leu Asp Gly Arg Leu Gln Val Ser His Arg
 65                  70                  75                  80

Lys Gly Leu Pro His Val Ile Tyr Cys Arg Val Trp Arg Trp Pro Asp
                 85                  90                  95

Leu Gln Ser His His Glu Leu Lys Pro Leu Glu Cys Cys Glu Tyr Pro
                100                 105                 110

Phe Gly Ser Lys Gln Lys Glu Val Cys Ile Asn Pro Tyr His Tyr Lys
            115                 120                 125

Arg Val Glu Ser Pro Val Leu Pro Pro Val Leu Val Pro Arg His Ser
130                 135                 140

Glu Tyr Asn Pro Gln His Ser Leu Leu Ala Gln Phe Arg Asn Leu Glu
145                 150                 155                 160

Pro Ser Glu Pro His Met Pro His Asn Ala Thr Phe Pro Asp Ser Phe
                165                 170                 175

Gln Gln Pro Asn Ser His Pro Phe Pro His Ser Pro Asn Ser Ser Tyr
                180                 185                 190

Pro Asn Ser Pro Gly Ser Gly Ser Thr Tyr Pro His Ser Pro Ala Ser
            195                 200                 205

Ser Asp Pro Gly Ser Pro Phe Gln Ile Pro Ala Asp Thr Pro Pro Pro
210                 215                 220

Ala Tyr Met Pro Pro Glu Asp Gln Met Thr Gln Asp Asn Ser Gln Pro
225                 230                 235                 240

Met Asp Thr Asn Leu Met Val Pro Asn Ile Ser Gln Asp Ile Asn Arg
                245                 250                 255

Ala Asp Val Gln Ala Val Ala Tyr Glu Glu Pro Lys His Trp Cys Ser
            260                 265                 270

Ile Val Tyr Tyr Glu Leu Asn Asn Arg Val Gly Glu Ala Phe His Ala
```

```
                    275                 280                 285
Ser Ser Thr Ser Val Leu Val Asp Gly Phe Thr Asp Pro Ser Asn Asn
    290                 295                 300

Arg Asn Arg Phe Cys Leu Gly Leu Leu Ser Asn Val Asn Arg Asn Ser
305                 310                 315                 320

Thr Ile Glu Asn Thr Arg Arg His Ile Gly Lys Gly Val His Leu Tyr
                325                 330                 335

Tyr Val Gly Gly Glu Val Tyr Ala Glu Cys Leu Ser Asp Ser Ser Ile
            340                 345                 350

Phe Val Gln Ser Arg Asn Cys Asn Phe His His Gly Phe His Pro Thr
            355                 360                 365

Thr Val Cys Lys Ile Pro Ser Gly Cys Ser Leu Lys Ile Phe Asn Asn
    370                 375                 380

Gln Glu Phe Ala Gln Leu Leu Ala Gln Ser Val Asn His Gly Phe Glu
385                 390                 395                 400

Thr Val Tyr Glu Leu Thr Lys Met Cys Thr Ile Arg Met Ser Phe Val
                405                 410                 415

Lys Gly Trp Gly Ala Glu Cys His Arg Gln Asn Val Thr Ser Thr Pro
            420                 425                 430

Cys Trp Ile Glu Ile His Leu His Gly Pro Leu Gln Trp Leu Asp Lys
            435                 440                 445

Val Leu Thr Gln Met Gly Ser Pro His Asn Pro Ile Ser Ser Val Ser
    450                 455                 460

(2) INFORMATION FOR SEQ ID NO:15:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:15:

Met Ser Ser Ile Leu Pro Phe Thr Pro Pro Val Val Lys Arg Leu Leu
  1               5                  10                  15

Gly Trp Lys Lys Ser Ala Ser Gly Thr Thr Gly Ala Gly Gly Asp Glu
                 20                  25                  30

Gln Asn Gly Gln Glu Glu Lys Trp Cys Glu Lys Ala Val Lys Ser Leu
             35                  40                  45

Val Lys Lys Leu Lys Lys Thr Gly Gln Leu Asp Glu Leu Glu Lys Ala
     50                  55                  60

Ile Thr Thr Gln Asn Cys Asn Thr Lys Cys Val Thr Ile Pro Ser Thr
 65                  70                  75                  80

Cys Ser Glu Ile Trp Gly Leu Ser Thr Ala Asn Thr Ile Asp Gln Trp
                 85                  90                  95

Asp Thr Thr Gly Leu Tyr Ser Phe Ser Glu Gln Thr Arg Ser Leu Asp
                100                 105                 110

Gly Arg Leu Gln Val Ser His Arg Lys Gly Leu Pro His Val Ile Tyr
            115                 120                 125

Cys Arg Leu Trp Arg Trp Pro Asp Leu His Ser His His Glu Leu Lys
        130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175
```

```
Pro Val Leu Val Pro Arg His Thr Glu Ile Leu Thr Glu Leu Pro Pro
            180                 185                 190

Leu Asp Asp Tyr Thr His Ser Ile Pro Glu Asn Thr Asn Phe Pro Ala
            195                 200                 205

Gly Ile Glu Pro Gln Ser Asn Tyr Ile Pro Glu Thr Pro Pro Gly
            210                 215                 220

Tyr Ile Ser Glu Asp Gly Glu Thr Ser Asp Gln Gln Leu Asn Gln Ser
225                 230                 235                 240

Met Asp Thr Gly Ser Pro Ala Glu Leu Ser Pro Ser Thr Leu Ser Pro
            245                 250                 255

Val Asn His Asn Leu Asp Leu Gln Pro Val Thr Tyr Ser Glu Pro Ala
            260                 265                 270

Phe Trp Cys Ser Ile Ala Tyr Tyr Glu Leu Asn Gln Arg Val Gly Glu
            275                 280                 285

Thr Phe His Ala Ser Gln Pro Ser Leu Thr Val Asp Gly Phe Thr Asp
            290                 295                 300

Pro Ser Asn Ser Glu Arg Phe Cys Leu Gly Leu Leu Ser Asn Val Asn
305                 310                 315                 320

Arg Asn Ala Thr Val Glu Met Thr Arg Arg His Ile Gly Arg Gly Val
            325                 330                 335

Arg Leu Tyr Tyr Ile Gly Gly Glu Val Phe Ala Glu Cys Leu Ser Asp
            340                 345                 350

Ser Ala Ile Phe Val Gln Ser Pro Asn Cys Asn Gln Arg Tyr Gly Trp
            355                 360                 365

His Pro Ala Thr Val Cys Lys Ile Pro Pro Gly Cys Asn Leu Lys Ile
            370                 375                 380

Phe Asn Asn Gln Glu Phe Ala Ala Leu Leu Ala Gln Ser Val Asn Gln
385                 390                 395                 400

Gly Phe Glu Ala Val Tyr Gln Leu Thr Arg Met Cys Thr Ile Arg Met
            405                 410                 415

Ser Phe Val Lys Gly Trp Gly Ala Glu Tyr Arg Arg Gln Thr Val Thr
            420                 425                 430

Ser Thr Pro Cys Trp Ile Glu Leu His Leu Asn Gly Pro Leu Gln Trp
            435                 440                 445

Leu Asp Lys Val Leu Thr Gln Met Gly Ser Pro Ser Val Arg Cys Ser
            450                 455                 460

Ser Met Ser
465

(2) INFORMATION FOR SEQ ID NO:16:

(i) SEQUENCE CHARACTERISTICS:
        (A) LENGTH: 466 amino acids
        (B) TYPE: amino acid
        (D) TOPOLOGY: linear (ii) MOLECULE TYPE: protein (xi) SEQUENCE DESCRIPTION: SEQ ID NO:16:

Met His Ala Ser Thr Pro Ile Ser Ser Leu Phe Ser Phe Thr Ser Pro
1               5                   10                  15

Ala Val Lys Arg Leu Leu Gly Trp Lys Gln Gly Asp Glu Glu Glu Lys
            20                  25                  30

Trp Ala Glu Lys Ala Val Asp Ser Leu Val Lys Lys Leu Lys Lys Lys
            35                  40                  45
```

-continued

```
Lys Gly Ala Met Glu Glu Leu Glu Arg Ala Leu Ser Cys Pro Gly Gln
 50                  55                  60

Pro Ser Lys Cys Val Thr Ile Pro Arg Ser Leu Asp Gly Arg Leu Gln
 65                  70                  75                  80

Val Ser His Arg Lys Gly Leu Pro His Val Ile Tyr Cys Arg Val Trp
                 85                  90                  95

Arg Trp Pro Asp Leu Gln Ser His Glu Leu Lys Pro Met Glu Cys
                100                 105                 110

Cys Glu Phe Pro Phe Gly Ser Lys Gln Lys Asp Val Cys Ile Asn Pro
                115                 120                 125

Tyr His Tyr Arg Arg Val Glu Thr Pro Val Leu Pro Pro Val Leu Val
                130                 135                 140

Pro Arg His Ser Glu Phe Asn Pro Gln Leu Ser Leu Leu Ala Lys Phe
145                 150                 155                 160

Arg Asn Thr Ser Leu Asn Asn Glu Pro Leu Met Pro His Asn Ala Thr
                165                 170                 175

Phe Pro Glu Ser Phe Gln Gln Pro Pro Cys Thr Pro Phe Ser Ser Ser
                180                 185                 190

Pro Ser Asn Ile Phe Ser Gln Ser Pro Asn Thr Val Gly Tyr Pro Asp
                195                 200                 205

Ser Pro Arg Ser Ser Thr Asp Pro Gly Ser Pro Tyr Gln Ile Thr
                210                 215                 220

Glu Thr Pro Pro Pro Tyr Asn Ala Pro Asp Leu Gln Gly Asn Gln
225                 230                 235                 240

Asn Arg Pro Thr Ala Asp Pro Ala Glu Cys Gln Leu Val Leu Ser Ala
                245                 250                 255

Leu Asn Arg Asp Phe Arg Pro Val Cys Tyr Glu Glu Pro Leu His Trp
                260                 265                 270

Cys Ser Val Ala Tyr Tyr Glu Leu Asn Asn Arg Val Gly Glu Thr Phe
                275                 280                 285

Gln Ala Ser Ala Arg Ser Val Leu Ile Asp Gly Phe Thr Asp Pro Ser
290                 295                 300

Asn Asn Lys Asn Arg Phe Cys Leu Gly Leu Leu Ser Asn Val Asn Arg
305                 310                 315                 320

Asn Ser Thr Ile Glu Asn Thr Arg Arg His Ile Gly Lys Gly Val His
                325                 330                 335

Leu Tyr Tyr Val Gly Gly Glu Val Tyr Ala Glu Cys Val Ser Asp Ser
                340                 345                 350

Ser Ile Phe Val Gln Ser Arg Asn Cys Asn Tyr Gln His Gly Phe His
                355                 360                 365

Pro Ser Thr Val Arg Lys Ile Pro Ser Gly Cys Ser Leu Lys Ile Phe
                370                 375                 380

Asn Asn Gln Leu Phe Ala Gln Leu Leu Ser Gln Ser Val Asn Gln Gly
385                 390                 395                 400

Phe Glu Val Val Tyr Glu Leu Thr Lys Met Cys Thr Ile Arg Met Ser
                405                 410                 415

Phe Val Lys Gly Trp Gly Ala Glu Tyr Asn Arg Gln Asp Val Thr Ser
                420                 425                 430

Thr Pro Cys Trp Ile Glu Ile His Leu His Gly Pro Leu Gln Trp Leu
                435                 440                 445

Asp Lys Val Leu Thr Gln Met Gly Ser Pro His Asn Pro Ile Ser Ser
450                 455                 460

Val Ser
```

465

(2) INFORMATION FOR SEQ ID NO:17:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:17:

```
Met Ala Phe Ala Ser Leu Glu Leu Ala Leu His Arg Val Pro Pro Ala
 1               5                  10                  15

Arg Cys Gly Asp Glu Glu Ile Tyr Gly Glu Gly Leu Ser Glu Gly Glu
                20                  25                  30

Ile Pro Ala Met Ser Leu Thr Pro Pro Asn Ser Ser Asp Ala Cys Leu
                35                  40                  45

Ser Ile Val His Ser Leu Met Cys His Arg Gln Gly Gly Glu Asn Glu
        50                  55                  60

Gly Phe Ala Lys Arg Ala Ile Glu Ser Leu Val Lys Lys Leu Lys Glu
 65                  70                  75                  80

Lys Lys Asp Glu Leu Asp Ser Leu Ile Thr Ala Ile Thr Thr Asn Gly
                85                  90                  95

Val His Pro Ser Lys Cys Val Thr Ile Gln Arg Thr Leu Asp Gly Arg
                100                 105                 110

Leu Gln Val Ala Gly Arg Lys Gly Phe Pro His Val Ile Tyr Ala Arg
                115                 120                 125

Leu Trp His Trp Pro Asp Leu His Lys Asn Glu Leu Lys His Val Lys
130                 135                 140

Phe Cys Gln Phe Ala Phe Asp Leu Lys Tyr Asp Ser Val Cys Val Asn
145                 150                 155                 160

Pro Tyr His Tyr Glu Arg Val Val Ser Pro Gly Ile Gly Leu Ser Ile
                165                 170                 175

Pro Ser Thr Val Thr Thr Pro Cys Arg Ser Val Lys Glu Glu Tyr Val
                180                 185                 190

His Glu Cys Glu Met Asp Ala Ser Ser Cys Leu Pro Ala Ser Gln Glu
                195                 200                 205

Leu Pro Pro Ala Ile Lys His Ala Ser Leu Pro Pro Met Pro Pro Thr
210                 215                 220

Glu Ser Tyr Arg Gln Pro Leu Pro Pro Leu Thr Leu Pro Lys Ser Pro
225                 230                 235                 240

Gln Thr Ala Ile Ser Met Tyr Pro Asn Met Pro Leu Ser Pro Ser Val
                245                 250                 255

Ala Pro Gly Cys Pro Leu Ile Pro Met His Gly Glu Gly Leu Leu Gln
                260                 265                 270

Ile Ala Pro Ser His Pro Gln Gln Met Leu Ser Ile Ser Pro Pro Ser
                275                 280                 285

Thr Pro Ser Gln Asn Ser Gln Gln Asn Gly Tyr Ser Ser Pro Pro Lys
                290                 295                 300

Gln Pro Phe His Ala Ser Trp Thr Gly Ser Ser Thr Ala Val Tyr Thr
305                 310                 315                 320

Pro Asn Pro Gly Val Gln Gln Asn Gly Lys Gly Asn Gln Gln Pro Pro
                325                 330                 335

Leu His His Ala Asn Asn Tyr Trp Pro Leu His Gln Ser Ser Pro Gln
                340                 345                 350
```

```
Tyr Gln His Pro Val Ser Asn His Pro Gly Pro Glu Phe Trp Cys Ser
        355                 360                 365
Val Ala Tyr Phe Glu Met Asp Val Gln Val Gly Glu Ile Phe Lys Val
        370                 375                 380
Pro Ser Asn Cys Pro Val Val Thr Val Asp Gly Tyr Val Asp Pro Ser
385                 390                 395                 400
Gly Gly Asp Arg Phe Cys Leu Gly Gln Leu Ser Asn Val His Arg Thr
                405                 410                 415
Asp Thr Ser Glu Arg Ala Arg Leu His Ile Gly Lys Gly Val Gln Leu
                420                 425                 430
Glu Cys Arg Gly Glu Gly Asp Val Trp Met Arg Cys Leu Ser Asp His
            435                 440                 445
Ala Val Phe Val Gln Ser Tyr Tyr Leu Asp Arg Glu Ala Gly Arg Ala
        450                 455                 460
Pro Gly Asp Ala Val His Lys Ile Tyr Pro Gly Ala Tyr Ile Lys Val
465                 470                 475                 480
Phe Asp Leu Arg Gln Cys His Arg Gln Met Gln Gln Ala Ala Thr
                485                 490                 495
Ala Gln Ala Ala Ala Ala Gln Ala Ala Val Ala Gly Ala Ile
            500                 505                 510
Pro Gly Pro Gly Ser Val Gly Gly Ile Ala Pro Ala Val Ser Leu Ser
            515                 520                 525
Ala Ala Ala Gly Ile Gly Val Asp Asp Leu Arg Arg Leu Cys Ile Leu
        530                 535                 540
Arg Leu Ser Phe Val Lys Gly Trp Gly Pro Asp Tyr Pro Arg Gln Ser
545                 550                 555                 560
Ile Lys Gln Thr Pro Cys Trp Ile Glu Val His Leu His Arg Ala Leu
                565                 570                 575
Gln Leu Leu Asp Glu Val Leu His Thr Leu Pro Met Ala Asp Pro Ser
            580                 585                 590
Ser Val Asn
        595

(2) INFORMATION FOR SEQ ID NO:18:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:18:

Val Ser His Arg Lys Gly Leu Pro His Val Ile Tyr Cys Arg Val Trp
1               5                   10                  15
Arg Trp Pro Asp Leu Gln Ser His His Glu Leu Lys Pro Leu Glu Cys
                20                  25                  30
Cys Glu Phe Pro Phe Gly Ser Lys Gln Lys Glu Val
            35                  40

(2) INFORMATION FOR SEQ ID NO:19:

(i) SEQUENCE CHARACTERISTICS:
        (A) LENGTH: 44 amino acids
        (B) TYPE: amino acid
        (D) TOPOLOGY: linear (ii) MOLECULE TYPE: protein
```

(xi) SEQUENCE DESCRIPTION: SEQ ID NO:19:

Val Ala Gly Arg Lys Gly Phe Pro His Val Ile Tyr Ala Arg Leu Trp
 1               5                  10                  15

Arg Trp Pro Asp Leu His Lys Asn Glu Leu Lys His Val Lys Tyr Cys
                20                  25                  30

Gln Tyr Ala Phe Asp Leu Lys Cys Asp Ser Val Cys
            35                  40

(2) INFORMATION FOR SEQ ID NO:20:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:20:

Val Ser His Arg Lys Gly Leu Pro His Val Ile Tyr Cys Arg Val Trp
 1               5                  10                  15

Arg Trp Pro Asp Leu Gln Ser His His Gly Leu Lys Pro Met Glu Cys
                20                  25                  30

Cys Glu Phe Pro Phe Val Ser Lys Gln Lys Asp Val
            35                  40

(2) INFORMATION FOR SEQ ID NO:21:

(i) SEQUENCE CHARACTERISTICS:
        (A) LENGTH: 43 amino acids
        (B) TYPE: amino acid
        (D) TOPOLOGY: linear (ii) MOLECULE TYPE: protein (xi) SEQUENCE DESCRIPTION: SEQ ID NO:21:

Val Ala Gly Arg Lys Gly Phe Pro His Val Ile Tyr Ala Arg Leu Trp
 1               5                  10                  15

Arg Trp Pro Asp Leu His Lys Asn Glu Leu Lys His Val Lys Phe Cys
                20                  25                  30

Gln Leu Ala Phe Asp Leu Lys Tyr Asp Asp Val
            35                  40

(2) INFORMATION FOR SEQ ID NO:22:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:22:

Val Pro His Arg Lys Gly Leu Pro His Val Ile Tyr Cys Arg Leu Trp
 1               5                  10                  15

Arg Trp Pro Asp Leu His Ser His His Glu Leu Lys Ala Ile Glu Asn
                20                  25                  30

Cys Glu Tyr Ala Phe Asn Leu Lys Lys Asp Glu Val
            35                  40

(2) INFORMATION FOR SEQ ID NO:23:

(i) SEQUENCE CHARACTERISTICS:

(A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:23:

Val Ser His Arg Lys Gly Leu Pro His Val Ile Tyr Cys Arg Leu Trp
1               5                   10                  15

Arg Trp Pro Asp Leu His Ser His His Glu Leu Lys Ala Ile Glu Asn
            20                  25                  30

Cys Glu Tyr Ala Phe Asn Leu Lys Lys Asp Glu Val
            35                  40

(2) INFORMATION FOR SEQ ID NO:24:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO:24:

Val Ser His Arg Lys Gly Leu Pro His Val Ile Tyr Cys Arg Val Trp
1               5                   10                  15

Arg Trp Pro Asp Leu Gln Ser His His Glu Leu Lys Pro Leu Asp Ile
            20                  25                  30

Cys Glu Phe Pro Phe Gly Ser Lys Gln Lys Glu Val
            35                  40

(2) INFORMATION FOR SEQ ID NO:25:

(i) SEQUENCE CHARACTERISTICS:
        (A) LENGTH: 168 amino acids
        (B) TYPE: amino acid
        (D) TOPOLOGY: linear (ii) MOLECULE TYPE: protein (xi) SEQUENCE DESCRIPTION: SEQ ID NO:25:

Met Asn Val Thr Ser Leu Phe Ser Phe Thr Ser Pro Ala Val Lys Arg
1               5                   10                  15

Leu Leu Gly Trp Lys Gln Gly Asp Glu Glu Glu Lys Trp Ala Glu Lys
            20                  25                  30

Ala Val Asp Ala Leu Val Lys Lys Leu Lys Lys Lys Lys Gly Ala Met
            35                  40                  45

Glu Glu Leu Glu Lys Ala Leu Ser Cys Pro Gly Gln Pro Ser Asn Cys
    50                  55                  60

Val Thr Ile Pro Arg Ser Leu Asp Gly Arg Leu Gln Val Ser His Arg
65                  70                  75                  80

Lys Gly Leu Pro His Val Ile Tyr Cys Arg Val Trp Arg Trp Pro Asp
                85                  90                  95

Leu Gln Ser His His Glu Leu Lys Pro Leu Glu Cys Cys Glu Phe Pro
            100                 105                 110

Phe Gly Ser Lys Gln Lys Glu Val Cys Ile Asn Pro Tyr His Tyr
            115                 120                 125

Lys Arg Val Glu Ser Pro Val Leu Pro Pro Val Leu Val Pro Arg His
            130                 135                 140

Ser Glu Tyr Asn Pro Gln His Ser Leu Leu Ala Gln Phe Arg Asn Leu
145                 150                 155                 160

```
Gly Gln Asn Gln Pro His Met Pro
            165
```

(2) INFORMATION FOR SEQ ID NO:26:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:26:

```
Tyr Tyr Ile Gly Gly Glu Val Phe Ala Glu Cys Leu Ser Asp Ser Ala
 1               5                  10                  15

Ile Leu Val Gln Ser Pro Asn Cys Asn Gln Arg Tyr Gly Trp His Pro
            20                  25                  30

Ala Thr Val Cys Lys Ile Pro Pro Gly Cys Asn Leu Lys Ile Phe Asn
            35                  40                  45

Asn Gln Glu Phe Ala Ala Leu Leu Ala Gln Ser Val Asn Gln Gly Phe
        50                  55                  60

Gln Ala Val Tyr Gln Leu Thr Arg Met Cys Thr Ile Arg Met Ser Phe
65                  70                  75                  80

Val Lys Gly Trp Gly Ala Glu Tyr Arg Arg Gln Thr Val Thr Ser Thr
                85                  90                  95

Pro Cys Trp Ile Glu Leu His Leu Asn Gly Pro Leu Gln Trp Leu Asp
            100                 105                 110

Lys Val Leu Thr Gln Met Gly Ser Pro
            115                 120
```

(2) INFORMATION FOR SEQ ID NO:27:

(i) SEQUENCE CHARACTERISTICS:
        (A) LENGTH: 53 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:27:

```
Leu Val Lys Lys Leu Lys Xaa Cys Val Thr Ile Xaa Arg Xaa Leu Asp
 1               5                  10                  15

Gly Arg Leu Gln Val Xaa Xaa Arg Lys Gly Xaa Pro His Val Ile Tyr
            20                  25                  30

Xaa Arg Xaa Trp Xaa Trp Pro Asp Leu Xaa Val Cys Xaa Asn Pro Tyr
        35                  40                  45

His Tyr Xaa Arg Val
        50
```

(2) INFORMATION FOR SEQ ID NO:28:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:28:

Leu Asp Gly Arg Leu Gln Val Xaa Xaa Arg Lys Gly Xaa Pro His Val
1               5                   10                  15

Ile Tyr Xaa Arg Xaa Trp Xaa Trp Pro Asp Leu
            20                  25

(2) INFORMATION FOR SEQ ID NO:29:

(i) SEQUENCE CHARACTERISTICS:
        (A) LENGTH: 46 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:29:

Leu Xaa Xaa Xaa Cys Xaa Xaa Arg Xaa Ser Phe Val Lys Gly Trp Gly
1               5                   10                  15

Xaa Xaa Xaa Xaa Arg Gln Xaa Xaa Xaa Xaa Thr Pro Cys Trp Ile Glu
            20                  25                  30

Xaa His Leu Xaa Xaa Xaa Leu Gln Xaa Leu Asp Xaa Val Leu
        35                  40                  45

(2) INFORMATION FOR SEQ ID NO:30:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:30:

Leu Asp Gly Arg Leu Gln Val Ser His Arg Lys Gly Leu Pro His Val
1               5                   10                  15

Ile Tyr Cys Arg Val Trp Arg Trp Pro Asp Leu Gln Ser His His Glu
            20                  25                  30

Leu Lys Pro Xaa Glu Cys Cys Glu Xaa Pro Phe Xaa Ser Lys Gln Lys
        35                  40                  45

Xaa Val
    50

(2) INFORMATION FOR SEQ ID NO:31:

(i) SEQUENCE CHARACTERISTICS:
        (A) LENGTH: 49 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:31:

Leu Asp Gly Arg Leu Gln Val Ala Gly Arg Lys Gly Phe Pro His Val
1               5                   10                  15

Ile Tyr Ala Arg Leu Trp Xaa Trp Pro Asp Leu His Lys Asn Glu Leu

```
            20                  25                  30
Lys His Val Lys Phe Cys Gln Xaa Ala Phe Asp Leu Lys Tyr Asp Xaa
        35                  40                  45
Val
```

(2) INFORMATION FOR SEQ ID NO:32:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:32:

```
Leu Asp Gly Arg Leu Gln Val Xaa His Arg Lys Gly Leu Pro His Val
1               5                   10                  15

Ile Tyr Cys Arg Leu Trp Arg Trp Pro Asp Leu His Ser His His Glu
            20                  25                  30

Leu Lys Ala Ile Glu Asn Cys Glu Tyr Ala Phe Asn Leu Lys Lys Asp
        35                  40                  45

Glu Val
    50
```

(2) INFORMATION FOR SEQ ID NO:33:

(i) SEQUENCE CHARACTERISTICS:
        (A) LENGTH: 44 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:33:

```
Val Xaa Xaa Arg Lys Gly Xaa Pro His Val Ile Tyr Xaa Arg Xaa Trp
1               5                   10                  15

Arg Trp Pro Asp Leu Xaa Xaa Xaa Xaa Xaa Leu Lys Xaa Xaa Xaa Xaa
            20                  25                  30

Cys Xaa Xaa Xaa Phe Xaa Xaa Lys Xaa Xaa Xaa Val
        35                  40
```

(2) INFORMATION FOR SEQ ID NO:34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:34:

CGGGATCCTG AYGGMGYTCA RRT                                      23

(2) INFORMATION FOR SEQ ID NO:35:

(i) SEQUENCE CHARACTERISTICS:
        (A) LENGTH: 27 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:35:

CGGAATTCTA RTGRTAGGRT TDATRCA                                          27
```